(12) United States Patent
Kuhn et al.

(10) Patent No.: US 9,150,871 B2
(45) Date of Patent: Oct. 6, 2015

(54) REGULATORY NUCLEIC ACID MOLECULES FOR ENHANCING SEED-SPECIFIC AND/OR SEED-PREFERENTIAL GENE EXPRESSION IN PLANTS

(75) Inventors: Josef Martin Kuhn, Ludwigshafen (DE); Linda Patricia Loyall, Limburgerhof (DE); Malte Siebert, Heidelberg (DE); Elke Duwenig, Limburgerhof (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 476 days.

(21) Appl. No.: 13/393,045

(22) PCT Filed: Aug. 11, 2010

(86) PCT No.: PCT/EP2010/061661
§ 371 (c)(1),
(2), (4) Date: Feb. 28, 2012

(87) PCT Pub. No.: WO2011/023539
PCT Pub. Date: Mar. 3, 2011

(65) Prior Publication Data
US 2012/0159670 A1    Jun. 21, 2012

Related U.S. Application Data

(60) Provisional application No. 61/238,233, filed on Aug. 31, 2009.

(30) Foreign Application Priority Data

Aug. 31, 2009   (EP) .................................... 09169017

(51) Int. Cl.
C12N 5/04       (2006.01)
C12N 15/113     (2010.01)
C12N 15/82      (2006.01)

(52) U.S. Cl.
CPC .............. *C12N 15/8234* (2013.01); *C12N 5/04* (2013.01); *C12N 15/8216* (2013.01); *C12N 15/8241* (2013.01)

(58) Field of Classification Search
None
See application file for complete search history.

(56) References Cited

U.S. PATENT DOCUMENTS

| | | | |
|---|---|---|---|
| 5,750,866 | A | 5/1998 | Dietrich et al. |
| 8,071,383 | B2 | 12/2011 | Arias et al. |
| 2005/0216967 | A1 | 9/2005 | Heim et al. |
| 2005/0246785 | A1 | 11/2005 | Cook et al. |
| 2006/0195934 | A1 | 8/2006 | Apuya et al. |
| 2006/0195943 | A1 | 8/2006 | Feldmann et al. |
| 2007/0006335 | A1 | 1/2007 | Cook et al. |
| 2007/0006345 | A1 | 1/2007 | Alexandrov et al. |
| 2007/0006347 | A1 | 1/2007 | Plesch et al. |
| 2009/0172837 | A1 | 7/2009 | Geiger et al. |
| 2010/0192237 | A1 | 7/2010 | Ren et al. |
| 2010/0199365 | A1 | 8/2010 | Senger et al. |
| 2011/0014706 | A2* | 1/2011 | Cao et al. ...................... 435/419 |
| 2012/0084885 | A1* | 4/2012 | Alexandrov et al. ......... 800/298 |
| 2012/0167248 | A1 | 6/2012 | Kuhn et al. |
| 2012/0185965 | A1 | 7/2012 | Senger et al. |
| 2015/0052636 | A1* | 2/2015 | Hartig et al. .................. 800/287 |

FOREIGN PATENT DOCUMENTS

| | | |
|---|---|---|
| CL | 2007000696 A1 | 6/2008 |
| EP | 1645633 A2 | 4/2006 |
| JP | 2009/529863 A | 8/2009 |
| RU | 2197527 C2 | 1/2003 |
| WO | WO-93/20216 A1 | 10/1993 |
| WO | WO-99/67389 A2 | 12/1999 |
| WO | WO-00/55325 A2 | 9/2000 |
| WO | WO-01/98480 A2 | 12/2001 |
| WO | WO-02/16655 A2 | 2/2002 |
| WO | WO-03/006660 A1 | 1/2003 |
| WO | WO-03/008596 A2 | 1/2003 |
| WO | WO-03/102198 A1 | 12/2003 |
| WO | WO-2006/003186 A1 | 1/2006 |
| WO | WO-2006/032426 A2 | 3/2006 |
| WO | WO-2006/089950 A2 | 8/2006 |
| WO | WO-2007/039454 A1 | 4/2007 |
| WO | WO-2007/098042 A2 | 8/2007 |
| WO | WO-2007/107516 A2 | 9/2007 |
| WO | WO-2007/112326 A1 | 10/2007 |
| WO | WO-2008/009600 A1 | 1/2008 |
| WO | WO-2008/064128 A2 | 5/2008 |

(Continued)

OTHER PUBLICATIONS

GenBank Accession No. AC0072330.2. *Arabidopsis thaliana* chromosome 1 BAC T23K8 sequence. Published May 13, 1999. pp. 1-17.*

"Transgenic plant; promoter; ds; gene silencing; RNA interference; gene expression; PT0723", Genbank Database, Accession No. AJV39144, Nov. 29, 2007.

Baeumlein, H., et al., "A Novel Seed Protein Gene from *Vicia faba* is Developmentally Regulated in Transgenic Tobacco and *Arabidopsis* Plants", Mol. Gen. Genet., vol. 225, (1991), pp. 459-467.

Bruce, W. B., et al., "*cis*-Acting Elements Involved in Photoregulation of an Oat Phytochrome Promoter in Rice", The Plant Cell, vol. 2, (1990), pp. 1081-1089.

Callis, J., et al., "Introns Increase Gene Expression in Cultured Maize Cells", Genes & Development, vol. 1, (1987), pp. 1183-1200.

(Continued)

*Primary Examiner* — Anne Kubelik
*Assistant Examiner* — Ashley K Buran
(74) *Attorney, Agent, or Firm* — Drinker Biddle & Reath LLP

(57) ABSTRACT

The present invention is in the field of plant molecular biology and provides methods for production of high expressing seed-specific and/or seed-preferential promoters and the production of plants with enhanced seed-specific and/or seed-preferential expression of nucleic acids wherein nucleic acid expression enhancing nucleic acids (NEENAs) are functionally linked to said promoters and/or introduced into plants.

23 Claims, 5 Drawing Sheets

(56) References Cited

FOREIGN PATENT DOCUMENTS

Figure 1:
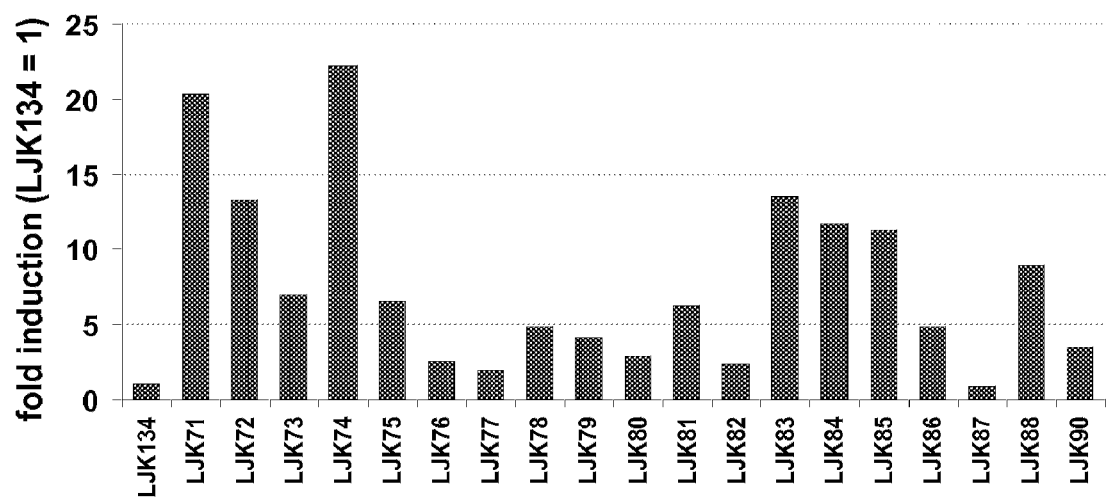

| WO | WO-2008/104559 A1 | 9/2008 |
|---|---|---|
| WO | WO-2009/016202 A2 | 2/2009 |
| WO | WO-2009/037329 A2 | 3/2009 |
| WO | WO-2011/023537 A1 | 3/2011 |
| WO | WO-2011/023539 A1 | 3/2011 |
| WO | WO-2011/023800 A1 | 3/2011 |

OTHER PUBLICATIONS

Chen, Z.L., et al., "A DNA Sequence Element that Confers Seed-Specific Enhancement to a Constitutive Promoter", The EMBO Journal, vol. 7, No. 2, (1988), pp. 297-302.
Chung, B.Y.W., et al., "Effect of 5_UTR Introns on Gene Expression in *Arabidopsis thaliana*", BMC Genomics, vol. 7, No. 120, (2006), pp. 1-13.
Fu, H., et al., "High-Level Tuber Expression and Sucrose Inducibility of a Potato Sus4 Sucrose Synthase Gene Require 5' and 3' Flanking Sequences and the Leader Intron", Plant Cell, vol. 7, 1387-1394.
Fu, H., et al., "A Potato *Sus3* Sucrose Synthase Gene Contains a Context-Dependent 3' Element and a Leader Intron with Both Positive and Negative Tissue-Specific Effects", The Plant Cell, vol. 7, (1995), pp. 1395-1403.
Huang, M.T.F., "Intervening Sequences Increase Efficiency of RNA 3' Processing and Accumulation of Cytoplasmic RNA", Nucleic Acid Research, vol. 18, No. 4, ((1989), pp. 937-947.
Kim, M. J., et al., "Seed-Specific Expression of Sesame Microsomal Oleic Acid Desaturase is Controlled by Combinatorial Properties Between Negative *cis*-Regulatory Elements in the *SeFAD2* Promoter and Enhancers in the 5'-UTR Intron", Mol. Gen., Genomics, vol. 276, (2006), pp. 351-368.
Le Hir, H., et al., "How Introns Influence and Enhance Eukaryotic Gene Expression", Trends in Biochemical Sciences, vol. 28, No. 4, (2003), pp. 215-220.
Lu, J., et al., "Gene Expression Enhancement Mediated by the 5' UTR Intron of the Rice *rubi3* Gene Varied Remarkably Among Tissues in Transgenic Rice Plants", Mol. Genet. Genomics, vol. 279, (2008), pp. 563-572.
Nott, A., et al., "Splicing Enhances Translation in Mammalian Cells: an Additional Function of the Exon Junction Complex", Genes & Development, vol. 18, (2004), pp. 210-222.
Rose, A. B., "The Effect of Intron Location on Intron-Mediated Enhancement of Gene Expression in *Arabidopsis*", The Plant Journal, vol. 40, (2004), pp. 744-751.
Rose, A., B., et al., "Promoter-Proximal Introns in *Arabidopsis thatliana* are Enriched in Dispersed Signals that Elevate Gene Expression", The Plant Cell, vol. 20, (2008), pp. 543-551.
Schünmann, P.H.D., et al., Characterization of Promoter Expression Patterns Derived from the Pht1 Phosphate Transporter Genes of Barley (*Hordeum vulgare* L.), Journal of Experimental Botany, vol. 55, No. 398, (2004), pp. 855-865.
Sieburth, L. E., "Molecular Dissection of the *AGAMOUS* Control Region Shows that *cis* Elements for Spatial Regulation are Located Intragenically", The Plant Cell, vol. 9, (1997), pp. 355-365.
Vasil, V., et al., "Increased Gene Expression by the First Intron of Maize *Shrunken-1* Locus in Grass Species", Plant Physiol., vol. 91, (1989), pp. 1575-1579.
Vitale, A., et al., "Multiple Conserved 5' Elements are Required for High-Level Pollen Expression of the *Arabidopsis* Reproductive Actin *ACT1*", Plant Molecular Biology, vol. 52, (2003), pp. 1135-1151.
Wang, S., et al., "Control of Plant Trichome Development by a Cotton Fiber MYB Gene", The Plant Cell, vol. 16, (2004), pp. 2323-2334.
International Preliminary Report on Patentability for PCT/EP2010/061661, issued Mar. 6, 2012.
U.S. Appl. No. 13/393,063, filed Feb. 28, 2012, Senger et al.
U.S. Appl. No. 13/393,028, filed Feb. 28, 2012, Kuhn et al.
"*Petroselinum crispum* ubiquitin promoter DNA", NCBI database, Accession No. ADH50767, Mar. 25, 2004.
"*A. thaliana* At5g17920 gene constitutive promoter pSUH303GB", NCBI database, Accession No. AEH04981, Jun. 15, 2006.
"*Petroselinum crispum* UBI4-2 promoter sequence, SEQ ID 7", NCBI database, Accession No. AJV61209, Nov. 29, 2007.
"Sequence 230 from Patent WO0198480", EMBL Database, Accession No. AX461301, Jul. 8, 2002.
"*Arabidopsis thaliana* DNA chromosome 6, BAC clone F13G24 (ESSA project)", EMBL database, Accession No. AL133421, Dec. 10, 1999.
Thomas, M. S., et al, "Identification of an Enhancer Element for the Endosperm-Specific Expression of High Molecular Weight Glutenin", The Plant Cell, vol. 2, (1990), pp. 1171-1180.
Xie, M., et al., "Bidirectionalization of Polar Promoters in Plants", Nature Biotechnology, vol. 19, (2001), pp. 677-678.
Wilmink, A., et al., "Activity of Constitutive Promoters in Various Species from the Liliaceae", Plant Molecular Biology, 1995, vol. 28, pp. 949-955.
Japanese Office Action for Japanese Application No. 2012-525978 Dated Oct. 21, 2014 with English Translation Attached.
Chilean Office Action Issued in Chilean Patent Application No. 2012-000550 Dated Feb. 11, 2015.
Decision of Grant Issued in Russian Patent Application No. 2012 112 347 Dated Apr. 1, 2015.
Decision of Grant Issued in Russian Patent Application No. 2012 112 346 Dated Apr. 1, 2015.

\* cited by examiner

A)

B)

A)

B)

ID

SEQUENCE LISTING

<160> NUMBER OF SEQ ID NOS: 87

<210> SEQ ID NO 1
<211> LENGTH: 847
<212> TYPE: DNA
<213> ORGANISM: Arabidopsis thaliana

<400> SEQUENCE: 1
tggtgcttaa acactctggt gagttctagt acttctgcta tgatcgatct cattaccatt      60
tcttaaattt ctctccctaa atattccgag ttcttgattt tgataacttt caggtttttct    120 cttttttgata aatctggtct ttccattttt ttttttttgt ggttaattta gtttcctatg    180
ttcttcgatt gtattatgca tgatctgtgt ttggattctg ttagattatg tattggtgaa    240
tatgtatgtg tttttgcatg tctggttttg gtcttaaaaa tgttcaaatc tgatgatttg    300
attgaagctt ttttagtgtt ggtttgattc ttctcaaaac tactgttaat ttactatcat    360
gttttccaac tttgattcat gatgacactt tgttctgct tgttataaa attttggttg      420 gtttgatttt gtaattatag tgtaattttg ttaggaatga acatgttta atactctgtt      480 ttcgatttgt cacacattcg aattattaat cgataattta actgaaaatt catggttcta    540
gatcttgttg tcatcagatt atttgtttcg ataattcatc aaatatgtag tccttttgct    600
gatttgcgac tgtttcattt tttctcaaaa ttgttttttg ttaagtttat ctaacagtta    660
tcgttgtcaa aagtctcttt cattttgcaa aatcttcttt tttttttgt ttgtaactttt    720 gttttttaag ctacacattt agtctgtaaa atagcatcga ggaacagttg tcttagtaga    780
cttgcatgtt cttgtaactt ctatttgttt cagtttgttg atgactgctt tgattttgta    840
ggtcaaa                                                              847

<210> SEQ ID NO 2
<211> LENGTH: 455
<212> TYPE: DNA
<213> ORGANISM: Arabidopsis thaliana

<400> SEQUENCE: 2
agttctttgc tttcgaagtt gccgcaacct aaacaggttt ttccttcttc tttcttctta      60
ttaactacga ccttgtcctt tgcctatgta aaattactag gttttcatca gttcacactga    120 ttaagttcgt tatagtggaa gataaaatgc cctcaaagca ttttgcagga tatctttgat    180
ttttcaaaga tatggaactg tagagtttga tagtgttctt gaatgtggtt gcatgaagtt    240
tttttggtct gcatgttatt ttttcctcga aatatgtttt gagtccaaca agtgattcac    300
ttgggattca gaaagttgtt ttctcaatat gtaacagttt ttttctatgg agaaaaatca    360
tagggaccgt tggttttggc ttctttaatt ttgagctcag attaaaccca ttttacccgg    420
tgttcttggc agaattgaaa acagtacgta gtacc                                455

<210> SEQ ID NO 3
<211> LENGTH: 758
<212> TYPE: DNA
<213> ORGANISM: Arabidopsis thaliana

<400> SEQUENCE: 3
agggtttcgt ttttgtttca tcgataaact caaaggtgat gatttaggg tcttgtgagt       60 gtgctttttt gtttgattct actgtagggt ttatgttctt tagctcatag gttttgtgta    120
tttcttagaa atgtggcttc tttaatctct gggtttgtga cttttgtgt ggtttctgtg    180 tttttcatat caaaaaccta tttttccga gtttttttt acaaattctt actctcaagc     240

```
ttgaatactt cacatgcagt gttcttttgt agatttagaa gttaatgtgt taaaaagttt      300 ggattttct tgcttataga gcttcttcac tttgattttg tgggtttttt tgttttaaag       360
gtgagatttt tgatgaggtt tttgcttcaa agatgtcacc tttctgggtt tgtcttttga     420
ataaagctat gaactgtcac atggctgacg caattttgtt actatgtcat gaaagctgac     480 gttttccgt gttatacatg tttgcttaca cttgcatgcg tcaaaaaaat tggggctttt      540
tagttttagt caaagatttt acttctcttt tgggatttat gaaggaaagt tgcaaacttt     600 ctcaaattt accatttttg ctttgatgtt tgtttagatt gcgacagaac aaactcatat     660
atgttgaaat tttgcttgg ttttgtatag gattgtgtct tttgcttata aatgttgaaa    720
tctgaacttt ttttttgttt ggtttctttg agcaggag                            758

<210> SEQ ID NO 4
<211> LENGTH: 252
<212> TYPE: DNA
<213> ORGANISM: Arabidopsis thaliana

<400> SEQUENCE: 4
actgtttaag cttcactgtc tctgaatcgg caaaggtaaa cgtatcaatt attctacaaa     60
cccttttatt tttcttttga attaccgtct tcattggtta tatgataact tgataagtaa   120
agcttcaata attgaatttg atctgtgttt ttttggcctt aatactaaat ccttacataa   180
gctttgttgc ttctcctctt gtgagttgag tgttaagttg taataatggt tcactttcag   240
ctttagaaga aa                                                       252

<210> SEQ ID NO 5
<211> LENGTH: 377
<212> TYPE: DNA
<213> ORGANISM: Arabidopsis thaliana

<400> SEQUENCE: 5
tttcacgatt tggaatttga ttcctgcgat cacaggtatg acaggttaga ttttgttttg     60
tatagttgta tacatacttc tttgtgatgt tttgtttact taatcgaatt tttggagtgt   120
tttaaggtct ctcgtttaga aatcgtggaa aatatcactg tgtgtgtgtt cttatgattc   180 acagtgtttta tgggtttcat gttctttgtt ttatcattga atgggaagaa atttcgttgg   240
gatacaaatt tctcatgttc ttactgatcg ttattaggag tttggggaaa aaggaagagt   300
ttttttggtt ggttcgagtg attatgaggt tatttctgta tttgatttat gagttaatgg   360
tcgttttaat gttgtag                                                  377

<210> SEQ ID NO 6
<211> LENGTH: 718
<212> TYPE: DNA
<213> ORGANISM: Arabidopsis thaliana

<400> SEQUENCE: 6
gtccagaatt ttctccattg aagctggatt ctaaggtcag ttcttacttc tttatctcaa     60
tctgatgatt ccatatcgaa agtcttactt tttcacttca atttcaatct gatgattcta   120
agatctttga ttcgaggtcg atctctgata gttactacat gttctgggt ttatttattt   180 ttaatccata tagtaattaa aaactcttat gaggtttaat tatggttact tgagaatttg   240
caatcgtcat ctttctttga ctcctatcca ttttttggtt tttccttgt ttaatttctg    300 tttcataatt gtaattgtaa attaaccaaa acaaattgat cagaaaccctt tttcctatgg   360
```

```
aatatttatc acacgcaagc ctgtgagttg tgactctgta atcacttcct tgttctggta    420
atttcagtgg ttaaggctct ccttttttct gatgttgtca gcaaaagtta gttttcttc     480 ttctttaatg ggttaattac acctaaatct ctggttatta acaatccag aaagaaaaaa     540 agtttattcc ttcctctatg tatatagttt cacatgcaag catcacttgt tgttctgac     600 aaattgcaga gttttgagtt ctgttttttt tttttctaa tgttttgtct ttaagaaagt     660
tctgtttttt tttctgcagg aaagttatca aaagttttga gagctttgga tagtgaag      718

<210> SEQ ID NO 7
<211> LENGTH: 495
<212> TYPE: DNA
<213> ORGANISM: Arabidopsis thaliana

<400> SEQUENCE: 7
ctagcttaat ctcagattcg aatcgttcca tagtggtgag cttcgtgttc ttctttcgtc    60
tcttactcct gattctcgat tttagggttt tcagtaattg cgtcggcggc gaaagtcttt    120
atcgccgatc gatcttcctt atctagaaat tattgatcag aaactgttgg gttttgtttg    180
attcttgtca gtttgatt tttcatgcga aattgctcaa tcccaattca aagttacgat     240
ttttattgaa aaccctagat tggtttcttc aagtttgtca ctttgattca atctaatagc    300
ttagcttaat cgttaagtct cttttttggt tttaggtttc atttgcgatt taaaggttct    360
tgttttggta tttgtttttgc tttggtcctt taagtttgag aggcttatgt agattataag  420
agagaagagt attgctttgc atgtttaaag gaagaacttt taactgaaca tttgtatgat    480
tggtatgtag atact                                                     495

<210> SEQ ID NO 8
<211> LENGTH: 139
<212> TYPE: DNA
<213> ORGANISM: Arabidopsis thaliana

<400> SEQUENCE: 8
atttccacac gctttctatc atttccaccc aaaaggtaac gcgcttttta tttccttttcc   60 tgcattcata aatttgtctc ctgcatgttg aaaaaaaaaa atttacatcg agattcgttt   120
ttatttttta gagagagat                                                 139

<210> SEQ ID NO 9
<211> LENGTH: 889
<212> TYPE: DNA
<213> ORGANISM: Arabidopsis thaliana

<400> SEQUENCE: 9
gtctactttc attacagtga ctctgcatgc ttcaggtctc gtctaattct tgaattctct    60
tcttttctgt tccgtaattt actttctagg gtctctagat ttgtgtctcc tctaacaaaa    120
gatcctatct ttcgacaaat ttaatttcat cattgacctt tgtcgattcc attctctctc    180
tatctctctg tttcttcgaa aacctagagg ttttgaattt aatgattcct ttttatgtca    240
ataaatttgc aatcaatggg agcttttta aatcatcgtt atatctataa acaaaaaaac    300
agtaattact cttcttagat ctaaaacaat taataaatct ttccctttt tctcatcata    360 atttttttcgt atttaactct tgtaaaaatt tgcttagccg tttcgctttc tcaggcccca  420
ggtgattcgt gtcttctagg tcagcttgtg aaacctgaga gaagccatct tttgtttgcg    480
gttacaaact ttgccgcttc aatatttcat tgctgttttc tgggaaaacc ttttctagt     540 tttttcggct tattatgcct tttaacttt tgtgcattta acatttattg ttagtgcttt     600
```

```
gcttagtgta aagtagtagt tctctttgta atattaccat aaggttcaga agtaaatttt    660
tctaaaattg ttttcttgtg ggaaattcag actgatttca gcaacatgca tgggcttaaa    720
atcagcttct aagactgaga tttagtgacc agtgtggtgg tgtcttgttc tctgttcttg    780
ggagaacaca aaggcagtgt ggagtctggt gagttttctg attcttgaaa agatttataa    840
attttcttgc aaaattagtc tttatgttga attgtgttgc aggtaaaat                889

<210> SEQ ID NO 10
<211> LENGTH: 433
<212> TYPE: DNA
<213> ORGANISM: Arabidopsis thaliana

<400> SEQUENCE: 10
gcacaatctt agcttacctt gaatcacaac ttcaggtata tgtaactgat tctaaattga     60
agattgtgtg caaatcttat atccattttt tattattaaa tttattgaaa aagctagcgg    120
tgtaaattaa tgtcacaaaa tcagtatatt gttagttttt gttttttttg aagttttatg    180
caaatcttca aaagtatat tcagtgttgt aattgacaaa tagagactct agttcttttt    240 tttttttct tttttttaac atctgactct tatagagact ctagttcatg tacacttttt    300
ttaatggaaa aacaaatttg aaactgaata tcttatttcc acgtagattg tatattagtt    360
taatttgatt gttatatttg taaatgtcta ctaaacagga attggatggt gaggaggcaa    420
ggcttgtgga tta                                                      433

<210> SEQ ID NO 11
<211> LENGTH: 354
<212> TYPE: DNA
<213> ORGANISM: Arabidopsis thaliana

<400> SEQUENCE: 11
atcttagggt ttcgcgagat ctcactctca ctggtatgtc tgtgtttctt cttccattt      60 ctgtttctat tggaaacttc tctctccaat ttcgttttct tcacttcttt gatcctttag    120
ctttgacaaa accgtagtaa aggatcaaaa gttatcatct ttggtccatg ttgtgaatcg    180
tgctctgctt gggtcgtgac tcccaaatcc ggatttgaaa ccagcatatc tgagcttaat    240
tcgagcatgc atgcgcttct ttttttctga ttttttttag actttggttc taaatcccctt   300 aactttggat taactgtcaa tctacaattt tatattaaca gagatagctt agca          354

<210> SEQ ID NO 12
<211> LENGTH: 143
<212> TYPE: DNA
<213> ORGANISM: Arabidopsis thaliana

<400> SEQUENCE: 12
cagaagctca tttcttcgat acgatcaacc attaggtgat ttttttctct gatcttcgag     60
ttctgataat tgctcttttt tctctggctt tgttatcgat aatttctctg gattttcttt    120
ctggggtgaa ttttttgcgca gag                                          143

<210> SEQ ID NO 13
<211> LENGTH: 182
<212> TYPE: DNA
<213> ORGANISM: Arabidopsis thaliana

<400> SEQUENCE: 13
atttttgttg gtgaaaggta gaattcgtaa atttcttctg ctcactttat tgtttcgact     60
```

```
cataccgat aatctcttct atgtttggta gagatatctt ctcaaagtct tatctttcct      120
taccgtgttc tgtgttttt gatgatttag gtgaagaaga agaagcagag acaaaaacga     180
tt                                                                    182

<210> SEQ ID NO 14
<211> LENGTH: 665
<212> TYPE: DNA
<213> ORGANISM: Arabidopsis thaliana

<400> SEQUENCE: 14
ttaagctttt aagaatctct actcacattt tctctgtgag tgttctttta tacttctttg     60
ttatttccaa ttttctttc tttcctctaa aaattttagg aactattgaa tcatttaatt    120
tctgtttgtt gataaaattt cgatcaactg ttctcggctt accgatgcat tttttgtaaa    180
accgtctttt tttggtgaat aaaattttaa attcatacaa aaaaaaaaca tatttgatac    240
tattttagct ccattgtatc tgaatcttca tttgttaatt tttttgtttc ctctgttctc    300
acttgaattt tggaatattt tctctaggtt ttaccttata ttcttcactt taagaactat    360
atgaagattt gattggaagt aataatattc ggtgatagaa tctgagtttg tttgattctg    420
gtgtggggct tatatctaac ttttttcttt gtaccaatac attttcaatt ttacattttt    480
gattagctta aaatgtgaag gataccttgt aaataactat tacactattg cttgtcttag    540
tctaatagtc ttcactaata ttttgtgcag tagaagtaaa tattataaag agttgttgtt    600
tgattataga gagttgttgt ctattcttta acttgatgtg atgttgtttt tgatgacagg    660
taaaa                                                                665

<210> SEQ ID NO 15
<211> LENGTH: 252
<212> TYPE: DNA
<213> ORGANISM: Arabidopsis thaliana

<400> SEQUENCE: 15
tctgggaaat atcgattttg atctattaag agctggtgag agccaaagtt tcctttttgt     60
ttgtttgttt gtttgtttgt tgtttgtatt tttgtatctc tgtgatcgct tctacgtgtt    120
gggtcatgca gagaaactca ttttgttttg atttgcaatg tgtcaattcc actttgaaat    180
ataagattca tcgcctctct ctcctttgtt tttttcttc ttctgcagct acgagctttg    240
ggatgtggtg ag                                                       252

<210> SEQ ID NO 16
<211> LENGTH: 186
<212> TYPE: DNA
<213> ORGANISM: Arabidopsis thaliana

<400> SEQUENCE: 16
tattcacaat ctcctgccac ctctcatttc tctagttgag ttgttatctg cgttttaag      60 cactcgaata ctgcatgcaa attccctgat tgtttgttag taccttagag attctcgatt    120
ttttagttgt ttagattgaa ccaggattac taaattgtta ttgttttctg tgtaaaggct    180
acatat                                                               186

<210> SEQ ID NO 17
<211> LENGTH: 345
<212> TYPE: DNA
<213> ORGANISM: Arabidopsis thaliana

<400> SEQUENCE: 17
```

```
ctttgcagct tctgcagcac ctctccctac tccaggtact tatgttttg ataattttat    60 tgatagactc tttacaatta tacttaagct tgttactttt tattgttacc aacaaaagct   120
aatgtatagt tcataactca caggtcctgc gtctttcggt ccgaccactt ctcctacaga   180
ttcgcaaact tctgatcctg aaggtactcg cgaactttt actgcaactt ctagttctaa    240
ctccaaaaca ttttgttcag aatttgtttc taaaagattt cgggtttgt tgacgtcaca    300 taactcgcag ggtctgcttc tttccgtccg cccacttctc cgaca                   345

<210> SEQ ID NO 18
<211> LENGTH: 285
<212> TYPE: DNA
<213> ORGANISM: Arabidopsis thaliana

<400> SEQUENCE: 18
aacaactatg gcctgagggt aacaagagta tcaggtatat gtgaaaactc tacttttgaa    60
gtttaccaaa aaaatactc tacttttgga aagacattgc tcctaaaatc ttattagttg   120
tatataattt actaaaacac atagttcttg aattcttgtt aatgagcatg ttaccttgga   180
caagtgaccc tttttctaca ttttgttttt ctatcacacg tcatgcgttt tgattgtttc   240
cttacgagtt ttaatttat tttttggtta aaaacagtaa gataa                    285

<210> SEQ ID NO 19
<211> LENGTH: 137
<212> TYPE: DNA
<213> ORGANISM: Arabidopsis thaliana

<400> SEQUENCE: 19
tctaaaaata cagggcaccg aaccaaataa aggtgagaat gatgagaagc cgtttcttac    60
tcttcattgt tttcttctct ctatccctct tcatttcctc tctgatcgcc agtgatttag   120
gcttctgcaa cgaagag                                                  137

<210> SEQ ID NO 20
<211> LENGTH: 36
<212> TYPE: DNA
<213> ORGANISM: Artificial Sequence
<220> FEATURE:
<223> OTHER INFORMATION: synthetic sequence

<400> SEQUENCE: 20
aataatggta cctggtgctt aaacactctg gtgagt                              36

<210> SEQ ID NO 21
<211> LENGTH: 38
<212> TYPE: DNA
<213> ORGANISM: Artificial Sequence
<220> FEATURE:
<223> OTHER INFORMATION: synthetic sequence

<400> SEQUENCE: 21
aataatccat ggtttgacct acaaaatcaa agcagtca                            38

<210> SEQ ID NO 22
<211> LENGTH: 34
<212> TYPE: DNA
<213> ORGANISM: Artificial Sequence
<220> FEATURE:
<223> OTHER INFORMATION: synthetic sequence

<400> SEQUENCE: 22
``` tttttttggta ccagttcttt gctttcgaag ttgc                                34

<210> SEQ ID NO 23
<211> LENGTH: 35
<212> TYPE: DNA
<213> ORGANISM: Artificial Sequence
<220> FEATURE:
<223> OTHER INFORMATION: synthetic sequence

<400> SEQUENCE: 23 tttttttccat ggtactacgt actgttttca attct                               35

<210> SEQ ID NO 24
<211> LENGTH: 37
<212> TYPE: DNA
<213> ORGANISM: Artificial Sequence
<220> FEATURE:
<223> OTHER INFORMATION: synthetic sequence

<400> SEQUENCE: 24
aaaaaaggta ccatttccac acgctttcta tcatttc                              37

<210> SEQ ID NO 25
<211> LENGTH: 42
<212> TYPE: DNA
<213> ORGANISM: Artificial Sequence
<220> FEATURE:
<223> OTHER INFORMATION: synthetic sequence

<400> SEQUENCE: 25
aaaaaaccat ggttatctct ctctaaaaaa taaaaacgaa tc                         42

<210> SEQ ID NO 26
<211> LENGTH: 33
<212> TYPE: DNA
<213> ORGANISM: Artificial Sequence
<220> FEATURE:
<223> OTHER INFORMATION: synthetic sequence

<400> SEQUENCE: 26
aataaaggta ccgtccagaa ttttctccat tga                                  33

<210> SEQ ID NO 27
<211> LENGTH: 34
<212> TYPE: DNA
<213> ORGANISM: Artificial Sequence
<220> FEATURE:
<223> OTHER INFORMATION: synthetic sequence

<400> SEQUENCE: 27
aataaaccat ggtcttcact atccaaagct ctca                                 34

<210> SEQ ID NO 28
<211> LENGTH: 37
<212> TYPE: DNA
<213> ORGANISM: Artificial Sequence
<220> FEATURE:
<223> OTHER INFORMATION: synthetic sequence

<400> SEQUENCE: 28 tttttttggta ccgtctactt tcattacagt gactctg                             37

<210> SEQ ID NO 29
<211> LENGTH: 39
<212> TYPE: DNA
<213> ORGANISM: Artificial Sequence
<220> FEATURE:
<223> OTHER INFORMATION: synthetic sequence

<400> SEQUENCE: 29 tttttccat ggttatattt tacctgcaac acaattcaa    39

<210> SEQ ID NO 30
<211> LENGTH: 32
<212> TYPE: DNA
<213> ORGANISM: Artificial Sequence
<220> FEATURE:
<223> OTHER INFORMATION: synthetic sequence

<400> SEQUENCE: 30
ttttatggta cccactcgaa tactgcatgc aa    32

<210> SEQ ID NO 31
<211> LENGTH: 38
<212> TYPE: DNA
<213> ORGANISM: Artificial Sequence
<220> FEATURE:
<223> OTHER INFORMATION: synthetic sequence

<400> SEQUENCE: 31
ttttatccat ggttatgtag cctttacaca gaaaacaa    38

<210> SEQ ID NO 32
<211> LENGTH: 32
<212> TYPE: DNA
<213> ORGANISM: Artificial Sequence
<220> FEATURE:
<223> OTHER INFORMATION: synthetic sequence

<400> SEQUENCE: 32
tatataggta ccaacaacta tggcctgagg gt    32

<210> SEQ ID NO 33
<211> LENGTH: 44
<212> TYPE: DNA
<213> ORGANISM: Artificial Sequence
<220> FEATURE:
<223> OTHER INFORMATION: synthetic sequence

<400> SEQUENCE: 33
tatataccat ggttatctta ctgtttttaa ccaaaaaata aaat    44

<210> SEQ ID NO 34
<211> LENGTH: 36
<212> TYPE: DNA
<213> ORGANISM: Artificial Sequence
<220> FEATURE:
<223> OTHER INFORMATION: synthetic sequence

<400> SEQUENCE: 34 ttttaggta ccatcttagg gtttcgcgag atctca    36

<210> SEQ ID NO 35
<211> LENGTH: 42
<212> TYPE: DNA
<213> ORGANISM: Artificial Sequence
<220> FEATURE:
<223> OTHER INFORMATION: synthetic sequence

<400> SEQUENCE: 35 tttttccat ggtgctaagc tatctctgtt aatataaaat tg    42

<210> SEQ ID NO 36
<211> LENGTH: 34
<212> TYPE: DNA
<213> ORGANISM: Artificial Sequence
<220> FEATURE:
<223> OTHER INFORMATION: synthetic sequence

<400> SEQUENCE: 36 tttttggta ccattttgt tggtgaaagg taga         34

<210> SEQ ID NO 37
<211> LENGTH: 37
<212> TYPE: DNA
<213> ORGANISM: Artificial Sequence
<220> FEATURE:
<223> OTHER INFORMATION: synthetic sequence

<400> SEQUENCE: 37
tttttaccat ggttacgttt ttgtctctgc ttcttct         37

<210> SEQ ID NO 38
<211> LENGTH: 36
<212> TYPE: DNA
<213> ORGANISM: Artificial Sequence
<220> FEATURE:
<223> OTHER INFORMATION: synthetic sequence

<400> SEQUENCE: 38
tatattggta cctctgggaa atatcgattt tgatct         36

<210> SEQ ID NO 39
<211> LENGTH: 33
<212> TYPE: DNA
<213> ORGANISM: Artificial Sequence
<220> FEATURE:
<223> OTHER INFORMATION: synthetic sequence

<400> SEQUENCE: 39
tatataccat ggtctcacca catcccaaag ctc         33

<210> SEQ ID NO 40
<211> LENGTH: 35
<212> TYPE: DNA
<213> ORGANISM: Artificial Sequence
<220> FEATURE:
<223> OTHER INFORMATION: synthetic sequence

<400> SEQUENCE: 40
ttttatggta ccgcacaatc ttagcttacc ttgaa         35

<210> SEQ ID NO 41
<211> LENGTH: 37
<212> TYPE: DNA
<213> ORGANISM: Artificial Sequence
<220> FEATURE:
<223> OTHER INFORMATION: synthetic sequence

<400> SEQUENCE: 41
ttttatccat ggttatttaa tccacaagcc ttgcctc         37

<210> SEQ ID NO 42
<211> LENGTH: 29
<212> TYPE: DNA
<213> ORGANISM: Artificial Sequence
<220> FEATURE:
<223> OTHER INFORMATION: synthetic sequence

```
<400> SEQUENCE: 42
tttttaccat ggtgtcggag aagtgggcg                                              29

<210> SEQ ID NO 43
<211> LENGTH: 27
<212> TYPE: DNA
<213> ORGANISM: Artificial Sequence
<220> FEATURE:
<223> OTHER INFORMATION: synthetic sequence

<400> SEQUENCE: 43
tttttaccat ggagaagtgg gcggacg                                                27

<210> SEQ ID NO 44
<211> LENGTH: 37
<212> TYPE: DNA
<213> ORGANISM: Artificial Sequence
<220> FEATURE:
<223> OTHER INFORMATION: synthetic sequence

<400> SEQUENCE: 44
ttttatggta cctagcttaa tctcagattc gaatcgt                                     37

<210> SEQ ID NO 45
<211> LENGTH: 40
<212> TYPE: DNA
<213> ORGANISM: Artificial Sequence
<220> FEATURE:
<223> OTHER INFORMATION: synthetic sequence

<400> SEQUENCE: 45
ttttatccat ggtagtatct acataccaat catacaaatg                                  40

<210> SEQ ID NO 46
<211> LENGTH: 32
<212> TYPE: DNA
<213> ORGANISM: Artificial Sequence
<220> FEATURE:
<223> OTHER INFORMATION: synthetic sequence

<400> SEQUENCE: 46 tttttttggta cctttcacga tttggaattt ga                                         32

<210> SEQ ID NO 47
<211> LENGTH: 36
<212> TYPE: DNA
<213> ORGANISM: Artificial Sequence
<220> FEATURE:
<223> OTHER INFORMATION: synthetic sequence

<400> SEQUENCE: 47 tttttttccat ggtctacaac attaaaacga ccatta                                     36

<210> SEQ ID NO 48
<211> LENGTH: 32
<212> TYPE: DNA
<213> ORGANISM: Artificial Sequence
<220> FEATURE:
<223> OTHER INFORMATION: synthetic sequence

<400> SEQUENCE: 48
tatataggta ccagggtttc gttttttgttt ca                                         32

<210> SEQ ID NO 49
```

```
<211> LENGTH: 35
<212> TYPE: DNA
<213> ORGANISM: Artificial Sequence
<220> FEATURE:
<223> OTHER INFORMATION: synthetic sequence

<400> SEQUENCE: 49
tatataccat ggttatctcc tgctcaaaga aacca                              35

<210> SEQ ID NO 50
<211> LENGTH: 33
<212> TYPE: DNA
<213> ORGANISM: Artificial Sequence
<220> FEATURE:
<223> OTHER INFORMATION: synthetic sequence

<400> SEQUENCE: 50
tttataggta ccagaagctc atttcttcga tac                                33

<210> SEQ ID NO 51
<211> LENGTH: 32
<212> TYPE: DNA
<213> ORGANISM: Artificial Sequence
<220> FEATURE:
<223> OTHER INFORMATION: synthetic sequence

<400> SEQUENCE: 51
tttataccat ggtctctgcg caaaaattca cc                                 32

<210> SEQ ID NO 52
<211> LENGTH: 31
<212> TYPE: DNA
<213> ORGANISM: Artificial Sequence
<220> FEATURE:
<223> OTHER INFORMATION: synthetic sequence

<400> SEQUENCE: 52
tatattggta cctctaaaaa tacagggcac c                                  31

<210> SEQ ID NO 53
<211> LENGTH: 35
<212> TYPE: DNA
<213> ORGANISM: Artificial Sequence
<220> FEATURE:
<223> OTHER INFORMATION: synthetic sequence

<400> SEQUENCE: 53
tatattccat ggttactctt cgttgcagaa gccta                              35

<210> SEQ ID NO 54
<211> LENGTH: 33
<212> TYPE: DNA
<213> ORGANISM: Artificial Sequence
<220> FEATURE:
<223> OTHER INFORMATION: synthetic sequence

<400> SEQUENCE: 54
tatataggta ccactgttta agcttcactg tct                                33

<210> SEQ ID NO 55
<211> LENGTH: 32
<212> TYPE: DNA
<213> ORGANISM: Artificial Sequence
<220> FEATURE:
<223> OTHER INFORMATION: synthetic sequence

<400> SEQUENCE: 55
```

```
tatataccat ggtttcttct aaagctgaaa gt                                    32
```

<210> SEQ ID NO 56
<211> LENGTH: 39
<212> TYPE: DNA
<213> ORGANISM: Artificial Sequence
<220> FEATURE:
<223> OTHER INFORMATION: synthetic sequence

<400> SEQUENCE: 56

```
tatataggta ccttaagctt ttaagaatct ctactcaca                             39
```

<210> SEQ ID NO 57
<211> LENGTH: 41
<212> TYPE: DNA
<213> ORGANISM: Artificial Sequence
<220> FEATURE:
<223> OTHER INFORMATION: synthetic sequence

<400> SEQUENCE: 57

```
atatatccat ggttaaattt tacctgtcat caaaaacaac a                          41
```

<210> SEQ ID NO 58
<211> LENGTH: 49
<212> TYPE: DNA
<213> ORGANISM: Artificial Sequence
<220> FEATURE:
<223> OTHER INFORMATION: synthetic sequence

<400> SEQUENCE: 58

```
ggggacaact ttgtatagaa aagttggcca catcatgttt agacttatc                  49
```

<210> SEQ ID NO 59
<211> LENGTH: 50
<212> TYPE: DNA
<213> ORGANISM: Artificial Sequence
<220> FEATURE:
<223> OTHER INFORMATION: synthetic sequence

<400> SEQUENCE: 59

```
ggggactgct tttttgtaca aacttgttta ccttttatat ttatatatag                 50
```

<210> SEQ ID NO 60
<211> LENGTH: 73
<212> TYPE: DNA
<213> ORGANISM: Artificial Sequence
<220> FEATURE:
<223> OTHER INFORMATION: synthetic sequence

<400> SEQUENCE: 60

```
ggtacccggg gatcctctag catatgctcg aggcggccgc agatatcaga tctggtcgac      60
ggcatgcaag ctt                                                         73
```

<210> SEQ ID NO 61
<211> LENGTH: 12197
<212> TYPE: DNA
<213> ORGANISM: Artificial Sequence
<220> FEATURE:
<223> OTHER INFORMATION: vector sequence

<400> SEQUENCE: 61

```
gacatacaaa tggacgaacg gataaacctt ttcacgccct tttaaatatc cgattattct      60
aataaacgct cttttctctt aggtttaccc gccaatatat cctgtcaaac actgatagtt     120
```

```
taaactgaag gcgggaaacg acaatcagat ctagtaggaa acagctatga ccatgattac    180
gccaagctat cgattacgcc aagctatcaa ctttgtatag aaaagttggc cacatcatgt    240
ttagacttat ctccataaag aaaaccactc atcaaagcta atacaaaagc tctagtgtga    300
cacttcaacg tcacttcatc aggatcagca ggtaaattcc gaaaattctc acgcagccac    360
gctaaggaca catgagaacc atgaagatcc ttgggacctg cctatgacc aagcaaatcc     420 tcacataaat cagcccagtt gtattttgta ctaccagtta ctgcaggtcc atcgacacgt    480
agacccaaca aaatattcac atcttgtaaa gtcacagtga tctctccagc aggaagatga    540
aaagtatgcg tttcgggtct ccatctctcc accaaagctg ttatcagagc ataatcaagt    600
tgtataaagg caaccttgta aactccatat agaccaaact ctatcaactt ttgacacacg    660
agaggatcca gaggccaatc tcgcatcccc aataacttgt gccgacatgt cagttcacga    720
ggaggaacct gaatgtgaag tataacggta aaaaggaaat aattaaaaca acggaagcaa    780
aacaagaaac aagatgaaat gagaaactag taacacacct catcttccca tatagcagct    840
gatctatgct catgttgcca caccaatata gattgatcaa ctggaccagg atccaaatca    900
aagtttaata gactttgcac ctccatctat ataatatatc acaggacaat aaacacaatg    960
atcagtgatt atacaacatc aaagaaaact tgtaattctg ggaatataac tgagaaatga   1020
gaattaaaga ttcataattt gaacacaaga atcctaaac tggtacgaaa gaaaaattgc    1080
tcaacaaaaa aatcaagcta attactcgta tacaaagaca cgaagaacta atacaagaaa   1140
caagaaacaa caaaccacaa agagattgaa ccaatccaaa ttcgacaaca taaaccaagt   1200
gtgtgggtga ttggaatcag aggacgtacc aaagaaaagc gtccgtgatc aacaaaaacc   1260
aaaaagagac gtttgaaata aaccagagga agacgaagaa taattaagca aagagaagcg   1320
ttaagcggga gcgagaaagg aaacgagaga agagagagc ttccagatcc gacagaagtt    1380
ttcggcttct tcttttttcgt ttaagaactt ctgatcctcc taggtctgtc cgaagaacta   1440 atcttttga ggtaacgacg ccgttttttct caaaacatgg gcccattaac catagtctcg   1500
gcccaaacga aacttaatac gacaatgttt gggtgtaaac gcaagatttt tgtcgattat   1560
cacaagtaaa aaaataaata caaacacttg agtctctcta gacatcgtgc atcgccttag   1620
ctttaagttt tttctcgaaa caaaagagtt atttttatttg aactttgaag attatacgaa   1680
gacacgtggc gtgaacccaa ttcataacaa cgccacgcta tactctttttg catgcacctc   1740 aatttgaaca tcatcaagtc tctctctctt tttctgactt tgatccacga acctaaccag   1800
cttgcgatct ctatttaatc ggtcctcgac gcaacttcaa cttctactac atccattcac   1860
atcaaatcaa tacagaaagt ttttttctata tataaatata aaggtaaac aagtttgtac    1920 aaaaaagcag gctggtacct ggtgcttaaa cactctggtg agttctagta cttctgctat   1980
gatcgatctc attaccatt cttaaatttc tctccctaaa tattccgagt tcttgatttt    2040
tgataacttc aggttttctc ttttttgataa atctggtctt ccatttttt tttttttgtg    2100 gttaatttag tttcctatgt tcttcgattg tattatgcat gatctgtgtt tggattctgt   2160
tagattatgt attggtgaat atgtatgtgt ttttgcatgt ctggttttgg tcttaaaaat   2220
gttcaaatct gatgatttga ttgaagcttt tttagtgttg gtttgattct tctcaaaact   2280
actgttaatt tactatcatg ttttccaact ttgattcatg atgacacttt tgttctgctt   2340
tgttataaaa ttttggttgg tttgattttg taattatagt gtaattttgt taggaatgaa   2400
catgttttaa tactctgttt tcgatttgtc acacattcga attattaatc gataatttaa   2460
ctgaaaattc atggttctag atcttgttgt catcagatta tttgtttcga taattcatca   2520
```

```
aatatgtagt ccttttgctg atttgcgact gtttcatttt ttctcaaaat tgttttttgt   2580
taagtttatc taacagttat cgttgtcaaa agtctctttc attttgcaaa atcttctttt   2640 ttttttttgtt tgtaactttg tttttttaagc tacacattta gtctgtaaaa tagcatcgag   2700
gaacagttgt cttagtagac ttgcatgttc ttgtaacttc tatttgtttc agtttgttga   2760
tgactgcttt gattttgtag gtcaaaccat ggaagacgcc aaaaacataa agaaaggccc   2820
ggcgccattc tatccgctgg aagatggaac cgctggagag caactgcata aggctatgaa   2880
gagatacgcc ctggttcctg gaacaattgc ttttacagat gcacatatcg aggtggacat   2940
cacttacgct gagtacttcg aaatgtccgt tcggttggca gaagctatga acgatatgg    3000 gctgaataca aatcacagaa tcgtcgtatg cagtgaaaac tctcttcaat tctttatgcc   3060
ggtgttgggc gcgttattta tcggagttgc agttgcgccc gcgaacgaca tttataatga   3120
acgtgaattg ctcaacagta tgggcatttc gcagcctacc gtggtgttcg tttccaaaaa   3180
ggggttgcaa aaattttga acgtgcaaaa aaagctccca atcatccaaa aaattattat    3240
catggattct aaaacggatt accagggatt tcagtcgatg tacacgttcg tcacatctca   3300
tctacctccc ggttttaatg aatacgattt tgtgccagag tccttcgata gggacaagac   3360
aattgcactg atcatgaact cctctggatc tactggtctg cctaaaggtg tcgctctgcc   3420
tcatagaact gcctgcgtga gattctcgca tgccagagat cctattttg gcaatcaaat    3480 cattccggat actgcgattt taagtgttgt tccattccat cacggttttg gaatgtttac   3540
tacactcgga tatttgatat gtggatttcg agtcgtctta atgtatagat ttgaagaaga   3600
gctgtttctg aggagccttc aggattacaa gattcaaagt gcgctgctgg tgccaaccct   3660
attctccttc ttcgccaaaa gcactctgat tgacaaatac gatttatcta atttacacga   3720
aattgcttct ggtggcgctc ccctctctaa ggaagtcggg gaagcggttg ccaagaggtt   3780
ccatctgcca ggtatcaggc aaggatatgg gctcactgag actacatcag ctattctgat   3840
tacacccgag gggatgata aaccgggcgc ggtcggtaaa gttgttccat tttttgaagc     3900
gaaggttgtg gatctggata ccgggaaaac gctgggcgtt aatcaaagag gcgaactgtg   3960
tgtgagaggt cctatgatta tgtccggtta tgtaaacaat ccggaagcga ccaacgcctt   4020
gattgacaag gatggatggc tacattctgg agacatagct tactgggacg aagacgaaca   4080
cttcttcatc gttgaccgcc tgaagtctct gattaagtac aaaggctatc aggtggctcc   4140
cgctgaattg gaatccatct tgctccaaca ccccaacatc ttcgacgcag gtgtcgcagg   4200
tcttcccgac gatgacgccg gtgaacttcc cgccgccgtt gttgttttgg agcacggaaa   4260
gacgatgacg gaaaagagaa tcgtggatta cgtcgccagt caagtaacaa ccgcgaaaaa   4320
gttgcgcgga ggagttgtgt ttgtggacga agtaccgaaa ggtcttaccg gaaaactcga   4380
cgcaagaaaa atcagagaga tcctcataaa ggccaagaag ggcggaaaga tcgccgtgta   4440
actcgagcat atgggctcga atttccccga tcgttcaaac atttggcaat aaagtttctt   4500
aagattgaat cctgttgccg gtcttgcgat gattatcata taatttctgt tgaattacgt   4560
taagcatgta ataattaaca tgtaatgcat gacgttattt atgagatggg ttttatgat    4620 tagagtcccg caattataca tttaatacgc gatagaaaac aaaatatagc gcgcaaacta   4680
ggataaatta tcgcgcgcgg tgtcatctat gttactagat cgggaattca agcttggcgt   4740
aatcatggac ccagctttct tgtacaaagt ggggtacccg gggatcctct agcatatgct   4800
cgaggcggcc gcagatatca gatctggtcg acggcatgca agcttggcgt aatcatggca   4860
```

```
actttattat acatagttga taattcactg gccggataat tcactggccg tcgttttaca   4920
acgactcagg atcctgtcaa acactgatag tttaaactga aggcgggaaa cgacaatctg   4980
atcatgagcg gagaattaag ggagtcacgt tatgaccccc gccgatgacg cgggacaagc   5040
cgttttacgt ttggaactga cagaaccgca acgttgaagg agccactcag ccgcgggttt   5100
ctggagttta atgagctaag cacatacgtc agaaaccatt attgcgcgtt caaaagtcgc   5160
ctaaggtcac tatcagctag caaatatttc ttgtcaaaaa tgctccactg acgttccata   5220
aattcccctc ggtatccaat tagagtctca tattcactct caatccaaat aatctgcacc   5280
ggatctggat cgtttcgcat gattgaacaa gatggattgc acgcaggttc tccggccgct   5340
tgggtggaga ggctattcgg ctatgactgg gcacaacaga caatcggctg ctctgatgcc   5400
gccgtgttcc ggctgtcagc gcaggggcgc ccggttcttt ttgtcaagac cgacctgtcc   5460
ggtgccctga atgaactgca ggacgaggca gcgcggctat cgtggctggc cacgacgggc   5520
gttccttgcg cagctgtgct cgacgttgtc actgaagcgg gaagggactg gctgctattg   5580
ggcgaagtgc cggggcagga tctcctgtca tctcaccttg ctcctgccga gaaagtatcc   5640
atcatggctg atgcaatgcg gcggctgcat acgcttgatc cggctacctg cccattcgac   5700
caccaagcga aacatcgcat cgagcgagca cgtactcgga tggaagccgg tcttgtcgat   5760
caggatgatc tggacgaaga gcatcagggg ctcgcgccag ccgaactgtt cgccaggctc   5820
aaggcgcgca tgcccgacgg cgaggatctc gtcgtgaccc atggcgatgc ctgcttgccg   5880
aatatcatgg tggaaaatgg ccgcttttct ggattcatcg actgtggccg ctgggtgtg    5940
gcggaccgct atcaggacat agcgttggct acccgtgata ttgctgaaga gcttggcggc   6000
gaatgggctg accgcttcct cgtgctttac ggtatcgccg ctcccgattc gcagcgcatc   6060
gccttctatc gccttcttga cgagttcttc tgagcgggac ccaagctcta gatcttgctg   6120
cgttcggata ttttcgtgga gttcccgcca cagacccgga tgatcccga tcgttcaaac   6180
atttggcaat aaagtttctt aagattgaat cctgttgccg gtcttgcgat gattatcata   6240
taatttctgt tgaattacgt taagcatgta ataattaaca tgtaatgcat gacgttattt   6300
atgagatggg ttttttatgat tagagtcccg caattataca tttaatacgc gatagaaaac   6360
aaaatatagc gcgcaaacta ggataaatta tcgcgcgcgg tgtcatctat gttactagat   6420
cgggcctcct gtcaagctct gcttggtaat aattgtcatt agattgtttt tatgcataga   6480
tgcactcgaa atcagccaat tttagacaag tatcaaacgg atgttaattc agtacattaa   6540
agacgtccgc aatgtgttat taagttgtct aagcgtcaat ttgtttacac cacaatatat   6600
cctgccacca gccagccaac agctccccga ccggcagctc ggcacaaaat caccacgcgt   6660
taccaccacg ccggccggcc gcatggtgtt gaccgtgttc gccggcattg ccgagttcga   6720
gcgttcccta atcatcgacc gcacccggag cgggcgcgag gccgccaagg cccgaggcgt   6780
gaagtttggc ccccgcccta ccctcacccc ggcacagatc gcgcacgccc gcgagctgat   6840
cgaccaggaa ggccgcaccg tgaaagaggc ggctgcactg cttggcgtgc atcgctcgac   6900
cctgtaccgc gcacttgagc gcagcgagga agtgacgccc accgaggcca ggcggcgcgg   6960
tgccttccgt gaggacgcat tgaccgaggc cgacgccctg gcggccgccg agaatgaacg   7020
ccaagaggaa caagcatgaa accgcaccag gacggccagg acgaaccgtt tttcattacc   7080
gaagagatcg aggcggagat gatcgcggcc gggtacgtgt tcgagccgcc gcgcacgtc    7140
tcaaccgtgc ggctgcatga aatcctggcc ggtttgtctg atgccaagct ggcggcctgg   7200
ccggccagct tggccgctga agaaaccgag cgccgccgtc taaaaaggtg atgtgtattt   7260
```

```
gagtaaaaca gcttgcgtca tgcggtcgct gcgtatatga tgcgatgagt aaataaacaa   7320
atacgcaagg ggaacgcatg aaggttatcg ctgtacttaa ccagaaaggc gggtcaggca   7380
agacgaccat cgcaacccat ctagcccgcg ccctgcaact cgccggggcc gatgttctgt   7440
tagtcgattc cgatcoccag ggcagtgccc gcgattgggc ggccgtgcgg gaagatcaac   7500
cgctaaccgt tgtcggcatc gaccgcccga cgattgaccg cgacgtgaag gccatcggcc   7560
ggcgcgactt cgtagtgatc gacggagcgc cccaggcggc ggacttggct gtgtccgcga   7620
tcaaggcagc cgacttcgtg ctgattccgg tgcagccaag cccttacgac atatgggcca   7680
ccgccgacct ggtggagctg gttaagcagc gcattgaggt cacggatgga aggctacaag   7740
cggcctttgt cgtgtcgcgg gcgatcaaag gcacgcgcat cggcggtgag gttgccgagg   7800
cgctggccgg gtacgagctg cccattcttg agtcccgtat cacgcagcgc gtgagctacc   7860
caggcactgc cgccgccggc acaaccgttc ttgaatcaga acccgagggc gacgctgccc   7920
gcgaggtcca ggcgctggcc gctgaaatta aatcaaaact catttgagtt aatgaggtaa   7980
agagaaaatg agcaaaagca caaacacgct aagtgccggc cgtccgagcg cacgcagcag   8040
caaggctgca acgttggcca gcctggcaga cacgccagcc atgaagcggg tcaactttca   8100
gttgccggcg gaggatcaca ccaagctgaa gatgtacgcg gtacgccaag gcaagaccat   8160
taccgagctg ctatctgaat acatcgcgca gctaccagag taaatgagca atgaataaa   8220 tgagtagatg aattttagcg gctaaaggag gcggcatgga aaatcaagaa caaccaggca   8280
ccgacgccgt ggaatgcccc atgtgtggag gaacgggcgg ttggccaggc gtaagcggct   8340
gggttgtctg ccggccctgc aatggcactg gaacccccaa gcccgaggaa tcggcgtgag   8400
cggtcgcaaa ccatccggcc cggtacaaat cggcgcggcg ctgggtgatg acctggtgga   8460
gaagttgaag gccgcgcagg ccgcccagcg gcaacgcatc gaggcagaag cacgccccgg   8520
tgaatcgtgg caagcggccg ctgatcgaat ccgcaaagaa tcccggcaac cgccggcagc   8580
cggtcgcccg tcgattagga agccgcccaa gggcgacgag caaccagatt ttttcgttcc   8640
gatgctctat gacgtgggca cccgcgatag tcgcagcatc atggacgtgg ccgttttccg   8700
tctgtcgaag cgtgaccgac gagctggcga ggtgatccgc tacgagcttc agacgggca   8760 cgtagaggtt tccgcagggc cggccggcat ggccagtgtg tgggattacg acctggtact   8820 gatgcggtt tcccatctaa ccgaatccat gaaccgatac cgggaaggga agggagacaa   8880
gcccggccgc gtgttccgtc acacgttgc ggacgtactc aagttctgcc ggcgagccga   8940
tggcggaaag cagaaagacg acctggtaga aacctgcatt cggttaaaca ccacgcacgt   9000
tgccatgcag cgtacgaaga aggccaagaa cggccgcctg gtgacggtat ccgagggtga   9060
agccttgatt agccgctaca agatcgtaaa gagcgaaacc gggcggccgg agtacatcga   9120
gatcgagcta gctgattgga tgtaccgcga gatcacagaa ggcaagaacc cggacgtgct   9180
gacggttcac cccgattact ttttgatcga tcccggcatc ggccgttttc tctaccgcct   9240
ggcacgccgc gccgcaggca aggcagaagc cagatggttg ttcaagacga tctacgaacg   9300
cagtggcagc gccggagagt tcaagaagtt ctgtttcacc gtgcgcaagc tgatcgggtc   9360
aaatgacctg ccggagtacg atttgaagga ggaggcgggg caggctggcc cgatcctagt   9420
catgcgctac cgcaacctga tcgagggcga agcatccgcc ggttcctaat gtacggagca   9480
gatgctaggg caaattgccc tagcagggga aaaggtcga aaaggtctct ttcctgtgga   9540
tagcacgtac attgggaacc caaagccgta cattgggaac cggaacccgt acattgggaa   9600
```

-continued

```
cccaaagccg tacattggga accggtcaca catgtaagtg actgatataa aagagaaaaa   9660
aggcgatttt tccgcctaaa actctttaaa acttattaaa actcttaaaa cccgcctggc   9720
ctgtgcataa ctgtctggcc agcgcacagc cgaagagctg caaaaagcgc ctacccttcg   9780
gtcgctgcgc tccctacgcc ccgccgcttc gcgtcggcct atcgcggccg ctggccgctc   9840
aaaaatggct ggcctacggc caggcaatct accagggcgc ggacaagccg cgccgtcgcc   9900
actcgaccgc cggcgcccac atcaaggcac cctgcctcgc gcgtttcggt gatgacggtg   9960
aaaacctctg acacatgcag ctcccggaga cggtcacagc ttgtctgtaa gcggatgccg  10020
ggagcagaca agcccgtcag ggcgcgtcag cgggtgttgg cgggtgtcgg ggcgcagcca  10080
tgacccagtc acgtagcgat agcggagtgt atactggctt aactatgcgg catcagagca  10140
gattgtactg agagtgcacc atatgcggtg tgaaataccg cacagatgcg taaggagaaa  10200
ataccgcatc aggcgctctt ccgcttcctc gctcactgac tcgctgcgct cggtcgttcg  10260
gctgcggcga gcggtatcag ctcactcaaa ggcggtaata cggttatcca cagaatcagg  10320
ggataacgca ggaaagaaca tgtgagcaaa aggccagcaa aaggccagga accgtaaaaa  10380
ggccgcgttg ctggcgtttt tccataggct ccgcccccct gacgagcatc acaaaaatcg  10440
acgctcaagt cagaggtggc gaaacccgac aggactataa agataccagg cgtttccccc  10500
tggaagctcc ctcgtgcgct ctcctgttcc gaccctgccg cttaccggat acctgtccgc  10560
ctttctccct tcgggaagcg tggcgctttc tcatagctca cgctgtaggt atctcagttc  10620
ggtgtaggtc gttcgctcca agctgggctg tgtgcacgaa ccccccgttc agcccgaccg  10680
ctgcgcctta tccggtaact atcgtcttga gtccaacccg gtaagacacg acttatcgcc  10740
actggcagca gccactggta acaggattag cagagcgagg tatgtaggcg gtgctacaga  10800
gttcttgaag tggtggccta actacggcta cactagaagg acagtatttg gtatctgcgc  10860
tctgctgaag ccagttacct tcggaaaaag agttggtagc tcttgatccg gcaaacaaac  10920
caccgctggt agcggtggtt tttttgtttg caagcagcag attacgcgca gaaaaaaagg  10980
atctcaagaa gatcctttga tcttttctac ggggtctgac gctcagtgga acgaaaactc  11040
acgttaaggg attttggtca tgcatgatat atctcccaat ttgtgtaggg cttattatgc  11100
acgcttaaaa ataataaaag cagacttgac ctgatagttt ggctgtgagc aattatgtgc  11160
ttagtgcatc taacgcttga gttaagccgc gccgcgaagc ggcgtcggct tgaacgaatt  11220
tctagctaga cattatttgc cgactacctt ggtgatctcg cctttcacgt agtggacaaa  11280
ttcttccaac tgatctgcgc gcgaggccaa gcgatcttct tcttgtccaa gataagcctg  11340
tctagcttca agtatgacgg gctgatactg ggccggcagg cgctccattg cccagtcggc  11400
agcgacatcc ttcggcgcga ttttgccggt tactgcgctg taccaaatgc gggacaacgt  11460
aagcactaca tttcgctcat cgccagccca gtcgggcggc gagttccata gcgttaaggt  11520
ttcatttagc gcctcaaata gatcctgttc aggaaccgga tcaaagagtt cctccgccgc  11580
tggacctacc aaggcaacgc tatgttctct tgcttttgtc agcaagatag ccagatcaat  11640
gtcgatcgtg gctggctcga agatacctgc aagaatgtca ttgcgctgcc attctccaaa  11700
ttgcagttcg cgcttagctg gataacgcca cggaatgatg tcgtcgtgca caacaatggt  11760
gacttctaca gcgcggagaa tctcgctctc tccaggggaa gccgaagttt ccaaaaggtc  11820
gttgatcaaa gctcgccgcg ttgtttcatc aagccttacg gtcaccgtaa ccagcaaatc  11880
aatatcactg tgtggcttca ggccgccatc cactgcggag ccgtacaaat gtacggccag  11940
caacgtcggt tcgagatggc gctcgatgac gccaactacc tctgatagtt gagtcgatac  12000
```

```
ttcggcgatc accgcttccc ccatgatgtt taactttgtt ttagggcgac tgccctgctg    12060
cgtaacatcg ttgctgctcc ataacatcaa acatcgaccc acggcgtaac gcgcttgctg    12120
cttggatgcc cgaggcatag actgtacccc aaaaaaacag tcataacaag ccatgaaaac    12180
cgccactgcg ttccatg                                                   12197

<210> SEQ ID NO 62
<211> LENGTH: 14901
<212> TYPE: DNA
<213> ORGANISM: Artificial Sequence
<220> FEATURE:
<223> OTHER INFORMATION: vector sequence

<400> SEQUENCE: 62
gacatacaaa tggacgaacg gataaacctt ttcacgccct tttaaatatc cgattattct      60
aataaacgct cttttctctt aggtttaccc gccaatatat cctgtcaaac actgatagtt     120
taaactgaag gcgggaaacg acaatcagat ctagtaggaa acagctatga ccatgattac     180
gccaagctat cgattacgcc aagctatcaa ctttgtatag aaaagttggc cacatcatgt     240
ttagacttat ctccataaag aaaaccactc atcaaagcta atacaaaagc tctagtgtga     300
cacttcaacg tcacttcatc aggatcagca ggtaaattcc gaaaattctc acgcagccac     360
gctaaggaca catgagaacc atgaagatcc ttgggacctg gcctatgacc aagcaaatcc     420
tcacataaat cagcccagtt gtattttgta ctaccagtta ctgcaggtcc atcgacacgt     480
agacccaaca aaatattcac atcttgtaaa gtcacagtga tctctccagc aggaagatga     540
aaagtatgcg tttcgggtct ccatctctcc accaaagctg ttatcagagc ataatcaagt     600
tgtataaagg caaccttgta aactccatat agaccaaact ctatcaactt ttgacacacg     660
agaggatcca gaggccaatc tcgcatcccc aataacttgt gccgacatgt cagttcacga     720
ggaggaacct gaatgtgaag tataacggta aaaaggaaat aattaaaaca acggaagcaa     780
aacaagaaac aagatgaaat gagaaactag taacacacct catcttccca tatagcagct     840
gatctatgct catgttgcca caccaatata gattgatcaa ctggaccagg atccaaatca     900
aagtttaata gactttgcac ctccatctat ataatatatc acaggacaat aaacacaatg     960
atcagtgatt atacaacatc aaagaaaact tgtaattctg ggaatataac tgagaaatga    1020
gaattaaaga ttcataattt gaacacaaga atcctaaaac tggtacgaaa gaaaaattgc    1080
tcaacaaaaa aatcaagcta attactcgta tacaaagaca cgaagaacta atacaagaaa    1140
caagaaacaa caaaccacaa agagattgaa ccaatccaaa ttcgacaaca taaccaagt    1200 gtgtgggtga ttggaatcag aggacgtacc aaagaaaagc gtccgtgatc aacaaaaacc    1260
aaaaagagac gtttgaaata aaccagagga agacgaagaa taattaagca agagaagcg    1320 ttaagcggga gcgagaaagg aaacgagaga agagagagc ttccagatcc gacagaagtt    1380
ttcggcttct tctttttcgt ttaagaactt ctgatcctcc taggtctgtc cgaagaacta    1440 atcttttga ggtaacgacg ccgttttttct caaaacatgg gcccattaac catagtctcg    1500
gcccaaacga aacttaatac gacaatgttt gggtgtaaac gcaaagattt tgtcgattat    1560
cacaagtaaa aaaataaata caaacacttg agtctctcta gacatcgtgc atcgccttag    1620
ctttaagttt tttctcgaaa caaagagtt atttatttg aactttgaag attatacgaa    1680
gacacgtggc gtgaacccaa ttcataacaa cgccacgcta tactcttttg catgcacctc    1740
aatttgaaca tcatcaagtc tctctctctt tttctgactt tgatccacga acctaaccag    1800
```

```
cttgcgatct ctatttaatc ggtcctcgac gcaacttcaa cttctactac atccattcac    1860
atcaaatcaa tacagaaagt tttttctata tataaatata aaaggtaaac aagtttgtac    1920
aaaaaagcag gctggtacct ggtgcttaaa cactctggtg agttctagta cttctgctat    1980
gatcgatctc attaccattt cttaaatttc tctccctaaa tattccgagt tcttgatttt    2040
tgataacttc aggttttctc ttttgataa atctggtctt tccattttt ttttttgtg       2100 gttaatttag tttcctatgt tcttcgattg tattatgcat gatctgtgtt tggattctgt    2160
tagattatgt attggtgaat atgtatgtgt ttttgcatgt ctggttttgg tcttaaaaat    2220
gttcaaatct gatgatttga ttgaagcttt tttagtgttg gtttgattct tctcaaaact    2280
actgttaatt tactatcatg ttttccaact ttgattcatg atgacactt  tgttctgctt    2340 tgttataaaa ttttggttgg tttgattttg taattatagt gtaattttgt taggaatgaa    2400
catgttttaa tactctgttt tcgatttgtc acacattcga attattaatc gataatttaa    2460
ctgaaaattc atggttctag atcttgttgt catcagatta tttgtttcga taattcatca    2520
aatatgtagt cctttgctg atttgcgact gtttcattt ttctcaaaat tgttttttgt      2580
taagtttatc taacagttat cgttgtcaaa agtctctttc attttgcaaa atcttctttt    2640
tttttttgtt tgtaacttg tttttaagc tacacattta gtctgtaaaa tagcatcgag      2700
gaacagttgt cttagtagac ttgcatgttc ttgtaacttc tatttgtttc agtttgttga    2760
tgactgcttt gattttgtag gtcaaaccat ggaagacgcc aaaaacataa agaaaggccc    2820
ggcgccattc tatccgctgg aagatggaac cgctggagag caactgcata aggctatgaa    2880
gagatacgcc ctggttcctg gaacaattgc ttttacagat gcacatatcg aggtggacat    2940
cacttacgct gagtacttcg aaatgtccgt tcggttggca gaagctatga acgatatgg    3000 gctgaataca aatcacagaa tcgtcgtatg cagtgaaaac tctcttcaat tctttatgcc    3060
ggtgttgggc gcgttatta tcggagttgc agttgcgccc gcgaacgaca tttataatga    3120
acgtgaattg ctcaacagta tgggcatttc gcagcctacc gtggtgttcg tttccaaaaa    3180
ggggttgcaa aaaattttga acgtgcaaaa aaagctccca atcatccaaa aaattattat    3240
catggattct aaaacggatt accagggatt tcagtcgatg tacacgttcg tcacatctca    3300
tctacctccc ggttttaatg aatacgattt tgtgccagag tccttcgata gggacaagac    3360
aattgcactg atcatgaact cctctggatc tactggtctg cctaaaggtg tcgctctgcc    3420
tcatagaact gcctgcgtga gattctcgca tgccagagat cctatttttg gcaatcaaat    3480
cattccggat actgcgattt taagtgttgt tccattccat cacggttttg gaatgtttac    3540
tacactcgga tatttgatat gtggatttcg agtcgtctta atgtatagat ttgaagaaga    3600
gctgtttctg aggagccttc aggattacaa gattcaaagt gcgctgctgg tgccaaccct    3660
attctccttc ttcgccaaaa gcactctgat tgacaaatac gatttatcta atttacacga    3720
aattgcttct ggtggcgctc ccctctctaa ggaagtcggg gaagcggttg ccaagaggtt    3780
ccatctgcca ggtatcaggc aaggatatgg gctcactgag actacatcag ctattctgat    3840
tacacccgag ggggatgata accgggcgc ggtcggtaaa gttgttccat tttttgaagc     3900
gaaggttgtg gatctggata ccgggaaaac gctgggcgtt aatcaaagag cgaactgtg    3960 tgtgagaggt cctatgatta tgtccggtta tgtaacaat ccggaagcga ccaacgcctt    4020
gattgacaag gatggatggc tacattctgg agacatagct tactgggacg aagacgaaca    4080
cttcttcatc gttgaccgcc tgaagtctct gattaagtac aaaggctatc aggtggctcc    4140
cgctgaattg gaatccatct tgctccaaca ccccaacatc ttcgacgcag gtgtcgcagg    4200
```

```
tcttcccgac gatgacgccg gtgaacttcc cgccgccgtt gttgttttgg agcacggaaa    4260
gacgatgacg gaaaaagaga tcgtggatta cgtcgccagt caagtaacaa ccgcgaaaaa    4320
gttgcgcgga ggagttgtgt ttgtggacga agtaccgaaa ggtcttaccg gaaaactcga    4380
cgcaagaaaa atcagagaga tcctcataaa ggccaagaag ggcggaaaga tcgccgtgta    4440
actcgagcat atgggctcga atttccccga tcgttcaaac atttggcaat aaagtttctt    4500
aagattgaat cctgttgccg gtcttgcgat gattatcata taatttctgt tgaattacgt    4560
taagcatgta ataattaaca tgtaatgcat gacgttattt atgagatggg ttttatgat     4620 tagagtcccg caattataca tttaatacgc gatagaaaac aaaatatagc gcgcaaacta    4680
ggataaatta tcgcgcgcgg tgtcatctat gttactagat cgggaattca agcttggcgt    4740
aatcatggac ccagctttct tgtacaaagt ggggtaccaa ttcgaatcca aaaattacgg    4800
atatgaatat aggcatatcc gtatccgaat tatccgtttg acagctagca acgattgtac    4860
aattgcttct ttaaaaaagg aagaaagaaa gaaagaaaag aatcaacatc agcgttaaca    4920
aacggccccg ttacggccca acggtcata tagagtaacg gcgttaagcg ttgaaagact     4980
cctatcgaaa tacgtaaccg caaacgtgtc atagtcagat cccctcttcc ttcaccgcct    5040
caaacacaaa ataatcttc tacagcctat atatacaacc ccccttcta tctctccttt      5100 ctcacaattc atcatctttc tttctctacc cccaattta agaaatcctc tcttctcctc      5160
ttcattttca aggtaaatct ctctctctct ctctctctct gttattcctt gttttaatta    5220
ggtatgtatt attgctagtt tgttaatctg cttatcttat gtatgccta tgtgaatatc     5280 tttatcttgt tcatctcatc cgtttagaag ctataaattt gttgatttga ctgtgtatct    5340
acacgtggtt atgtttatat ctaatcagat atgaatttct tcatattgtt gcgtttgtgt    5400
gtaccaatcc gaaatcgttg atttttttca tttaatcgtg tagctaattg tacgtataca    5460
tatggatcta cgtatcaatt gttcatctgt ttgtgtttgt atgtatacag atctgaaaac    5520
atcacttctc tcatctgatt gtgttgttac atacatagat atagatctgt tatatcattt    5580
tttttattaa ttgtgtatat atatatgtgc atagatctgg attacatgat tgtgattatt    5640
tacatgattt tgttatttac gtatgtatat atgtagatct ggacttttttg gagttgttga    5700 cttgattgta tttgtgtgtg tatatgtgtg ttctgatctt gatatgttat gtatgtgcag    5760
ctgaaccatg gcggcggcaa caacaacaac aacaacatct tcttcgatct ccttctccac    5820
caaaccatct ccttcctcct ccaaatcacc attaccaatc tccagattct ccctcccatt    5880
ctccctaaac cccaacaaat catcctcctc ctcccgccgc cgcggtatca aatccagctc    5940
tccctcctcc atctccgccg tgctcaacac aaccaccaat gtcacaacca ctccctctcc    6000
aaccaaacct accaaacccg aaacattcat ctcccgattc gctccagatc aaccccgcaa    6060
aggcgctgat atcctcgtcg aagctttaga acgtcaaggc gtagaaaccg tattcgctta    6120
ccctggaggt acatcaatgg agattcacca agccttaacc cgctcttcct caatccgtaa    6180
cgtccttcct cgtcacgaac aaggaggtgt attcgcagca gaaggatacg ctcgatcctc    6240
aggtaaacca ggtatctgta tagccacttc aggtcccgga gctacaaatc tcgttagcgg    6300
attagccgat gcgttgttag atagtgttcc tcttgtagca atcacaggac aagtccctcg    6360
tcgtatgatt ggtacagatg cgtttcaaga gactccgatt gttgaggtaa cgcgttcgat    6420
tacgaagcat aactatcttg tgatggatgt tgaagatatc cctaggatta ttgaggaagc    6480 tttctttta gctacttctg gtagacctgg acctgttttg gttgatgttc ctaaagatat      6540
```

```
tcaacaacag cttgcgattc ctaattggga acaggctatg agattacctg gttatatgtc   6600
taggatgcct aaacctccgg aagattctca tttggagcag attgttaggt tgatttctga   6660
gtctaagaag cctgtgttgt atgttggtgg tggttgtttg aattctagcg atgaattggg   6720
taggtttgtt gagcttacgg ggatccctgt tgcgagtacg ttgatggggc tgggatctta   6780
tccttgtgat gatgagttgt cgttacatat gcttggaatg catgggactg tgtatgcaaa   6840
ttacgctgtg gagcatagtg atttgttgtt ggcgtttggg gtaaggtttg atgatcgtgt   6900
cacgggtaag cttgaggctt ttgctagtag ggctaagatt gttcatattg atattgactc   6960
ggctgagatt gggaagaata agactcctca tgtgtctgtg tgtggtgatg ttaagctggc   7020
tttgcaaggg atgaataagg ttcttgagaa ccgagcggag gagcttaagc ttgattttgg   7080
agtttggagg aatgagttga acgtacagaa acagaagttt ccgttgagct taagacgtt    7140 tggggaagct attcctccac agtatgcgat taaggtcctt gatgagttga ctgatggaaa   7200
agccataata agtactggtg tcgggcaaca tcaaatgtgg gcggcgcagt tctacaatta   7260
caagaaacca aggcagtggc tatcatcagg aggccttgga gctatgggat ttggacttcc   7320
tgctgcgatt ggagcgtctg ttgctaaccc tgatgcgata gttgtggata ttgacggaga   7380
tggaagcttt ataatgaatg tgcaagagct agccactatt cgtgtagaga atcttccagt   7440
gaaggtactt ttattaaaca accagcatct tggcatggtt atgcaatggg aagatcggtt   7500
ctacaaagct aaccgagctc acacatttct cggggatccg gctcaggagg acgagatatt   7560
cccgaacatg ttgctgtttg cagcagcttg cgggattcca gcggcgaggg tgacaaagaa   7620
agcagatctc cgagaagcta ttcagacaat gctggataca ccaggacctt acctgttgga   7680
tgtgatttgt ccgcaccaag aacatgtgtt gccgatgatc ccgaatggtg cactttcaa    7740 cgatgtcata acgaaggag atggccggat taaatactga gagatgaaac cggtgattat    7800
cagaaccttt tatggtcttt gtatgcatat ggtaaaaaaa cttagtttgc aatttcctgt   7860
ttgttttggt aatttgagtt tcttttagtt gttgatctgc ctgcttttg gtttacgtca    7920 gactactact gctgttgttg tttggtttcc tttctttcat tttataaata aataatccgg   7980
ttcggtttac tccttgtgac tggctcagtt tggttattgc gaaatgcgaa tggtaaattg   8040
agtaattgaa attcgttatt agggttctaa gctgttttaa cagtcactgg gttaatatct   8100
ctcgaatctt gcatggaaaa tgctcttacc attggttttt aattgaaatg tgctcatatg   8160
ggccgtggtt tccaaattaa ataaaactac gatgtcatcg agaagtaaaa tcaactgtgt   8220
ccacattatc agttttgtgt atacgatgaa atagggtaat tcaaaatcta gcttgatatg   8280
ccttttggtt cattttaacc ttctgtaaac attttttcag attttgaaca agtaaatcca   8340
aaaaaaaaaa aaaaaaatct caactcaaca ctaaattatt ttaatgtata aaagatgctt   8400
aaaacatttg gcttaaaaga aagaagctaa aaacatagag aactcttgta aattgaagta   8460
tgaaaatata ctgaattggg tattatatga atttttctga tttaggattc acatgatcca   8520
aaaaggaaat ccagaagcac taatcagaca ttggaagtag gaatatttca aaaagttttt   8580 ttttttttaag taagtgacaa aagcttttaa aaaatagaaa agaaactagt attaaagttg   8640
taaatttaat aaacaaaaga aattttttat atttttcat ttcttttttcc agcatgaggt    8700 tatgatggca ggatgtggat ttcatttttt tccttttgat agccttttaa ttgatctatt   8760
ataattgacg aaaaaatatt agttaattat agatatattt taggtagtat tagcaattta   8820
cacttccaaa agactatgta agttgtaaat atgatgcgtt gatctcttca tcattcaatg   8880
gttagtcaaa aaaataaaag cttaactagt aaactaaagt agtcaaaaat tgtactttag   8940
```

```
tttaaaatat tacatgaata atccaaaacg acatttatgt gaaacaaaaa caatatctag    9000
agtcgactta attaaactag tggcgcgcca attgactagt aggcctatcg attaattaag    9060
gccgcctcga gcatatgggc atgcaagctt ggcgtaatca tggcaacttt attatacata    9120
gttgataatt cactggccgg atctgcttgg taataattgt cattagattg tttttatgca    9180
tagatgcact cgaaatcagc caattttaga caagtatcaa acggatgtta attcagtaca    9240
ttaaagacgt ccgcaatgtg ttattaagtt gtctaagcgt caatttgttt acaccacaat    9300
atatcctgcc accagccagc caacagctcc ccgaccggca gctcggcaca aaatcaccac    9360
gcgttaccac cacgccggcc ggccgcatgg tgttgaccgt gttcgccggc attgccgagt    9420
tcgagcgttc cctaatcatc gaccgcaccc ggagcgggcg cgaggccgcc aaggcccgag    9480
gcgtgaagtt tggcccccgc cctaccctca ccccggcaca gatcgcgcac gcccgcgagc    9540
tgatcgacca ggaaggccgc accgtgaaag aggcggctgc actgcttggc gtgcatcgct    9600
cgaccctgta ccgcgcactt gagcgcagcg aggaagtgac gcccaccgag gccaggcggc    9660
gcggtgcctt ccgtgaggac gcattgaccg aggccgacgc cctggcggcc gccgagaatg    9720
aacgccaaga ggaacaagca tgaaaccgca ccaggacggc caggacgaac cgttttttcat    9780
taccgaagag atcgaggcgg agatgatcgc ggccgggtac gtgttcgagc cgcccgcgca    9840
cgtctcaacc gtgcggctgc atgaaatcct ggccggtttg tctgatgcca agctggcggc    9900
ctggccggcc agcttggccg ctgaagaaac cgagcgccgc cgtctaaaaa ggtgatgtgt    9960
atttgagtaa aacagcttgc gtcatgcggt cgctgcgtat atgatgcgat gagtaaataa   10020
acaaatacgc aaggggaacg catgaaggtt atcgctgtac ttaaccagaa aggcgggtca   10080
ggcaagacga ccatcgcaac ccatctagcc gcgccctgc aactcgccgg ggccgatgtt   10140
ctgttagtcg attccgatcc ccagggcagt gcccgcgatt gggcggccgt gcgggaagat   10200
caaccgctaa ccgttgtcgg catcgaccgc ccgacgattg accgcgacgt gaaggccatc   10260
ggccggcgcg acttcgtagt gatcgacgga gcgcccagg cggcggactt ggctgtgtcc   10320
gcgatcaagg cagccgactt cgtgctgatt ccggtgcagc caagcccta cgacatatgg   10380
gccaccgccg acctggtgga gctggttaag cagcgcattg aggtcacgga tggaaggcta   10440
caagcggcct ttgtcgtgtc gcgggcgatc aaaggcacgc gcatcggcgg tgaggttgcc   10500
gaggcgctgg ccgggtacga gctgcccatt cttgagtccc gtatcacgca gcgcgtgagc   10560
tacccaggca ctgccgccgc cggcacaacc gttcttgaat cagaacccga gggcgacgct   10620
gcccgcgagg tccaggcgct ggccgctgaa attaaatcaa aactcatttg agttaatgag   10680
gtaaagagaa aatgagcaaa agcacaaaca cgctaagtgc cggccgtccg agcgcacgca   10740
gcagcaaggc tgcaacgttg gccagcctgg cagacacgcc agccatgaag cgggtcaact   10800
ttcagttgcc ggcggaggat cacaccaagc tgaagatgta cgcggtacgc caaggcaaga   10860
ccattaccga gctgctatct gaatacatcg cgcagctacc agagtaaatg agcaaatgaa   10920
taaatgagta gatgaatttt gcggctaaa ggaggcggca tggaaaatca agaacaacca   10980
ggcaccgacg ccgtggaatg ccccatgtgt ggaggaacgg gcggttggcc aggcgtaagc   11040
ggctgggttg tctgccggcc ctgcaatggc actggaaccc ccaagcccga ggaatcggcg   11100
tgagcggtcg caaaccatcc ggcccggtac aaatcggcgc ggcgctgggt gatgacctgg   11160
tggagaagtt gaaggccgcg caggccgccc agcggcaacg catcgaggca gaagcacgcc   11220
ccggtgaatc gtggcaagcg gccgctgatc gaatccgcaa agaatcccgg caaccgccgg   11280
```

```
cagccggtgc gccgtcgatt aggaagccgc ccaagggcga cgagcaacca gattttttcg   11340
ttccgatgct ctatgacgtg ggcacccgcg atagtcgcag catcatggac gtggccgttt   11400
tccgtctgtc gaagcgtgac cgacgagctg gcgaggtgat ccgctacgag cttccagacg   11460
ggcacgtaga ggtttccgca gggccggccg gcatggccag tgtgtgggat tacgacctgg   11520
tactgatggc ggtttcccat ctaaccgaat ccatgaaccg ataccgggaa gggaagggag   11580
acaagcccgg ccgcgtgttc cgtccacacg ttgcggacgt actcaagttc tgccggcgag   11640
ccgatggcgg aaagcagaaa gacgacctgg tagaaacctg cattcggtta aacaccacgc   11700
acgttgccat gcagcgtacg aagaaggcca agaacggccg cctggtgacg gtatccgagg   11760
gtgaagcctt gattagccgc tacaagatcg taaagagcga accgggcgg ccggagtaca   11820
tcgagatcga gctagctgat tggatgtacc gcgagatcac agaaggcaag aacccggacg   11880
tgctgacggt tcaccccgat tacttttga tcgatcccgg catcggccgt tttctctacc   11940
gcctggcacg ccgcgccgca ggcaaggcag aagccagatg gttgttcaag acgatctacg   12000
aacgcagtgg cagcgccgga gagttcaaga agttctgttt caccgtgcgc aagctgatcg   12060
ggtcaaatga cctgccggag tacgatttga aggaggaggc ggggcaggct ggcccgatcc   12120
tagtcatgcg ctaccgcaac ctgatcgagg gcgaagcatc cgccggttcc taatgtacgg   12180
agcagatgct agggcaaatt gccctagcag gggaaaaagg tcgaaaaggt ctctttcctg   12240
tggatagcac gtacattggg aacccaaagc cgtacattgg gaaccggaac ccgtacattg   12300
ggaacccaaa gccgtacatt gggaaccggt cacacatgta agtgactgat ataaaagaga   12360
aaaaaggcga tttttccgcc taaaactctt taaaacttat taaaactctt aaaacccgcc   12420
tggcctgtgc ataactgtct ggccagcgca cagccgaaga gctgcaaaaa gcgcctaccc   12480
ttcggtcgct gcgctcccta cgccccgcg cttcgcgtcg gcctatcgcg gccgctggcc   12540
gctcaaaaat ggctggccta cggccaggca atctaccagg gcgcggacaa gccgcgccgt   12600
cgccactcga ccgccggcgc ccacatcaag gcacccctgcc tcgcgcgttt cggtgatgac   12660
ggtgaaaacc tctgacacat gcagctcccg gagacggtca cagcttgtct gtaagcggat   12720
gccgggagca gacaagcccg tcagggcgcg tcagcgggtt ttggcgggtg tcggggcgca   12780
gccatgaccc agtcacgtag cgatagcgga gtgtatactg gcttaactat gcggcatcag   12840
agcagattgt actgagagtg caccatatgc ggtgtgaaat accgcacaga tgcgtaagga   12900
gaaaataccg catcaggcgc tcttccgctt cctcgctcac tgactcgctg cgctcggtcg   12960
ttcggctgcg gcgagcggta tcagctcact caaaggcggt aatacggtta tccacagaat   13020
caggggataa cgcaggaaag aacatgtgag caaaaggcca gcaaaggcc aggaaccgta   13080
aaaaggccgc gttgctggcg ttttccata ggctccgccc ccctgacgag catcacaaaa   13140
atcgacgctc aagtcagagg tggcgaaacc cgacaggact ataaagatac caggcgtttc   13200
cccctggaag ctccctcgtg cgctctcctg ttccgaccct gccgcttacc ggatacctgt   13260
ccgcctttct cccttcggga agcgtggcgc tttctcatag ctcacgctgt aggtatctca   13320
gttcggtgta ggtcgttcgc tccaagctgg gctgtgtgca cgaaccccc gttcagcccg   13380
accgctgcgc cttatccggt aactatcgtc ttgagtccaa cccggtaaga cacgacttat   13440
cgccactggc agcagccact ggtaacagga ttagcagagc gaggtatgta ggcggtgcta   13500
cagagttctt gaagtggtgg cctaactacg gctacactag aaggacagta tttggtatct   13560
gcgctctgct gaagccagtt accttcggaa aaagagttgg tagctcttga tccggcaaac   13620
aaaccaccgc tggtagcggt ggtttttttg tttgcaagca gcagattacg cgcagaaaaa   13680
```

```
aaggatctca agaagatcct ttgatctttt ctacggggtc tgacgctcag tggaacgaaa      13740
actcacgtta agggattttg gtcatgcatg atatatctcc caatttgtgt agggcttatt      13800
atgcacgctt aaaaataata aaagcagact tgacctgata gtttggctgt gagcaattat      13860
gtgcttagtg catctaacgc ttgagttaag ccgcgccgcg aagcggcgtc ggcttgaacg      13920
aatttctagc tagacattat ttgccgacta ccttggtgat ctcgcctttc acgtagtgga      13980
caaattcttc caactgatct gcgcgcgagg ccaagcgatc ttcttcttgt ccaagataag      14040
cctgtctagc ttcaagtatg acgggctgat actgggccgg caggcgctcc attgcccagt      14100
cggcagcgac atccttcggc gcgattttgc cggttactgc gctgtaccaa atgcgggaca      14160
acgtaagcac tacatttcgc tcatcgccag cccagtcggg cggcgagttc catagcgtta      14220
aggtttcatt tagcgcctca aatagatcct gttcaggaac cggatcaaag agttcctccg      14280
ccgctggacc taccaaggca acgctatgtt ctcttgcttt tgtcagcaag atagccagat      14340
caatgtcgat cgtggctggc tcgaagatac ctgcaagaat gtcattgcgc tgccattctc      14400
caaattgcag ttcgcgctta gctggataac gccacggaat gatgtcgtcg tgcacaacaa      14460
tggtgacttc tacagcgcgg agaatctcgc tctctccagg ggaagccgaa gtttccaaaa      14520
ggtcgttgat caaagctcgc cgcgttgttt catcaagcct tacggtcacc gtaaccagca      14580
aatcaatatc actgtgtggc ttcaggccgc catccactgc ggagccgtac aaatgtacgg      14640
ccagcaacgt cggttcgaga tggcgctcga tgacgccaac tacctctgat agttgagtcg      14700
atacttcggc gatcaccgct tcccccatga tgtttaactt tgttttaggg cgactgccct      14760
gctgcgtaac atcgttgctg ctccataaca tcaaacatcg acccacggcg taacgcgctt      14820
gctgcttgga tgcccgaggc atagactgta ccccaaaaaa acagtcataa caagccatga      14880
aaaccgccac tgcgttccat g                                               14901

<210> SEQ ID NO 63
<211> LENGTH: 51
<212> TYPE: DNA
<213> ORGANISM: Artificial Sequence
<220> FEATURE:
<223> OTHER INFORMATION: synthetic sequence

<400> SEQUENCE: 63
ggggacaact ttgtatagaa aagttcacgg gcaggacata gggactacta c               51

<210> SEQ ID NO 64
<211> LENGTH: 51
<212> TYPE: DNA
<213> ORGANISM: Artificial Sequence
<220> FEATURE:
<223> OTHER INFORMATION: synthetic sequence

<400> SEQUENCE: 64
ggggactgct tttttgtaca aacttggatt tatgataaaa atgtcggttt c               51

<210> SEQ ID NO 65
<211> LENGTH: 50
<212> TYPE: DNA
<213> ORGANISM: Artificial Sequence
<220> FEATURE:
<223> OTHER INFORMATION: synthetic sequence

<400> SEQUENCE: 65
ggggacaact ttgtatagaa aagttctgca gcaaatttac acattgccac                 50
```

<210> SEQ ID NO 66
<211> LENGTH: 50
<212> TYPE: DNA
<213> ORGANISM: Artificial Sequence
<220> FEATURE:
<223> OTHER INFORMATION: synthetic sequence

<400> SEQUENCE: 66

```
gggggactgct tttttgtaca aacttgactg gctatgaaga aattataatc          50
```

<210> SEQ ID NO 67
<211> LENGTH: 15029
<212> TYPE: DNA
<213> ORGANISM: Artificial Sequence
<220> FEATURE:
<223> OTHER INFORMATION: vector sequence

<400> SEQUENCE: 67

```
gacatacaaa tggacgaacg gataaacctt tcacgccct  tttaaatatc cgattattct    60
aataaacgct cttttctctt aggtttaccc gccaatatat cctgtcaaac actgatagtt   120
taaactgaag gcgggaaacg acaatcagat ctagtaggaa acagctatga ccatgattac   180
gccaagctat cgattacgcc aagctatcaa ctttgtatag aaaagttgcc atgattacgc   240
caagcttgca tgcccatatg ctcgaggcgg ccgcagatat cagatctggt cgaccacggg   300
caggacatag ggactactac aagcatagta tgcttcagac aaagagctag aaagaactc    360
ttgatggagg ttaagagaaa aaagtgctag aggggcatag taatcaaact tgtcaaaacc   420
gtcatcatga tgagggatga cataatataa aaagttgact aaggtcttgg tagtactctt   480
tgattagtat tatatattgg tgagaacatg agtcaagagg agacaagaaa ccgaggaacc   540
atagtttagc aacaagatgg aagttgcaaa gttgagctag ccgctcgatt agttacatct   600
cctaagcagt actacaagga atggtctcta tactttcatg tttagcacat ggtagtgcgg   660
attgacaagt tagaaacagt gcttaggaga caaagagtca gtaaaggtat tgaaagagtg   720
aagttgatgc tcgacaggtc aggagaagtc cctccgccag atggtgacta ccaaggggtt   780
ggtatcagct gagacccaaa taagattctt cggttgaacc agtggttcga ccgagactct   840
tagggtggga tttcactgta agatttgtgc attttgttga atataaattg acaattttt    900
ttatttaatt atagattatt tagaatgaat tacatatttta gtttctaaca aggatagcaa   960
tggatgggta tgggtacagg ttaaacatat ctattaccca cccatctagt cgtcgggttt   1020
tacacgtacc cacccgttta cataaaccag accggaattt taaaccgtac ccgtccgtta   1080
gcgggtttca gatttacccg tttaatcggg taaaacctga ttactaaata tatttttt    1140
atttgataaa caaacaaaa atgttaatat tttcatattg gatgcaattt taagaaacac   1200
atattcataa atttccatat ttgtaggaaa ataaaagaa aaatatattc aagaacacaa    1260
atttcaccga catgactttt attacagagt tggaattaga tctaacaatt gaaaaattaa   1320
aattaagata gaatatgttg aggaacatga catagtataa tgctgggtta cccgtcgggt   1380
aggtatcgag gcggatacta ctaaatccat cccactcgct atccgataat cactggtttc   1440
gggtatacc attcccgtca acaggccttt taaccggat aatttcaact tatagtgaat     1500
gaattttgaa taaatagtta gaataccaaa atcctggatt gcatttgcaa tcaaattttg   1560
tgaaccgtta aattttgcat gtacttggga tagatataat agaaccgaat tttcattagt   1620
ttaatttata acttactttg ttcaaagaaa aaaaatatc atccaattta cttataataa    1680
aaataatct  atccaagtta cttattataa tcaacttgta aaaaggtaag aatacaaatg    1740
```

```
tggtagcgta cgtgtgatta tatgtgacga aatgttatat ctaacaaaag tccaaattcc    1800
catggtaaaa aaaatcaaaa tgcatggcag gctgtttgta accttggaat aagatgttgg    1860
ccaattctgg agccgccacg tacgcaagac tcagggccac gttctcttca tgcaaggata    1920
gtagaacacc actccaccca cctcctatat tagaccttttg cccaaccctc cccaactttc    1980
ccatcccatc cacaaagaaa ccgacatttt tatcataaat cactagtccc gggtacccaa    2040
gtttgtacaa aaaagcaggc tggtacctgg tgcttaaaca ctctggtgag ttctagtact    2100
tctgctatga tcgatctcat taccatttct taaatttctc tccctaaata ttccgagttc    2160 ttgattttttg ataacttcag gttttctctt tttgataaat ctggtctttc catttttttt    2220
tttttgtggt taatttagtt tcctatgttc ttcgattgta ttatgcatga tctgtgtttg    2280
gattctgtta gattatgtat tggtgaatat gtatgtgttt ttgcatgtct ggttttggtc    2340
ttaaaaatgt tcaaatctga tgatttgatt gaagcttttt tagtgttggt ttgattcttc    2400
tcaaaactac tgttaattta ctatcatgtt ttccaacttt gattcatgat gacacttttg    2460
ttctgctttg ttataaaatt ttggttggtt tgattttgta attatagtgt aattttgtta    2520
ggaatgaaca tgttttaata ctctgttttc gatttgtcac acattcgaat tattaatcga    2580
taatttaact gaaaattcat ggttctagat cttgttgtca tcagattatt tgtttcgata    2640
attcatcaaa tatgtagtcc ttttgctgat ttgcgactgt ttcatttttt ctcaaaattg    2700
ttttttgtta agtttatcta acagttatcg ttgtcaaaag tctctttcat tttgcaaaat    2760 cttcttttttt tttttgtttg taactttgtt ttttaagcta cacatttagt ctgtaaaata    2820
gcatcgagga acagttgtct tagtagactt gcatgttctt gtaacttcta tttgtttcag    2880
tttgttgatg actgctttga ttttgtaggt caaaccatgg aagacgccaa aaacataaag    2940
aaaggcccgg cgccattcta tccgctggaa gatggaaccg ctggagagca actgcataag    3000
gctatgaaga gatacgccct ggttcctgga acaattgctt ttacagatgc acatatcgag    3060
gtggacatca cttacgctga gtacttcgaa atgtccgttc ggttggcaga agctatgaaa    3120
cgatatgggc tgaatacaaa tcacagaatc gtcgtatgca gtgaaaactc tcttcaattc    3180
tttatgccgg tgttgggcgc gttatttatc ggagttgcag ttgcgcccgc gaacgacatt    3240
tataatgaac gtgaattgct caacagtatg ggcatttcgc agcctaccgt ggtgttcgtt    3300
tccaaaaagg ggttgcaaaa aattttgaac gtgcaaaaaa agctcccaat catccaaaaa    3360
attattatca tggattctaa aacggattac cagggatttc agtcgatgta cacgttcgtc    3420
acatctcatc tacctcccgg ttttaatgaa tacgatttttg tgccagagtc cttcgataggg    3480 gacaagacaa ttgcactgat catgaactcc tctggatcta ctggtctgcc taaaggtgtc    3540
gctctgcctc atagaactgc ctgcgtgaga ttctcgcatg ccagagatcc tattttttggc    3600 aatcaaatca ttccggatac tgcgatttta agtgttgttc cattccatca cggttttgga    3660
atgtttacta cactcggata tttgatatgt ggatttcgag tcgtcttaat gtatagattt    3720
gaagaagagc tgtttctgag gagccttcag gattacaaga ttcaaagtgc gctgctggtg    3780
ccaaccctat tctccttctt cgccaaaagc actctgattg acaaatacga tttatctaat    3840
ttacacgaaa ttgcttctgg tggcgctccc ctctctaagg aagtcgggga agcggttgcc    3900
aagaggttcc atctgccagg tatcaggcaa ggatatgggc tcactgagac tacatcagct    3960
attctgatta cacccgaggg ggatgataaa ccgggcgcgg tcgtaaagt tgttccatttt    4020 tttgaagcga aggttgtgga tctggatacc gggaaaacgc tgggcgttaa tcaaagaggc    4080
```

```
gaactgtgtg tgagaggtcc tatgattatg tccggttatg taaacaatcc ggaagcgacc      4140
aacgccttga ttgacaagga tggatggcta cattctggag acatagctta ctgggacgaa      4200
gacgaacact tcttcatcgt tgaccgcctg aagtctctga ttaagtacaa aggctatcag      4260
gtggctcccg ctgaattgga atccatcttg ctccaacacc ccaacatctt cgacgcaggt      4320
gtcgcaggtc ttcccgacga tgacgccggt gaacttcccg ccgccgttgt tgttttggag      4380
cacggaaaga cgatgacgga aaagagatc gtggattacg tcgccagtca agtaacaacc       4440
gcgaaaaagt tgcgcggagg agttgtgttt gtggacgaag taccgaaagg tcttaccgga      4500
aaactcgacg caagaaaaat cagagagatc ctcataaagg ccaagaaggg cggaaagatc      4560
gccgtgtaac tcgagcatat gggctcgaat ttccccgatc gttcaaacat ttggcaataa      4620
agtttcttaa gattgaatcc tgttgccggt cttgcgatga ttatcatata atttctgttg      4680
aattacgtta agcatgtaat aattaacatg taatgcatga cgttatttat gagatgggtt      4740
tttatgatta gagtcccgca attatacatt taatacgcga tagaaaacaa aatatagcgc      4800
gcaaactagg ataaattatc gcgcgcggtg tcatctatgt tactagatcg ggaattcaag      4860
cttggcgtaa tcatggaccc agcttttcttg tacaaagtgg ggtaccaatt cgaatccaaa      4920
aattacggat atgaatatag gcatatccgt atccgaatta ccgtttgac agctagcaac       4980 gattgtacaa ttgcttcttt aaaaaaggaa gaaagaaaga agaaaagaa tcaacatcag       5040 cgttaacaaa cggccccgtt acggcccaaa cggtcatata gagtaacggc gttaagcgtt      5100
gaaagactcc tatcgaaata cgtaaccgca aacgtgtcat agtcagatcc cctcttcctt      5160
caccgcctca aacacaaaaa taatcttcta cagcctatat atacaacccc ccttctatc       5220 tctcctttct cacaattcat catctttctt tctctacccc caattttaag aaatcctctc      5280
ttctcctctt catttttcaag gtaaatctct ctctctctct ctctctctgt tattccttgt     5340
tttaattagg tatgtattat tgctagtttg ttaatctgct tatcttatgt atgccttatg      5400
tgaatatctt tatcttgttc atctcatccg tttagaagct ataaatttgt tgatttgact      5460
gtgtatctac acgtggttat gtttatatct aatcagatat gaatttcttc atattgttgc      5520
gtttgtgtgt accaatccga aatcgttgat ttttttcatt taatcgtgta gctaattgta      5580
cgtatacata tggatctacg tatcaattgt tcatctgttt gtgtttgtat gtatacagat      5640
ctgaaaacat cacttctctc atctgattgt gttgttacat acatagatat agatctgtta     5700
tatcattttt tttattaatt gtgtatatat atatgtgcat agatctggat tacatgattg      5760
tgattattta catgattttg ttatttacgt atgtatatat gtagatctgg acttttgga      5820 gttgttgact tgattgtatt tgtgtgtgta tatgtgtgtt ctgatcttga tatgttatgt      5880
atgtgcagct gaaccatggc ggcggcaaca acaacaacaa caacatcttc ttcgatctcc      5940
ttctccacca aaccatctcc ttcctcctcc aaatcaccat taccaatctc cagattctcc      6000
ctcccattct ccctaaaccc caacaaatca tcctcctcct cccgccgccg cggtatcaaa      6060
tccagctctc cctcctccat ctccgccgtg ctcaacacaa ccaccaatgt cacaaccact      6120
ccctctccaa ccaaacctac caaacccgaa acattcatct cccgattcgc tccagatcaa      6180
ccccgcaaag gcgctgatat cctcgtcgaa gctttagaac gtcaaggcgt agaaaccgta      6240
ttcgcttacc ctggaggtac atcaatggag attcaccaag ccttaacccg ctcttcctca      6300
atccgtaacg tccttcctcg tcacgaacaa ggaggtgtat tcgcagcaga aggatacgct      6360
cgatcctcag gtaaaccagg tatctgtata gccacttcag gtcccggagc tacaaatctc      6420
gttagcggat tagccgatgc gttgttagat agtgttcctc ttgtagcaat cacaggacaa      6480
```

```
gtccctcgtc gtatgattgg tacagatgcg tttcaagaga ctccgattgt tgaggtaacg    6540
cgttcgatta cgaagcataa ctatcttgtg atggatgttg aagatatccc taggattatt    6600
gaggaagctt tcttttagc tacttctggt agacctggac ctgttttggt tgatgttcct    6660
aaagatattc aacaacagct tgcgattcct aattgggaac aggctatgag attacctggt    6720
tatatgtcta ggatgcctaa acctccggaa gattctcatt tggagcagat tgttaggttg    6780
atttctgagt ctaagaagcc tgtgttgtat gttggtggtg gttgtttgaa ttctagcgat    6840
gaattgggta ggtttgttga gcttacgggg atccctgttg cgagtacgtt gatggggctg    6900
ggatcttatc cttgtgatga tgagttgtcg ttacatatgc ttggaatgca tgggactgtg    6960
tatgcaaatt acgctgtgga gcatagtgat ttgttgttgg cgtttggggt aaggtttgat    7020
gatcgtgtca cgggtaagct tgaggctttt gctagtaggg ctaagattgt tcatattgat    7080
attgactcgg ctgagattgg gaagaataag actcctcatg tgtctgtgtg tggtgatgtt    7140
aagctggctt tgcaagggat gaataaggtt cttgagaacc gagcggagga gcttaagctt    7200
gattttggag tttggaggaa tgagttgaac gtacagaaac agaagtttcc gttgagcttt    7260
aagacgtttg gggaagctat tcctccacag tatgcgatta aggtccttga tgagttgact    7320
gatggaaaag ccataataag tactggtgtc gggcaacatc aaatgtgggc ggcgcagttc    7380
tacaattaca agaaaccaag gcagtggcta tcatcaggag gccttggagc tatgggattt    7440
ggacttcctg ctgcgattgg agcgtctgtt gctaaccctg atgcgatagt tgtggatatt    7500
gacggagatg gaagctttat aatgaatgtg caagagctag ccactattcg tgtagagaat    7560
cttccagtga aggtactttt attaaacaac cagcatcttg gcatggttat gcaatgggaa    7620
gatcggttct acaaagctaa ccgagctcac acatttctcg gggatccggc tcaggaggac    7680
gagatattcc cgaacatgtt gctgtttgca gcagcttgcg ggattccagc ggcgagggtg    7740
acaaagaaag cagatctccg agaagctatt cagacaatgc tggatacacc aggaccttac    7800
ctgttggatg tgatttgtcc gcaccaagaa catgtgttgc cgatgatccc gaatggtggc    7860
actttcaacg atgtcataac ggaaggagat ggccggatta aatactgaga gatgaaaccg    7920
gtgattatca gaacctttta tggtctttgt atgcatatgg taaaaaaact tagttttgcaa   7980 tttcctgttt gttttggtaa tttgagtttc ttttagttgt tgatctgcct gcttttggt    8040 ttacgtcaga ctactactgc tgttgttgtt tggtttcctt tctttcattt tataaataaa    8100
taatccggtt cggtttactc cttgtgactg gctcagtttg gttattgcga aatgcgaatg    8160
gtaaattgag taattgaaat tcgttattag ggttctaagc tgttttaaca gtcactgggt    8220
taatatctct cgaatcttgc atggaaaatg ctcttaccat tggtttttaa ttgaaatgtg    8280
ctcatatggg ccgtggtttc caaattaaat aaaactacga tgtcatcgag aagtaaaatc    8340
aactgtgtcc acattatcag ttttgtgtat acgatgaaat agggtaattc aaaatctagc    8400
ttgatatgcc ttttggttca ttttaaccct ctgtaaacat tttttcagat tttgaacaag    8460
taaatccaaa aaaaaaaaaa aaaaatctca actcaacact aaattatttt aatgtataaa    8520
agatgcttaa aacatttggc ttaaaagaaa gaagctaaaa acatagagaa ctcttgtaaa    8580
ttgaagtatg aaaatatact gaattgggta ttatatgaat ttttctgatt taggattcac    8640
atgatccaaa aaggaaatcc agaagcacta atcagacatt ggaagtagga atatttcaaa    8700
aagttttttt tttttaagta agtgacaaaa gcttttaaaa aatagaaaag aaactagtat    8760
taaagttgta aatttaataa acaaaagaaa ttttttatat tttttcattt cttttttccag   8820
```

```
catgaggtta tgatggcagg atgtggattt catttttttc cttttgatag ccttttaatt     8880
gatctattat aattgacgaa aaaatattag ttaattatag atatatttta ggtagtatta     8940
gcaatttaca cttccaaaag actatgtaag ttgtaaatat gatgcgttga tctcttcatc     9000
attcaatggt tagtcaaaaa aataaaagct taactagtaa actaaagtag tcaaaaattg     9060
tactttagtt taaaatatta catgaataat ccaaaacgac atttatgtga aacaaaaaca     9120
atatctagag tcgacttaat taaactagtg gcgcgccaat tgactagtag gcctatcgat     9180
taattaaggc cgcctcgagc atatgggcat gcaagcttgg cgtaatcatg gcaactttat     9240
tatacatagt tgataattca ctggccggat ctgcttggta ataattgtca ttagattgtt     9300
tttatgcata gatgcactcg aaatcagcca attttagaca agtatcaaac ggatgttaat     9360
tcagtacatt aaagacgtcc gcaatgtgtt attaagttgt ctaagcgtca atttgtttac     9420
accacaatat atcctgccac cagccagcca acagctcccc gaccggcagc tcggcacaaa     9480
atcaccacgc gttaccacca cgccggccgg ccgcatggtg ttgaccgtgt tcgccggcat     9540
tgccgagttc gagcgttccc taatcatcga ccgcacccgg agcgggcgcg aggccgccaa     9600
ggcccgaggc gtgaagtttg gcccccgccc taccctcacc ccggcacaga tcgcgcacgc     9660
ccgcgagctg atcgaccagg aaggccgcac cgtgaaagag gcggctgcac tgcttggcgt     9720
gcatcgctcg accctgtacc gcgcacttga gcgcagcgag gaagtgacgc ccaccgaggc     9780
caggcggcgc ggtgccttcc gtgaggacgc attgaccgag gccgacgccc tggcggccgc     9840
cgagaatgaa cgccaagagg aacaagcatg aaaccgcacc aggacggcca ggacgaaccg     9900
tttttcatta ccgaagagat cgaggcgag atgatcgcgg ccgggtacgt gttcgagccg     9960
cccgcgcacg tctcaaccgt gcggctgcat gaaatcctgg ccggtttgtc tgatgccaag     10020
ctggcggcct ggccggccag cttggccgct gaagaaaccg agcgccgccg tctaaaaagg     10080
tgatgtgtat ttgagtaaaa cagcttgcgt catgcggtcg ctgcgtatat gatgcgatga     10140
gtaaataaac aaatacgcaa ggggaacgca tgaaggttat cgctgtactt aaccagaaag     10200
gcgggtcagg caagacgacc atcgcaaccc atctagcccg cgccctgcaa ctcgccgggg     10260
ccgatgttct gttagtcgat tccgatcccc agggcagtgc ccgcgattgg gcggccgtgc     10320
gggaagatca accgctaacc gttgtcggca tcgaccgccc gacgattgac cgcgacgtga     10380
aggccatcgg ccggcgcgac ttcgtagtga tcgacgagc gccccaggcg gcggacttgg     10440
ctgtgtccgc gatcaaggca gccgacttcg tgctgattcc ggtgcagcca gcccttacg      10500
acatatgggc caccgccgac ctggtggagc tggttaagca gcgcattgag gtcacggatg     10560
gaaggctaca gcggcctttt gtcgtgtcgc gggcgatcaa aggcacgcgc atcggcggtg     10620
aggttgccga ggcgctggcc gggtacgagc tgcccattct tgagtcccgt atcacgcagc     10680
gcgtgagcta cccaggcact gccgccgccg gcacaaccgt tcttgaatca gaacccgagg     10740
gcgacgctgc ccgcgaggtc caggcgctgg ccgctgaaat taaatcaaaa ctcatttgag     10800
ttaatgaggt aaagagaaaa tgagcaaaag cacaaacacg ctaagtgccg gccgtccgag     10860
cgcacgcagc agcaaggctg caacgttggc cagcctggca gacacgccag ccatgaagcg     10920
ggtcaacttt cagttgccgg cggaggatca caccaagctg aagatgtacg cggtacgcca     10980
aggcaagacc attaccgagc tgctatctga atacatcgcg cagctaccag agtaaatgag     11040
caaatgaata aatgagtaga tgaatttag cggctaaagg aggcggcatg gaaaatcaag     11100
aacaaccagg caccgacgcc gtggaatgcc ccatgtgtgg aggaacgggc ggttggccag     11160
gcgtaagcgg ctgggttgtc tgccggccct gcaatggcac tggaaccccc aagcccgagg     11220
```

```
aatcggcgtg agcggtcgca aaccatccgg cccggtacaa atcggcgcgg cgctgggtga  11280
tgacctggtg gagaagttga aggccgcgca ggccgcccag cggcaacgca tcgaggcaga  11340
agcacgcccc ggtgaatcgt ggcaagcggc cgctgatcga atccgcaaag aatcccggca  11400
accgccggca gccggtgcgc cgtcgattag gaagccgccc aagggcgacg agcaaccaga  11460
ttttttcgtt ccgatgctct atgacgtggg cacccgcgat agtcgcagca tcatggacgt  11520
ggccgttttc cgtctgtcga agcgtgaccg acgagctggc gaggtgatcc gctacgagct  11580
tccagacggg cacgtagagg tttccgcagg gccggccggc atggccagtg tgtgggatta  11640
cgacctggta ctgatggcgg tttcccatct aaccgaatcc atgaaccgat accgggaagg  11700
gaagggagac aagcccggcc gcgtgttccg tccacacgtt gcggacgtac tcaagttctg  11760
ccggcgagcc gatggcggaa agcagaaaga cgacctggta gaaacctgca ttcggttaaa  11820
caccacgcac gttgccatgc agcgtacgaa gaaggccaag aacggccgcc tggtgacggt  11880
atccgagggt gaagccttga ttagccgcta caagatcgta aagagcgaaa ccgggcggcc  11940
ggagtacatc gagatcgagc tagctgattg gatgtaccgc gagatcacag aaggcaagaa  12000
cccgacgtg ctgacggttc accccgatta cttttttgatc gatcccggca tcggccgttt  12060
tctctaccgc ctggcacgcc gcgccgcagg caaggcagaa gccagatggt tgttcaagac  12120
gatctacgaa cgcagtggca gcgcggaga gttcaagaag ttctgttcca ccgtgcgcaa  12180
gctgatcggg tcaaatgacc tgccggagta cgatttgaag gaggaggcgg ggcaggctgg  12240
cccgatccta gtcatgcgct accgcaacct gatcgagggc gaagcatccg ccggttccta  12300
atgtacggag cagatgctag ggcaaattgc cctagcaggg gaaaaaggtc gaaaaggtct  12360
ctttcctgtg gatagcacgt acattgggaa cccaaagccg tacattggga accggaaccc  12420
gtacattggg aacccaaagc cgtacattgg gaaccggtca cacatgtaag tgactgatat  12480
aaaagagaaa aaaggcgatt tttccgccta aaactctta aaacttatta aaactcttaa  12540
aacccgcctg gcctgtgcat aactgtctgg ccagcgcaca gccgaagagc tgcaaaaagc  12600
gcctacccttt cggtcgctgc gctcccctacg ccccgccgct tcgcgtcggc ctatcgcggc  12660
cgctggccgc tcaaaaatgg ctggcctacg gccaggcaat ctaccagggc gcggacaagc  12720
cgcgccgtcg ccactcgacc gccggcgccc acatcaaggc accctgcctc gcgcgtttcg  12780
gtgatgacgg tgaaaacctc tgacacatgc agctcccgga gacggtcaca gcttgtctgt  12840
aagcggatgc cgggagcaga caagcccgtc agggcgcgtc agcgggtgtt ggcgggtgtc  12900
ggggcgcagc catgacccag tcacgtagcg atagcggagt gtatactggc ttaactatgc  12960
ggcatcagag cagattgtac tgagagtgca ccatatgcgg tgtgaaatac cgcacagatg  13020
cgtaaggaga aaataccgca tcaggcgctc ttccgcttcc tcgctcactg actcgctgcg  13080
ctcggtcgtt cggctgcggc gagcggtatc agctcactca aaggcggtaa tacggttatc  13140
cacagaatca ggggataacg caggaaagaa catgtgagca aaaggccagc aaaaggccag  13200
gaaccgtaaa aaggccgcgt tgctggcgtt tttccatagg ctccgccccc ctgacgagca  13260
tcacaaaaat cgacgctcaa gtcagaggtg gcgaaacccg acaggactat aaagatacca  13320
ggcgtttccc cctggaagct ccctcgtgcg ctctcctgtt ccgaccctgc cgcttaccgg  13380
atacctgtcc gcctttctcc cttcgggaag cgtggcgctt tctcatagct cacgctgtag  13440
gtatctcagt tcggtgtagg tcgttcgctc caagctgggc tgtgtgcacg aaccccccgt  13500
tcagcccgac cgctgcgcct tatccggtaa ctatcgtctt gagtccaacc cggtaagaca  13560
```

```
cgacttatcg ccactggcag cagccactgg taacaggatt agcagagcga ggtatgtagg    13620
cggtgctaca gagttcttga agtggtggcc taactacggc tacactagaa ggacagtatt    13680
tggtatctgc gctctgctga agccagttac cttcggaaaa agagttggta gctcttgatc    13740
cggcaaacaa accaccgctg gtagcggtgg ttttttttgtt tgcaagcagc agattacgcg    13800
cagaaaaaaa ggatctcaag aagatccttt gatcttttct acggggtctg acgctcagtg    13860
gaacgaaaac tcacgttaag ggattttggt catgcatgat atatctccca atttgtgtag    13920
ggcttattat gcacgcttaa aaataataaa agcagacttg acctgatagt ttggctgtga    13980
gcaattatgt gcttagtgca tctaacgctt gagttaagcc gcgccgcgaa gcggcgtcgg    14040
cttgaacgaa tttctagcta gacattattt gccgactacc ttggtgatct cgccttttcac   14100 gtagtggaca aattcttcca actgatctgc gcgcgaggcc aagcgatctt cttcttgtcc    14160
aagataagcc tgtctagctt caagtatgac gggctgatac tgggccggca ggcgctccat    14220
tgcccagtcg gcagcgacat ccttcggcgc gattttgccg gttactgcgc tgtaccaaat    14280
gcgggacaac gtaagcacta catttcgctc atcgccagcc cagtcgggcg gcgagttcca    14340
tagcgttaag gtttcattta gcgcctcaaa tagatcctgt tcaggaaccg gatcaaagag    14400
ttcctccgcc gctggaccta ccaaggcaac gctatgttct cttgcttttg tcagcaagat    14460
agccagatca atgtcgatcg tggctggctc gaagatacct gcaagaatgt cattgcgctg    14520
ccattctcca aattgcagtt cgcgcttagc tggataacgc cacggaatga tgtcgtcgtg    14580
cacaacaatg gtgacttcta cagcgcggag aatctcgctc tctccagggg aagccgaagt    14640
ttccaaaagg tcgttgatca aagctcgccg cgttgtttca tcaagcctta cggtcaccgt    14700
aaccagcaaa tcaatatcac tgtgtggctt caggccgcca tccactgcgg agccgtacaa    14760
atgtacggcc agcaacgtcg gttcgagatg gcgctcgatg acgccaacta cctctgatag    14820
ttgagtcgat acttcggcga tcaccgcttc ccccatgatg tttaactttg ttttagggcg    14880
actgccctgc tgcgtaacat cgttgctgct ccataacatc aaacatcgac ccacggcgta    14940
acgcgcttgc tgcttggatg cccgaggcat agactgtacc ccaaaaaaac agtcataaca    15000
agccatgaaa accgccactg cgttccatg                                       15029
```

<210> SEQ ID NO 68
<211> LENGTH: 38
<212> TYPE: DNA
<213> ORGANISM: Artificial Sequence
<220> FEATURE:
<223> OTHER INFORMATION: synthetic sequence

<400> SEQUENCE: 68

```
aataatggcg cgcctggtgc ttaaacactc tggtgagt                              38
```

<210> SEQ ID NO 69
<211> LENGTH: 40
<212> TYPE: DNA
<213> ORGANISM: Artificial Sequence
<220> FEATURE:
<223> OTHER INFORMATION: synthetic sequence

<400> SEQUENCE: 69

```
aataatggcg cgcctttgac ctacaaaatc aaagcagtca                            40
```

<210> SEQ ID NO 70
<211> LENGTH: 36
<212> TYPE: DNA
<213> ORGANISM: Artificial Sequence

```
<220> FEATURE:
<223> OTHER INFORMATION: synthetic sequence

<400> SEQUENCE: 70 tttttggcg cgccagttct tgctttcga agttgc                                    36

<210> SEQ ID NO 71
<211> LENGTH: 37
<212> TYPE: DNA
<213> ORGANISM: Artificial Sequence
<220> FEATURE:
<223> OTHER INFORMATION: synthetic sequence

<400> SEQUENCE: 71 tttttggcg cgcctactac gtactgtttt caattct                                  37

<210> SEQ ID NO 72
<211> LENGTH: 35
<212> TYPE: DNA
<213> ORGANISM: Artificial Sequence
<220> FEATURE:
<223> OTHER INFORMATION: synthetic sequence

<400> SEQUENCE: 72
aataaaggcg cgccgtccag aattttctcc attga                                   35

<210> SEQ ID NO 73
<211> LENGTH: 36
<212> TYPE: DNA
<213> ORGANISM: Artificial Sequence
<220> FEATURE:
<223> OTHER INFORMATION: synthetic sequence

<400> SEQUENCE: 73
aataaaggcg cgcctcttca ctatccaaag ctctca                                  36

<210> SEQ ID NO 74
<211> LENGTH: 39
<212> TYPE: DNA
<213> ORGANISM: Artificial Sequence
<220> FEATURE:
<223> OTHER INFORMATION: synthetic sequence

<400> SEQUENCE: 74
ttttatggcg cgcctagctt aatctcagat tcgaatcgt                               39

<210> SEQ ID NO 75
<211> LENGTH: 42
<212> TYPE: DNA
<213> ORGANISM: Artificial Sequence
<220> FEATURE:
<223> OTHER INFORMATION: synthetic sequence

<400> SEQUENCE: 75
ttttatggcg cgcctagtat ctacatacca atcatacaaa tg                           42

<210> SEQ ID NO 76
<211> LENGTH: 34
<212> TYPE: DNA
<213> ORGANISM: Artificial Sequence
<220> FEATURE:
<223> OTHER INFORMATION: synthetic sequence

<400> SEQUENCE: 76 tttttggcg cgcctttcac gatttggaat ttga                                     34
```

<210> SEQ ID NO 77
<211> LENGTH: 38
<212> TYPE: DNA
<213> ORGANISM: Artificial Sequence
<220> FEATURE:
<223> OTHER INFORMATION: synthetic sequence

<400> SEQUENCE: 77 tttttggcg cgcctctaca acattaaaac gaccatta          38

<210> SEQ ID NO 78
<211> LENGTH: 34
<212> TYPE: DNA
<213> ORGANISM: Artificial Sequence
<220> FEATURE:
<223> OTHER INFORMATION: synthetic sequence

<400> SEQUENCE: 78
tatataggcg cgccagggtt tcgttttgt ttca              34

<210> SEQ ID NO 79
<211> LENGTH: 37
<212> TYPE: DNA
<213> ORGANISM: Artificial Sequence
<220> FEATURE:
<223> OTHER INFORMATION: synthetic sequence

<400> SEQUENCE: 79
tatataggcg cgccttatct cctgctcaaa gaaacca          37

<210> SEQ ID NO 80
<211> LENGTH: 35
<212> TYPE: DNA
<213> ORGANISM: Artificial Sequence
<220> FEATURE:
<223> OTHER INFORMATION: synthetic sequence

<400> SEQUENCE: 80
tatataggcg cgccactgtt taagcttcac tgtct            35

<210> SEQ ID NO 81
<211> LENGTH: 34
<212> TYPE: DNA
<213> ORGANISM: Artificial Sequence
<220> FEATURE:
<223> OTHER INFORMATION: synthetic sequence

<400> SEQUENCE: 81
tatataggcg cgcctttctt ctaaagctga aagt             34

<210> SEQ ID NO 82
<211> LENGTH: 14495
<212> TYPE: DNA
<213> ORGANISM: Artificial Sequence
<220> FEATURE:
<223> OTHER INFORMATION: vector sequence

<400> SEQUENCE: 82
gtgattttgt gccgagctgc cggtcgggga gctgttggct ggctggtggc aggatatatt      60
gtggtgtaaa caaattgacg cttagacaac ttaataacac attgcggacg tctttaatgt    120
actgaattta gttactgatc actgattaag tactgatatc ggtaccaagc ttccgcggct    180
gcagtgcagc gtgacccggt cgtgcccctc tctagagata atgagcattg catgtctaag    240
ttataaaaaa ttaccacata ttttttttgt cacacttgtt tgaagtgcag tttatctatc    300

```
tttatacata tatttaaact ttactctacg aataatataa tctatagtac tacaataata    360
tcagtgtttt agagaatcat ataaatgaac agttagacat ggtctaaagg acaattgagt    420
attttgacaa caggactcta cagtttatc ttttagtgt gcatgtgttc tccttttttt    480
ttgcaaatag cttcacctat ataatacttc atccatttta ttagtacatc catttagggt    540
ttagggttaa tggtttttat agactaattt ttttagtaca tctatttat tctattttag    600 cctctaaatt aagaaaacta aaactctatt ttagttttt tatttaatag tttagatata    660
aaatagaata aaataaagtg actaaaaatt aaacaaatac cctttaagaa attaaaaaaa    720
ctaaggaaac attttcttg tttcgagtag ataatgccag cctgttaaac gccgtcgacg    780
agtctaacgg acaccaacca gcgaaccagc agcgtcgcgt cgggccaagc gaagcagacg    840
gcacggcatc tctgtcgctg cctctggacc cctctcgaga gttccgctcc accgttggac    900
ttgctccgct gtcggcatcc agaaattgcg tggcggagcg gcagacgtga gccggcacgg    960
caggcggcct cctcctcctc tcacggcacc ggcagctacg ggggattcct ttcccaccgc   1020
tccttcgctt tcccttcctc gcccgccgta ataaatagac ccccctcca caccctcttt   1080 ccccaacctc gtgttgttcg gagcgcacac acacacaacc agatctcccc caaatccacc   1140
cgtcggcacc tccgcttcaa ggtacgccgc tcgtcctccc ccccccccc cctctctacc   1200 ttctctagat cggcgttccg gtccatggtt agggcccggt agttctactt ctgttcatgt   1260
ttgtgttaga tccgtgtttg tgttagatcc gtgctgctag cgttcgtaca cggatgcgac   1320
ctgtacgtca gacacgttct gattgctaac ttgccagtgt ttctctttgg ggaatcctgg   1380
gatggctcta gccgttccgc agacgggatc gatttcatga ttttttttgt ttcgttgcat   1440
agggtttggt ttgccctttt cctttatttc aatatatgcc gtgcacttgt ttgtcgggtc   1500
atcttttcat gcttttttt gtcttggttg tgatgatgtg gtctggttgg gcggtcgttc   1560
tagatcggag tagaattctg tttcaaacta cctggtggat ttattaattt tggatctgta   1620
tgtgtgtgcc atacatattc atagttacga attgaagatg atggatggaa atatcgatct   1680
aggataggta tacatgttga tgcgggtttt actgatgcat atacagagat gcttttgtt   1740 cgcttggttg tgatgatgtg gtgtggttgg gcggtcgttc attcgttcta gatcggagta   1800
gaatactgtt tcaaactacc tggtgtattt attaattttg gaactgtatg tgtgtgtcat   1860
acatcttcat agttacgagt ttaagatgga tggaaatatc gatctaggat aggtatacat   1920
gttgatgtgg gttttactga tgcatataca tgatggcata tgcagcatct attcatatgc   1980
tctaaccttg agtacctatc tattataata aacaagtatg ttttataatt atttcgatct   2040
tgatatactt ggatgatggc atatgcagca gctatatgtg gatttttta gccctgcctt   2100 catacgctat ttatttgctt ggtactgttt cttttgtcga tgctcaccct gttgtttggt   2160
gttacttctg cagcccgggg gatccactag ttctagaaac catggccacc gccgccgccg   2220
cgtctaccgc gctcactggc gccactaccg ctgcgcccaa ggcgaggcgc cgggcgcacc   2280
tcctggccac ccgccgcgcc ctcgccgcgc ccatcaggtg ctcagcggcg tcacccgcca   2340
tgccgatggc tccccggcc accccgctcc ggcgtggggg ccccaccgat ccccgcaagg   2400
gcgccgacat cctcgtcgag tccctcgagc gctgcgcgt ccgcgacgtc ttcgcctacc   2460
ccggcggcac gtccatggag atccaccagg cactcacccg ctcccccgtc atcgccaacc   2520
acctcttccg ccacgagcaa ggggaggcct ttgcggcctc cggctacgcg cgctcctcgg   2580
gccgcgtcgg cgtctgcatc gccacctccg gccccggcgc caccaacctt gtctccgcgc   2640
```

```
tcgccgacgc gctgctcgat tccgtcccca tggtcgccat cacgggacag gtgccgcgac    2700
gcatgattgg caccgacgcc ttccaggaga cgcccatcgt cgaggtcacc cgctccatca    2760
ccaagcacaa ctacctggtc ctcgacgtcg acgacatccc ccgcgtcgtg caggaggctt    2820
tcttcctcgc ctcctctggt cgaccggggc cggtgcttgt cgacatcccc aaggacatcc    2880
agcagcagat ggcggtgcct gtctgggaca agcccatgag tctgcctggg tacattgcgc    2940
gccttcccaa gcccctgcg actgagttgc ttgagcaggt gctgcgtctt gttggtgaat    3000
cccggcgccc tgttctttat gttggcggtg gctgcgcagc atctggtgag gagttgcgac    3060
gctttgtgga gctgactgga atcccggtca caactactct tatgggcctc ggcaacttcc    3120
ccagcgacga cccactgtct ctgcgcatgc taggtatgca tggcacggtg tatgcaaatt    3180
atgcagtgga taaggccgat ctgttgcttg cacttggtgt gcggtttgat gatcgtgtga    3240
cagggaagat tgaggctttt gcaagcaggg ctaagattgt gcacgttgat attgatccgg    3300
ctgagattgg caagaacaag cagccacatg tgtccatctg tgcagatgtt aagcttgctt    3360
tgcagggcat gaatgctctt cttgaaggaa gcacatcaaa gaagagcttt gacttttggct   3420 catggaacga tgagttggat cagcagaaga gggaattccc ccttgggtat aaaacatcta    3480
atgaggagat ccagccacaa tatgctattc aggttcttga tgagctgacg aaaggcgagg    3540
ccatcatcgg cacaggtgtt gggcagcacc agatgtgggc ggcacagtac tacacttaca    3600
agcggccaag gcagtggttg tcttcagctg gtcttgggc tatgggattt ggtttgccgg    3660
ctgctgctgg tgcttctgtg gccaacccag gtgttactgt tgttgacatc gatggagatg    3720
gtagctttct catgaacgtt caggagctag ctatgatccg aattgagaac ctcccggtga    3780
aggtctttgt gctaaacaac cagcacctgg ggatggtggt gcagtgggag gacaggttct    3840
ataaggccaa cagagcgcac acatacttgg gaaacccaga gaatgaaagt gagatatatc    3900
cagatttcgt gacgatcgcc aaagggttca acattccagc ggtccgtgtg acaaagaaga    3960
acgaagtccg cgcagcgata aagaagatgc tcgagactcc agggccgtac ctcttggata    4020
taatcgtccc acaccaggag catgtgttgc ctatgatccc taatggtggg gctttcaagg    4080
atatgatcct ggatggtgat ggcaggactg tgtactgatc taaaatccag caagcaactg    4140
atctaaaatc cagcaagcac cgcctccctg ctagtacaag ggtgatatgt ttttatctgt    4200
gtgatgttct cctgtattct atctttttt gtaggccgtc agctatctgt tatggtaatc    4260
ctatgtagct tccgaccttg taattgtgta gtctgttgtt ttccttctgg catgtgtcat    4320
aagagatcat ttaagtgcct tttgctacat ataaataaga taataagcac tgctatgcag    4380
tggttctgaa ttggcttctg ttgccaaatt taagtgtcca actggtcctt gcttttgttt    4440
tcgctatttt tttccttttt tagttattat tatattggta atttcaactc aacatatgat    4500
gtatggaata atgctagggc tgcaatttca aactatttta caaaccagaa tggcattttc    4560
gtggtttgag gggagtgaaa aaaaatgagg catttgactg aattagttac ctgatccatt    4620
ttcgtggttt ggatcattgg aattaaattc cattctaata atagtaattt tggcatatat    4680
caattaagtt aattcggttt tatgcaaaat atatttgtat actattatta tcaagatgtc    4740
ggagatattt atatgctaca tttttactat acaggagtga gatgaagagt gtcatgtaag    4800
ttacacagta gaaacaaatt ctattaatgc ataaaatcat ttccatcatc caccctatga    4860
atttgagata gacctatatc taaactttga aaagtggttg aatatcaaat tccaaattaa    4920
ataagttatt ttattgagtg aattctaatt tctctaaaac gaagggatct aaacgccctc    4980
taaagctaat ttggaaactc aaactttctt agcattggag gggattgaga aaaaatatta    5040
```

```
attcattttc atctcaatca ttcaatctcc aaagagattt gagttcctta ttagtctgtt    5100
ccatgcatca aatcggctca atgtgtcatt atttgccatg acgattgacg agttgttctg    5160
gggcctagcg cttccacgc cgatgtgctg gggcctggtc ctggagaaga cagcttgata    5220
tttaaagcta tcaattgttt caattgattc ccacttcatt tttctaaatg tagaaaacgg    5280
tgacgtataa gaaaaagaat gaattaggac ttttattccg tacactaatc tagagcggcc    5340
caagcttgta cactagtacg cgtcaattga tttaaattta attaatcccg tgtccgtcaa    5400
tgtgatacta ctagcatagt actagtacca tgcatacaca cagcaggtcg gccgcctgga    5460
tggatcgatg atgatactac atcatcctgt catccatcca ggcgatctag aaggggcgtg    5520
gctagctagc aaactgtgac cggttttttct acgccgataa taatactttg tcatggtaca    5580
gacgtacagt actggttata tatatctgta gatttcaact gaaaagctag gatagctaga    5640
ttaattcctg agaaacacag ataaaattcg agcttggcta tagatgacaa acggaagac    5700 gcatgcattg gacgacgtat gcaatgcgag cgcgtctcgt gtcgtcccgt ccaagtctgg    5760
cgatctcacg ccacgtgctc aacagctcaa ggactgttcg tcaccagcgt taaattcatt    5820
gaagggatga cgcatttcgg catttgtcat tgcttgtagc tatatatata tatccaacag    5880
atttctctca agcttttgta tgcgtgaatg taaagtctag cttatacgac agcacgtgca    5940
gatatattaa cgtcattatt aggtggagag caagatgcat gatctggtag aaattgtcga    6000
aaacacaaga gagagtgaag tgcacacttc tggtatagga gtgtatacgc cgctggttgg    6060
tgggcaatgc gcgccgcaat attggccaat gaaacctagc aacgcccact cgccacgccc    6120
catgaatggc ccccgcacgg cagcgagcca gccagtgccc gcgcgcggcc cagccggagt    6180
cggcggaacg cgccacgggg gacgaggcgc ccgagggccg aggcagcgcg gcatggcaag    6240
caagccgaag cgggcaagcg acctgcatgc agcccctgcc cctcgccctc gtcagtcgtc    6300
ccagcctccc actggaatcc acccaacccg cccttcctct ccaaagcacg cgccccgcga    6360
ctcgcctccg cctacgtgtc ggcagcgtcc ccgccggtcg cccacgtacc ccgccccgtt    6420
ctcccacgtg cccctccctc tgcgcgcgtc cgattggctg acccgcccctt cttaagccgc    6480 gccagcctcc tgtccgggcc ccaacgccgt gctccgtcgt cgtctccgcc cccagagtga    6540
tcgagcccac tgacctggcc cccgagcctc agctcgtgag tccggcgcgc ctggtgctta    6600
aacactctgg tgagttctag tacttctgct atgatcgatc tcattaccat ttcttaaatt    6660
tctctcccta aatattccga gttcttgatt tttgataact tcaggttttc tcttttgat    6720 aaatctggtc tttccatttt ttttttttg tggttaattt agtttcctat gttcttcgat    6780
tgtattatgc atgatctgtg tttggattct gttagattat gtattggtga atatgtatgt    6840
gtttttgcat gtctggtttt ggtcttaaaa atgttcaaat ctgatgattt gattgaagct    6900 ttttagtgt tggtttgatt cttctcaaaa ctactgttaa tttactatca tgttttccaa    6960
ctttgattca tgatgacact tttgttctgc tttgttataa aatttggtt ggtttgattt    7020 tgtaattata gtgtaatttt gttaggaatg aacatgtttt aatactctgt tttcgatttg    7080
tcacacattc gaattattaa tcgataattt aactgaaaat tcatggttct agatcttgtt    7140
gtcatcagat tatttgtttc gataattcat caaatatgta gtcctttgc tgatttgcga    7200 ctgtttcatt ttttctcaaa attgttttt gttaagttta tctaacagtt atcgttgtca    7260
aaagtctctt tcattttgca aaatcttctt tttttttg tttgtaactt tgttttttaa    7320
gctacacatt tagtctgtaa aatagcatcg aggaacagtt gtcttagtag acttgcatgt    7380
```

-continued

```
tcttgtaact tctatttgtt tcagtttgtt gatgactgct ttgattttgt aggtcaaagg    7440
cgcgccggat ccccgggtgg tcagtcccct atgttacgtc ctgtagaaac cccaacccgt    7500
gaaatcaaaa aactcgacgg cctgtgggca ttcagtctgg atcgcgaaaa ctgtggaatt    7560
gatcagcgtt ggtgggaaag cgcgttacaa gaaagccggg caattgctgt gccaggcagt    7620
tttaacgatc agttcgccga tgcagatatt cgtaattatg cgggcaacgt ctggtatcag    7680
cgcgaagtct ttataccgaa aggttgggca ggccagcgta tcgtgctgcg tttcgatgcg    7740
gtcactcatt acggcaaagt gtgggtcaat aatcaggaag tgatggagca tcagggcggc    7800
tatacgccat tgaagccga tgtcacgccg tatgttattg ccgggaaaag tgtacgtaag     7860
tttctgcttc tacctttgat atatatataa taattatcat taattagtag taatataata    7920
tttcaaatat ttttttcaaa ataaaagaat gtagtatata gcaattgctt ttctgtagtt    7980
tataagtgtg tatattttaa tttataactt ttctaatata tgaccaaaat ttgttgatgt    8040
gcaggtatca ccgtttgtgt gaacaacgaa ctgaactggc agactatccc gccgggaatg    8100
gtgattaccg acgaaaacgg caagaaaaag cagtcttact tccatgattt ctttaactat    8160
gccggaatcc atcgcagcgt aatgctctac accacgccga cacctgggt ggacgatatc     8220
accgtggtga cgcatgtcgc gcaagactgt aaccacgcgt ctgttgactg gcaggtggtg    8280
gccaatggtg atgtcagcgt tgaactgcgt gatgcggatc aacaggtggt tgcaactgga    8340
caaggcacta gcgggacttt gcaagtggtg aatccgcacc tctggcaacc gggtgaaggt    8400
tatctctatg aactgtgcgt cacagccaaa agccagacag agtgtgatat ctacccgctt    8460
cgcgtcggca tccggtcagt ggcagtgaag ggcgaacagt tcctgattaa ccacaaaccg    8520
ttctacttta ctggctttgg tcgtcatgaa gatgcggact tgcgtggcaa aggattcgat    8580
aacgtgctga tggtgcacga ccacgcatta atggactgga ttggggccaa ctcctaccgt    8640
acctcgcatt accttacgc tgaagagatg ctcgactggg cagatgaaca tggcatcgtg     8700
gtgattgatg aaactgctgc tgtcggcttt aacctctctt taggcattgg tttcgaagcg    8760
ggcaacaagc cgaaagaact gtacagcgaa gaggcagtca acggggaaac tcagcaagcg    8820
cacttacagg cgattaaaga gctgatagcg cgtgacaaaa accacccaag cgtggtgatg    8880
tggagtattg ccaacgaacc ggataccgt ccgcaaggtg cacgggaata tttcgcgcca     8940
ctggcggaag caacgcgtaa actcgacccg acgcgtccga tcacctgcgt caatgtaatg    9000
ttctgcgacg ctcacaccga taccatcagc gatctctttg atgtgctgtg cctgaaccgt    9060
tattacggat ggtatgtcca aagcggcgat ttggaaacgg cagagaaggt actgaaaaaa    9120
gaacttctgg cctggcagga gaaactgcat cagccgatta tcatcaccga atacggcgtg    9180
gatacgttag ccgggctgca ctcaatgtac accgacatgt ggagtgaaga gtatcagtgt    9240
gcatggctgg atatgtatca ccgcgtcttt gatcgcgtca gcgccgtcgt cggtgaacag    9300
gtatggaatt cgccgatttt gcgacctcg caaggcatat tgcgcgttgg cggtaacaag     9360
aaagggatct tcactcgcga ccgcaaaccg aagtcggcgg ctttctgct gcaaaaacgc     9420
tggactggca tgaacttcgg tgaaaaaccg cagcagggag gcaaacaatg aatcaacaac    9480
tctcctggcg caccatcgtc ggctacagcc tcgggaattg ctaccgagct cctgcaggcc    9540
taggatcgtt caaacatttg gcaataaagt ttcttaagat tgaatcctgt tgccggtctt    9600
gcgatgatta tcatataatt tctgttgaat tacgttaagc atgtaataat taacatgtaa    9660
tgcatgacgt tatttatgag atgggttttt atgattagag tcccgcaatt atacatttaa    9720
tacgcgatag aaaacaaaat atagcgcgca aactaggata aattatcgcg cgcggtgtca    9780
```

```
tctatgttac tagatcggcc ggccgtttaa acttagttac taatcagtga tcagattgtc    9840
gtttcccgcc ttcactttaa actatcagtg tttgacagga tatattggcg ggtaaaccta    9900
agagaaaaga gcgtttatta gaataatcgg atatttaaaa gggcgtgaaa aggtttatcc    9960
gttcgtccat ttgtatgtca atattggggg gggggaaag ccacgttgtg tctcaaaatc     10020
tctgatgtta cattgcacaa gataaaaata tatcatcatg aacaataaaa ctgtctgctt    10080
acataaacag taatacaagg ggtgttcgcc accatgagcc atatccagcg tgaaacctcg    10140
tgctcccgcc cgcgcctcaa ttccaatatg gatgccgacc tttatggcta caagtgggcg    10200
cgcgacaacg tcgccagtc gggcgcgacc atttatcggc tttatggcaa acccgatgcc     10260
ccggaactgt tcctgaagca cggcaaaggc agcgtcgcaa acgatgtcac cgatgagatg    10320
gtccgcctga actggcttac cgagttcatg ccgctgccga cgattaagca tttcatccgt    10380
accccggacg atgcctggct cttgaccacg gccattccgg gcaaaacggc ctttcaggtc    10440
cttgaagagt acccggactc cggtgagaat atcgtggacg ccctcgcggt cttcctccgc    10500
cgtttgcata gcatccccgt gtgcaactgc cccttcaact cggaccgggt tttccgcctg    10560
gcacaggccc agtcgcgcat gaataacggc ctcgttgacg cgagcgattt cgacgatgaa    10620
cggaatggct ggccggtgga acaggtttgg aaggaaatgc acaaactgct tccgttctcg    10680
ccggattcgg tggtcacgca tggtgatttt tccctggata atctgatctt tgacgagggc    10740
aagctgatcg gctgcatcga cgtgggtcgc gtcggtatcg ccgaccgcta tcaggacctg    10800
gcgatcttgt ggaattgcct cggcgagttc tcgccctcgc tccagaagcg cctgttccag    10860
aagtacggca tcgacaaccc ggatatgaac aagctccagt tccacctcat gctggacgaa    10920
ttttttttgaa cagaattggt taattggttg taacactggc agagcattac gctgacttga    10980
cgggacggcg gctttgttga ataaatcgaa cttttgctga gttgaaggat cgatgagttg    11040
aaggaccccg tagaaaagat caaaggatct tcttgagatc ctttttttct gcgcgtaatc    11100
tgctgcttgc aaacaaaaaa accaccgcta ccagcggtgg tttgtttgcc ggatcaagag    11160
ctaccaactc ttttccgaa ggtaactggc ttcagcagag cgcagatacc aaatactgtc     11220
cttctagtgt agccgtagtt aggccaccac ttcaagaact ctgtagcacc gcctacatac    11280
ctcgctctgc taatcctgtt accagtggct gctgccagtg gcgataagtc gtgtcttacc    11340
gggttggact caagacgata gttaccggat aaggcgcagc ggtcgggctg aacggggggt    11400
tcgtgcacac agcccagctt ggagcgaacg acctacaccg aactgagata cctacagcgt    11460
gagctatgag aaagcgccac gcttcccgaa gggagaaagg cggacaggta tccggtaagc    11520
ggcagggtcg gaacaggaga gcgcacgagg gagcttccag ggggaaacgc ctggtatctt    11580
tatagtcctg tcgggtttcg ccacctctga cttgagcgtc gatttttgtg atgctcgtca    11640
gggggggcgga gcctatggaa aaacgccagc aacgcggcct ttttacggtt cctggccttt    11700
tgctggcctt ttgctcacat gttctttcct gcgttatccc ctgattctgt ggataaccgt    11760
attaccgcct ttgagtgagc tgataccgct cgccgcagcc gaacgaccga gcgcagcgag    11820
tcagtgagcg aggaagcgga agagcgcctg atgcggtatt ttctccttac gcatctgtgc    11880
ggtatttcac accgcatagg ccgcgatagg ccgacgcgaa gcggcgggc gtaggagcg     11940
cagcgaccga agggtaggcg cttttttgcag ctcttcggct gtgcgctggc cagacagtta   12000
tgcacaggcc aggcgggttt taagagtttt aataagtttt aaagagtttt aggcggaaaa    12060
atcgcctttt ttctcttta tatcagtcac ttacatgtgt gaccggttcc caatgtacgg     12120
```

-continued

```
ctttgggttc caatgtacg ggttccggtt cccaatgtac ggctttgggt tcccaatgta    12180
cgtgctatcc acaggaaaga gacctttcg accttttcc cctgctaggg caatttgccc     12240
tagcatctgc tccgtacatt aggaaccggc ggatgcttcg ccctcgatca ggttgcggta   12300
gcgcatgact aggatcgggc cagcctgccc cgcctcctcc ttcaaatcgt actccggcag   12360
gtcatttgac ccgatcagct tgcgcacggt gaaacagaac ttcttgaact ctccggcgct   12420
gccactgcgt tcgtagatcg tcttgaacaa ccatctggct tctgccttgc ctgcggcgcg   12480
gcgtgccagg cggtagagaa acggccgat gccggggtcg atcaaaaagt aatcggggtg    12540
aaccgtcagc acgtccgggt tcttgccttc tgtgatctcg cggtacatcc aatcagcaag   12600
ctcgatctcg atgtactccg gccgcccggt ttcgctcttt acgatcttgt agcggctaat   12660
caaggcttca ccctcggata ccgtcaccag gcggccgttc ttggccttct tggtacgctg   12720
catggcaacg tgcgtggtgt ttaaccgaat gcaggtttct accaggtcgt cttctgctt    12780 tccgccatcg gctcgccggc agaacttgag tacgtccgca acgtgtggac ggaacacgcg   12840
gccgggcttg tctcccttcc cttcccggta tcggttcatg gattcggtta gatgggaaac   12900
cgccatcagt accaggtcgt aatcccacac actggccatg ccggcggggc ctgcggaaac   12960
ctctacgtgc ccgtctggaa gctcgtagcg gatcacctcg ccagctcgtc ggtcacgctt   13020
cgacagacgg aaaacggcca cgtccatgat gctgcgacta tcgcgggtgc ccacgtcata   13080
gagcatcgga acgaaaaaat ctggttgctc gtcgcccttg gcggcttcc taatcgacgg    13140 cgcaccggct gccggcggtt gccgggattc tttgcggatt cgatcagcgg ccccttgcca   13200
cgattcaccg gggcgtgctt ctgcctcgat gcgttgccgc tgggcggcct gcgcggcctt   13260
caacttctcc accaggtcat cacccagcgc cgcgccgatt tgtaccgggc cggatggttt   13320
gcgaccgctc acgccgattc ctcgggcttg ggggttccag tgccattgca gggccggcag   13380
acaacccagc cgcttacgcc tggccaaccg cccgttcctc cacacatggg gcattccacg   13440
gcgtcggtgc ctggttgttc ttgattttcc atgccgcctc ctttagccgc taaaattcat   13500
ctactcattt attcatttgc tcatttactc tggtagctgc gcgatgtatt cagatagcag   13560
ctcggtaatg gtcttgcctt ggcgtaccgc gtacatcttc agcttggtgt gatcctccgc   13620
cggcaactga aagttgaccc gcttcatggc tggcgtgtct gccaggctgg ccaacgttgc   13680
agccttgctg ctgcgtgcgc tcggacggcc ggcacttagc gtgtttgtgc ttttgctcat   13740
tttctcttta cctcattaac tcaaatgagt tttgatttaa tttcagcggc cagcgcctgg   13800
acctcgcggg cagcgtcgcc ctcgggttct gattcaagaa cggttgtgcc ggcggcggca   13860
gtgcctgggt agctcacgcg ctgcgtgata cgggactcaa gaatgggcag ctcgtacccg   13920
gccagcgcct cggcaacctc accgccgatg cgcgtgcctt tgatcgcccg cgacacgaca   13980
aaggccgctt gtagccttcc atccgtgacc tcaatgcgct gcttaaccag ctccaccagg   14040
tcggcggtgg cccaaatgtc gtaagggctt ggctgcaccg gaatcagcac gaagtcggct   14100
gccttgatcg cggacacagc caagtccgcc gcctggggcg ctccgtcgat cactacgaag   14160
tcgcgccggc cgatggcctt cacgtcgcgg tcaatcgtcg ggcggtcgat gccgacaacg   14220
gttagcggtt gatcttcccg cacggccgcc caatcgcggg cactgccctg gggatcggaa   14280
tcgactaaca gaacatcggc cccggcgagt tgcagggcgc gggctagatg ggttgcgatg   14340
gtcgtcttgc ctgacccgcc tttctggtta agtacagcga taaccttcat gcgttcccct   14400
tgcgtatttg tttatttact catcgcatca tatacgcagc gaccgcatga cgcaagctgt   14460
tttactcaaa tacacatcac cttttagat gatca                              14495
```

<210> SEQ ID NO 83
<211> LENGTH: 33
<212> TYPE: DNA
<213> ORGANISM: Artificial Sequence
<220> FEATURE:
<223> OTHER INFORMATION: synthetic sequence

<400> SEQUENCE: 83
atatacgcgt ggtgcttaaa cactctggtg agt                                    33

<210> SEQ ID NO 84
<211> LENGTH: 38
<212> TYPE: DNA
<213> ORGANISM: Artificial Sequence
<220> FEATURE:
<223> OTHER INFORMATION: synthetic sequence

<400> SEQUENCE: 84
atatggcgcg cctttgacct acaaaatcaa agcagtca                               38

<210> SEQ ID NO 85
<211> LENGTH: 32
<212> TYPE: DNA
<213> ORGANISM: Artificial Sequence
<220> FEATURE:
<223> OTHER INFORMATION: synthetic sequence

<400> SEQUENCE: 85
atatacgcgt agttctttgc tttcgaagtt gc                                     32

<210> SEQ ID NO 86
<211> LENGTH: 35
<212> TYPE: DNA
<213> ORGANISM: Artificial Sequence
<220> FEATURE:
<223> OTHER INFORMATION: synthetic sequence

<400> SEQUENCE: 86
atatggcgcg cctactacgt actgttttca attct                                  35

<210> SEQ ID NO 87
<211> LENGTH: 14065
<212> TYPE: DNA
<213> ORGANISM: Artificial Sequence
<220> FEATURE:
<223> OTHER INFORMATION: vector sequence

<400> SEQUENCE: 87
gtgattttgt gccgagctgc cggtcgggga gctgttggct ggctggtggc aggatatatt        60
gtggtgtaaa caaattgacg cttagacaac ttaataacac attgcggacg tctttaatgt       120
actgaattta gttactgatc actgattaag tactgatatc ggtaccaagc ttccgcggct       180
gcagtgcagc gtgacccggt cgtgccccte tctagagata atgagcattg catgtctaag       240
ttataaaaaa ttaccacata ttttttttgt cacacttgtt tgaagtgcag tttatctatc       300
tttatacata tatttaaact ttactctacg aataatataa tctatagtac tacaataata       360
tcagtgtttt agagaatcat ataaatgaac agttagacat ggtctaaagg acaattgagt       420
attttgacaa caggactcta cagttttatc tttttagtgt gcatgtgttc tcctttttt        480 ttgcaaatag cttcacctat ataatacttc atccatttta ttagtacatc catttagggt       540
ttagggttaa tggtttttat agactaattt ttttagtaca tctatttat tctattttag       600

| | |
|---|---|
| cctctaaatt aagaaaacta aaactctatt ttagtttttt tatttaatag tttagatata | 660 |
| aaatagaata aaataaagtg actaaaaatt aaacaaatac cctttaagaa attaaaaaaa | 720 |
| ctaaggaaac atttttcttg tttcgagtag ataatgccag cctgttaaac gccgtcgacg | 780 |
| agtctaacgg acaccaacca gcgaaccagc agcgtcgcgt cgggccaagc gaagcagacg | 840 |
| gcacggcatc tctgtcgctg cctctggacc cctctcgaga gttccgctcc accgttggac | 900 |
| ttgctccgct gtcggcatcc agaaattgcg tggcggagcg gcagacgtga gccggcacgg | 960 |
| caggcggcct cctcctcctc tcacggcacc ggcagctacg ggggattcct ttcccaccgc | 1020 |
| tccttcgctt tcccttcctc gcccgccgta ataaatagac accccctcca caccctcttt | 1080 |
| ccccaacctc gtgttgttcg gagcgcacac acacacaacc agatctcccc caaatccacc | 1140 |
| cgtcggcacc tccgcttcaa ggtacgccgc tcgtcctccc ccccccccc cctctctacc | 1200 |
| ttctctagat cggcgttccg gtccatggtt agggcccggt agttctactt ctgttcatgt | 1260 |
| ttgtgttaga tccgtgtttg tgttagatcc gtgctgctag cgttcgtaca cggatgcgac | 1320 |
| ctgtacgtca gacacgttct gattgctaac ttgccagtga ttctcttttgg ggaatcctgg | 1380 |
| gatggctcta gccgttccgc agacgggatc gatttcatga tttttttttgt ttcgttgcat | 1440 |
| agggtttggt ttgccctttt cctttatttc aatatatgcc gtgcacttgt ttgtcgggtc | 1500 |
| atcttttcat gcttttttt gtcttggttg tgatgatgtg gtctggttgg gcggtcgttc | 1560 |
| tagatcggag tagaattctg tttcaaacta cctggtggat ttattaattt tggatctgta | 1620 |
| tgtgtgtgcc atacatattc atagttacga attgaagatg atggatggaa atatcgatct | 1680 |
| aggataggta tacatgttga tgcgggtttt actgatgcat atacagagat gcttttttgtt | 1740 |
| cgcttggttg tgatgatgtg gtgtggttgg gcggtcgttc attcgttcta gatcggagta | 1800 |
| gaatactgtt tcaaactacc tggtgtattt attaattttg gaactgtatg tgtgtgtcat | 1860 |
| acatcttcat agttacgagt ttaagatgga tggaaatatc gatctaggat aggtatacat | 1920 |
| gttgatgtgg gttttactga tgcatataca tgatggcata tgcagcatct attcatatgc | 1980 |
| tctaaccttg agtacctatc tattataata aacaagtatg ttttataatt atttcgatct | 2040 |
| tgatatactt ggatgatggc atatgcagca gctatatgtg gattttttta gccctgcctt | 2100 |
| catacgctat ttatttgctt ggtactgttt cttttgtcga tgctcaccct gttgtttggt | 2160 |
| gttacttctg cagcccgggg gatccactag ttctagaaac catggccacc gccgccgccg | 2220 |
| cgtctaccgc gctcactggc gccactaccg ctgcgcccaa ggcgaggcgc cgggcgcacc | 2280 |
| tcctggccac ccgccgcgcc ctcgccgcgc ccatcaggtg ctcagcggcg tcacccgcca | 2340 |
| tgccgatggc tcccccggcc acccgctcc ggccgtgggg cccaccgat ccccgcaagg | 2400 |
| gcgccgacat cctcgtcgag tccctcgagc gctgcggcgt ccgcgacgtc ttcgcctacc | 2460 |
| ccggcggcac gtccatggag atccaccagg cactcacccg ctcccccgtc atcgccaacc | 2520 |
| acctcttccg ccacgagcaa ggggaggcct ttgcggcctc cggctacgcg cgctcctcgg | 2580 |
| gccgcgtcgg cgtctgcatc gccacctccg gccccgcgc caccaaccctt gtctccgcgc | 2640 |
| tcgccgacgc gctgctcgat tccgtcccca tggtcgccat cacgggacag gtgccgcgac | 2700 |
| gcatgattgg caccgacgcc ttccaggaga cgcccatcgt cgaggtcacc cgctccatca | 2760 |
| ccaagcacaa ctacctggtc ctcgacgtcg acgacatccc ccgcgtcgtg caggaggctt | 2820 |
| tcttcctcgc ctcctctggt cgaccggggc cggtgcttgt cgacatcccc aaggacatcc | 2880 |
| agcagcagat ggcggtgcct gtctgggaca agcccatgag tctgcctggg tacattgcgc | 2940 |
| gccttcccaa gccccctgcg actgagttgc ttgagcaggt gctgcgtctt gttggtgaat | 3000 |

```
cccggcgccc tgttctttat gttggcggtg gctgcgcagc atctggtgag gagttgcgac      3060
gctttgtgga gctgactgga atcccggtca caactactct tatgggcctc ggcaacttcc      3120
ccagcgacga cccactgtct ctgcgcatgc taggtatgca tggcacggtg tatgcaaatt      3180
atgcagtgga taaggccgat ctgttgcttg cacttggtgt gcggtttgat gatcgtgtga      3240
cagggaagat tgaggctttt gcaagcaggg ctaagattgt gcacgttgat attgatccgg      3300
ctgagattgg caagaacaag cagccacatg tgtccatctg tgcagatgtt aagcttgctt      3360
tgcagggcat gaatgctctt cttgaaggaa gcacatcaaa gaagagcttt gactttggct      3420 catgaacga tgagttggat cagcagaaga gggaattccc ccttgggtat aaaacatcta      3480
atgaggagat ccagccacaa tatgctattc aggttcttga tgagctgacg aaaggcgagg      3540
ccatcatcgg cacaggtgtt gggcagcacc agatgtgggc ggcacagtac tacacttaca      3600
agcggccaag gcagtggttg tcttcagctg gtcttggggc tatgggattt ggtttgccgg      3660
ctgctgctgg tgcttctgtg gccaacccag gtgttactgt tgttgacatc gatggagatg      3720
gtagctttct catgaacgtt caggagctag ctatgatccg aattgagaac ctcccggtga      3780
aggtctttgt gctaaacaac cagcacctgg ggatggtggt gcagtgggag gacaggttct      3840
ataaggccaa cagagcgcac acatacttgg gaaacccaga gaatgaaagt gagatatatc      3900
cagatttcgt gacgatcgcc aaagggttca acattccagc ggtccgtgtg acaaagaaga      3960
acgaagtccg cgcagcgata aagaagatgc tcgagactcc agggccgtac ctcttggata      4020
taatcgtccc acaccaggag catgtgttgc ctatgatccc taatggtggg gctttcaagg      4080
atatgatcct ggatggtgat ggcaggactg tgtactgatc taaaatccag caagcaactg      4140
atctaaaatc cagcaagcac cgcctccctg ctagtacaag ggtgatatgt ttttatctgt      4200
gtgatgttct cctgtattct atcttttttt gtaggccgtc agctatctgt tatggtaatc      4260
ctatgtagct tccgacccttg taattgtgta gtctgttgtt ttccttctgg catgtgtcat      4320
aagagatcat ttaagtgcct tttgctacat ataaataaga taataagcac tgctatgcag      4380
tggttctgaa ttggcttctg ttgccaaatt taagtgtcca actggtcctt gcttttgttt      4440
tcgctatttt tttcctttt tagttattat tatattggta atttcaactc aacatatgat      4500
gtatggaata atgctagggc tgcaatttca aactatttta caaaccagaa tggcattttc      4560
gtggtttgag gggagtgaaa aaaaatgagg catttgactg aattagttac ctgatccatt      4620
ttcgtggttt ggatcattgg aattaaattc cattctaata atagtaattt tggcatatat      4680
caattaagtt aattcggttt tatgcaaaat atatttgtat actattatta tcaagatgtc      4740
ggagatattt atatgctaca tttttactat acaggagtga gatgaagagt gtcatgtaag      4800
ttacacagta gaaacaaatt ctattaatgc ataaaatcat ttccatcatc caccctatga      4860
atttgagata gacctatatc taaactttga aaagtggttg aatatcaaat tccaaattaa      4920
ataagttatt ttattgagtg aattctaatt tctctaaaac gaagggatct aaacgccctc      4980
taaagctaat ttgaaactc aaactttctt agcattggag gggattgaga aaaaatatta      5040
attcattttc atctcaatca ttcaatctcc aaagagattt gagttcctta ttagtctgtt      5100
ccatgcatca aatcggctca atgtgtcatt atttgccatg acgattgacg agttgttctg      5160
gggcctagcg cttttccacgc cgatgtgctg gggcctggtc ctggagaaga cagcttgata      5220
tttaaagcta tcaattgttt caattgattc ccacttcatt tttctaaatg tagaaaacgg      5280
tgacgtataa gaaaaagaat gaattaggac ttttattccg tacactaatc tagagcggcc      5340
```

```
caagcttgta cactagtacg cgtcaattga tttaaattta attaatcccg tgtccgtcaa    5400
tgtgatacta ctagcatagt actagtacca tgcatacaca cagcaggtcg gccgcctgga    5460
tggatcgatg atgatactac atcatcctgt catccatcca ggcgatctag aaggggcgtg    5520
gctagctagc aaactgtgac cggttttct acgccgataa taatactttg tcatggtaca     5580
gacgtacagt actggttata tatatctgta gatttcaact gaaaagctag gatagctaga    5640
ttaattcctg agaaacacag ataaaattcg agcttggcta tagatgacaa aacgaaagac    5700
gcatgcattg gacgacgtat gcaatgcgag cgcgtctcgt gtcgtcccgt ccaagtctgg    5760
cgatctcacg ccacgtgctc aacagctcaa ggactgttcg tcaccagcgt taaattcatt    5820
gaagggatga cgcatttcgg catttgtcat tgcttgtagc tatatatata tatccaacag    5880
atttctctca agcttttgta tgcgtgaatg taaagtctag cttatacgac agcacgtgca    5940
gatatattaa cgtcattatt aggtggagag caagatgcat gatctggtag aaattgtcga    6000
aaacacaaga gagagtgaag tgcacacttc tggtatagga gtgtatacgc cgctggttgg    6060
tgggcaatgc gcgccgcaat attggccaat gaaacctagc aacgcccact cgccacgccc    6120
catgaatggc ccccgcacgg cagcgagcca gccagtgccc gcgcgcggcc cagccggagt    6180
cggcggaacg cgccacgggg gacgaggcgc ccgagggccg aggcagcgcg gcatggcaag    6240
caagccgaag cgggcaagcg acctgcatgc agccctgcc cctcgccctc gtcagtcgtc     6300
ccagcctccc actggaatcc acccaacccg cccttcctct ccaaagcacg cgccccgcga    6360
ctcgcctccg cctacgtgtc ggcagcgtcc ccgccggtcg cccacgtacc ccgccccgtt    6420
ctcccacgtg cccctccctc tgcgcgcgtc cgattggctg acccgcccctt cttaagccgc    6480
gccagcctcc tgtccgggcc ccaacgccgt gctccgtcgt cgtctccgcc cccagagtga    6540
tcgagcccac tgacctggcc cccgagcctc agctcgtgag tccggcgcgt ggtgcttaaa    6600
cactctggtg agttctagta cttctgctat gatcgatctc attaccattt cttaaatttc    6660
tctccctaaa tattccgagt tcttgatttt tgataacttc aggttttctc tttttgataa    6720
atctggtctt tccattttt ttttttgtg gttaatttag tttcctatgt tcttcgattg      6780
tattatgcat gatctgtgtt tggattctgt tagattatgt attggtgaat atgtatgtgt    6840
ttttgcatgt ctggttttgg tcttaaaaat gttcaaatct gatgatttga ttgaagcttt    6900
tttagtgttg gtttgattct tctcaaaact actgttaatt tactatcatg ttttccaact    6960
ttgattcatg atgacacttt tgttctgctt tgttataaaa ttttggttgg tttgattttg    7020
taattatagt gtaattttgt taggaatgaa catgttttaa tactctgttt tcgatttgtc    7080
acacattcga attattaatc gataatttaa ctgaaaattc atggttctag atcttgttgt    7140
catcagatta tttgtttcga taattcatca aatatgtagt cctttttgctg atttgcgact   7200
gtttcatttt ttctcaaaat tgttttttgt taagtttatc taacagttat cgttgtcaaa    7260
agtctctttc atttttgcaaa atcttctttt ttttttttgtt tgtaactttg tttttttaagc    7320
tacacattta gtctgtaaaa tagcatcgag gaacagttgt cttagtagac ttgcatgttc    7380
ttgtaacttc tatttgtttc agtttgttga tgactgcttt gattttgtag gtcaaaggcg    7440
cgccaccatg aagacgcca aaaacataaa gaaaggcccg cgccattct atccgctgga     7500
agatggaacc gctggagagc aactgcataa ggctatgaag agatacgccc tggttcctgg    7560
aacaattgct tttacagatg cacatatcga ggtggacatc acttacgctg agtacttcga    7620
aatgtccgtt cggttggcag aagctatgaa acgatatggg ctgaatacaa atcacagaat    7680
cgtcgtatgc agtgaaaact ctcttcaatt ctttatgccg gtgttgggcg cgttatttat    7740
```

```
cggagttgca gttgcgcccg cgaacgacat ttataatgaa cgtgaattgc tcaacagtat   7800
gggcatttcg cagcctaccg tggtgttcgt ttccaaaaag gggttgcaaa aaatttttgaa  7860
cgtgcaaaaa aagctcccaa tcatccaaaa aattattatc atggattcta aaacggatta   7920
ccagggattt cagtcgatgt acacgttcgt cacatctcat ctacctcccg gttttaatga   7980
atacgatttt gtgccagagt ccttcgatag ggacaagaca attgcactga tcatgaactc   8040
ctctggatct actggtctgc ctaaaggtgt cgctctgcct catagaactg cctgcgtgag   8100
attctcgcat gccagagatc ctattttttgg caatcaaatc attccggata ctgcgatttt   8160
aagtgttgtt ccattccatc acggttttgg aatgtttact acactcggat atttgatatg   8220
tggatttcga gtcgtcttaa tgtatagatt tgaagaagag ctgtttctga ggagccttca   8280
ggattacaag attcaaagtg cgctgctggt gccaacccta ttctccttct tcgccaaaag   8340
cactctgatt gacaaatacg atttatctaa tttacacgaa attgcttctg gtggcgctcc   8400
cctctctaag gaagtcgggg aagcggttgc caagaggttc catctgccag gtatcaggca   8460
aggatatggg ctcactgaga ctacatcagc tattctgatt acacccgagg gggatgataa   8520
accgggcgcg gtcggtaaag ttgttccatt ttttgaagcg aaggttgtgg atctggatac   8580
cgggaaaacg ctgggcgtta atcaaagagg cgaactgtgt gtgagaggtc ctatgattat   8640
gtccggttat gtaaacaatc cggaagcgac caacgccttg attgacaagg atggatggct   8700
acattctgga gacatagctt actgggacga agacgaacac ttcttcatcg ttgaccgcct   8760
gaagtctctg attaagtaca aaggctatca ggtggctccc gctgaattgg aatccatctt   8820
gctccaacac cccaacatct tcgacgcagg tgtcgcaggt cttcccgacg atgacgccgg   8880
tgaacttccc gccgccgttg ttgtttttgga gcacggaaag acgatgacgg aaaaagagat   8940
cgtggattac gtcgccagtc aagtaacaac cgcgaaaaag ttgcgcggag gagttgtgtt   9000
tgtggacgaa gtaccgaaag gtcttaccgg aaaactcgac gcaagaaaaa tcagagagat   9060
cctcataaag gccaagaagg gcggaaagat cgccgtgtaa cctgcaggcc taggatcgtt   9120
caaacatttg gcaataaagt ttcttaagat tgaatcctgt tgccggtctt gcgatgatta   9180
tcatataatt tctgttgaat tacgttaagc atgtaataat taacatgtaa tgcatgacgt   9240
tatttatgag atgggttttt atgattagag tcccgcaatt atacatttaa tacgcgatag   9300
aaaacaaaat atagcgcgca aactaggata aattatcgcg cgcggtgtca tctatgttac   9360
tagatcggcc ggccgtttaa acttagttac taatcagtga tcagattgtc gtttcccgcc   9420
ttcactttaa actatcagtg tttgacagga tatattggcg ggtaaaccta agagaaaaga   9480
gcgtttatta gaataatcgg atatttaaaa gggcgtgaaa aggtttatcc gttcgtccat   9540
ttgtatgtca atattggggg gggggaaag ccacgttgtg tctcaaaatc tctgatgtta   9600
cattgcacaa gataaaaata tatcatcatg aacaataaaa ctgtctgctt acataaacag   9660
taatacaagg ggtgttcgcc accatgagcc atatccagcg tgaaacctcg tgctcccgcc   9720
cgcgcctcaa ttccaatatg gatgccgacc tttatggcta caagtgggcg cgcgacaacg   9780
tcggccagtc gggcgcgacc atttatcggc tttatggcaa acccgatgcc ccggaactgt   9840
tcctgaagca cggcaaaggc agcgtcgcaa acgatgtcac cgatgagatg gtccgcctga   9900
actggcttac cgagttcatg ccgctgccga cgattaagca tttcatccgt accccggacg   9960
atgcctggct cttgaccacg gccattccgg gcaaaacggc ctttcaggtc cttgaagagt  10020
acccggactc cggtgagaat atcgtggacg ccctcgcggt cttcctccgc cgtttgcata 10080
```

```
gcatccccgt gtgcaactgc cccttcaact cggaccgggt tttccgcctg cacaggccc    10140 agtcgcgcat gaataacggc ctcgttgacg cgagcgattt cgacgatgaa cggaatggct   10200
ggccggtgga acaggtttgg aaggaaatgc acaaactgct tccgttctcg ccggattcgg   10260
tggtcacgca tggtgatttt tccctggata atctgatctt tgacgagggc aagctgatcg   10320
gctgcatcga cgtgggtcgc gtcggtatcg ccgaccgcta tcaggacctg gcgatcttgt   10380
ggaattgcct cggcgagttc tcgccctcgc tccagaagcg cctgttccag aagtacggca   10440
tcgacaaccc ggatatgaac aagctccagt tccacctcat gctggacgaa ttttttttgaa  10500 cagaattggt taattggttg taacactggc agagcattac gctgacttga cgggacggcg   10560
gctttgttga ataaatcgaa cttttgctga gttgaaggat cgatgagttg aaggaccccg   10620
tagaaaagat caaggatct tcttgagatc cttttttttct gcgcgtaatc tgctgcttgc    10680
aaacaaaaaa accaccgcta ccagcggtgg tttgtttgcc ggatcaagag ctaccaactc   10740 ttttttccgaa ggtaactggc ttcagcagag cgcagatacc aaatactgtc cttctagtgt  10800
agccgtagtt aggccaccac ttcaagaact ctgtagcacc gcctacatac ctcgctctgc   10860
taatcctgtt accagtggct gctgccagtg gcgataagtc gtgtcttacc gggttggact   10920
caagacgata gttaccggat aaggcgcagc ggtcgggctg aacggggggt tcgtgcacac   10980
agcccagctt ggagcgaacg acctacaccg aactgagata cctacagcgt gagctatgag   11040
aaagcgccac gcttcccgaa gggagaaagg cggacaggta tccggtaagc ggcagggtcg   11100
gaacaggaga gcgcacgagg gagcttccag ggggaaacgc ctggtatctt tatagtcctg   11160
tcgggtttcg ccacctctga cttgagcgtc gatttttgtg atgctcgtca gggggcgga    11220 gcctatggaa aaacgccagc aacgcggcct ttttacggtt cctggccttt tgctggcctt    11280
ttgctcacat gttctttcct gcgttatccc ctgattctgt ggataaccgt attaccgcct   11340
ttgagtgagc tgataccgct cgccgcagcc gaacgaccga gcgcagcgag tcagtgagcg   11400
aggaagcgga gagcgcctg atgcggtatt ttctccttac gcatctgtgc ggtatttcac    11460
accgcatagg ccgcgatagg ccgacgcgaa gcggcgggc gtagggagcg cagcgaccga    11520
agggtaggcg cttttttgcag ctcttcggct gtgcgctggc cagacagtta tgcacaggcc   11580
aggcgggttt taagagtttt aataagtttt aaagagtttt aggcggaaaa atcgcctttt   11640
ttctctttta tatcagtcac ttacatgtgt gaccggttcc caatgtacgg ctttgggttc   11700
ccaatgtacg ggttccggtt cccaatgtac ggctttgggt tcccaatgta cgtgctatcc   11760
acaggaaaga gaccttttcg acctttttcc cctgctaggg caatttgccc tagcatctgc   11820
tccgtacatt aggaaccggc ggatgcttcg ccctcgatca ggttgcggta gcgcatgact   11880
aggatcgggc cagcctgccc cgcctcctcc ttcaaatcgt actccggcag gtcatttgac   11940
ccgatcagct tgcgcacggt gaaacagaac ttcttgaact ctccggcgct gccactgcgt   12000
tcgtagatcg tcttgaacaa ccatctggct tctgccttgc ctgcggcgcg cgtgccagg    12060 cggtagagaa acggccgat gccggggtcg atcaaaaagt aatcggggtg aaccgtcagc    12120
acgtccgggt tcttgccttc tgtgatctcg cggtacatcc aatcagcaag ctcgatctcg   12180
atgtactccg gccgcccggt ttcgctcttt acgatcttgt agcggctaat caaggcttca   12240
ccctcggata ccgtcaccag gcggccgttc ttggccttct tggtacgctg catggcaacg   12300
tgcgtggtgt ttaaccgaat gcaggtttct accaggtcgt cttttctgctt tccgccatcg   12360 gctcgccggc agaacttgag tacgtccgca acgtgtggac ggaacacgcg gccgggcttg   12420
tctcccttcc cttcccggta tcggttcatg gattcggtta gatgggaaac cgccatcagt   12480
```

```
accaggtcgt aatcccacac actggccatg ccggcggggc ctgcggaaac ctctacgtgc    12540
ccgtctggaa gctcgtagcg gatcacctcg ccagctcgtc ggtcacgctt cgacagacgg    12600
aaaacggcca cgtccatgat gctgcgacta tcgcgggtgc ccacgtcata gagcatcgga    12660
acgaaaaaat ctggttgctc gtcgcccttg ggcggcttcc taatcgacgg cgcaccggct    12720
gccggcggtt gccgggattc tttgcggatt cgatcagcgg ccccttgcca cgattcaccg    12780
gggcgtgctt ctgcctcgat gcgttgccgc tgggcggcct gcgcggcctt caacttctcc    12840
accaggtcat cacccagcgc cgcgccgatt tgtaccgggc cggatggttt gcgaccgctc    12900
acgccgattc ctcgggcttg ggggttccag tgccattgca gggccggcag acaacccagc    12960
cgcttacgcc tggccaaccg cccgttcctc cacacatggg gcattccacg gcgtcggtgc    13020
ctggttgttc ttgattttcc atgccgcctc ctttagccgc taaaattcat ctactcattt    13080
attcatttgc tcatttactc tggtagctgc gcgatgtatt cagatagcag ctcggtaatg    13140
gtcttgcctt ggcgtaccgc gtacatcttc agcttggtgt gatcctccgc cggcaactga    13200
aagttgaccc gcttcatggc tggcgtgtct gccaggctgg ccaacgttgc agccttgctg    13260
ctgcgtgcgc tcggacggcc ggcacttagc gtgtttgtgc ttttgctcat tttctcttta    13320
cctcattaac tcaaatgagt tttgatttaa tttcagcggc cagcgcctgg acctcgcggg    13380
cagcgtcgcc ctcgggttct gattcaagaa cggttgtgcc ggcggcggca gtgcctgggt    13440
agctcacgcg ctgcgtgata cgggactcaa gaatgggcag ctcgtacccg gccagcgcct    13500
cggcaacctc accgccgatg cgcgtgcctt tgatcgcccg cgacacgaca aaggccgctt    13560
gtagccttcc atccgtgacc tcaatgcgct gcttaaccag ctccaccagg tcggcggtgg    13620
cccaaatgtc gtaagggctt ggctgcaccg gaatcagcac gaagtcggct gccttgatcg    13680
cggacacagc caagtccgcc gcctggggcg ctccgtcgat cactacgaag tcgcgccggc    13740
cgatggcctt cacgtcgcgg tcaatcgtcg ggcggtcgat gccgacaacg gttagcggtt    13800
gatcttcccg cacggccgcc caatcgcggg cactgccctg gggatcggaa tcgactaaca    13860
gaacatcggc cccggcgagt tgcagggcgc gggctagatg ggttgcgatg gtcgtcttgc    13920
ctgacccgcc tttctggtta agtacagcga taaccttcat gcgttcccct tgcgtatttg    13980
tttatttact catcgcatca tatacgcagc gaccgcatga cgcaagctgt tttactcaaa    14040
tacacatcac cttttagat gatca                                            14065
```

REGULATORY NUCLEIC ACID MOLECULES FOR ENHANCING SEED-SPECIFIC AND/OR SEED-PREFERENTIAL GENE EXPRESSION IN PLANTS

RELATED APPLICATIONS

This application is a national stage application (under 35 U.S.C. §371) of PCT/EP2010/061661, filed Aug. 11, 2010 which claims benefit of U.S. Provisional Application No. 61/238,233, filed Aug. 31, 2009 and European Application No. 09169017.2, filed Aug. 31, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13987_00172_US. The size of the text file is 116 KB and the text file was created on Feb. 27, 2012.

The present invention is in the field of plant molecular biology and provides methods for production of high expressing seed-specific and/or seed-preferential promoters and the production of plants with enhanced seed-specific and/or seed-preferential expression of nucleic acids wherein nucleic acid expression enhancing nucleic acids (NEENAs) are functionally linked to said promoters and/or introduced into plants.

Expression of transgenes in plants is strongly affected by various external and internal factors resulting in a variable and unpredictable level of transgene expression. Often a high number of transformants have to be produced and analyzed in order to identify lines with desirable expression strength. As transformation and screening for lines with desirable expression strength is costly and labor intensive there is a need for high expression of one or more transgenes in a plant. This problem is especially pronounced, when several genes have to be coordinately expressed in a transgenic plant in order to achieve a specific effect as a plant has to be identified in which each and every gene is strongly expressed.

For example, expression of a transgene can vary significantly, depending on construct design and positional effects of the T-DNA insertion locus in individual transformation events. Strong promoters can partially overcome these challenges. However, availability of suitable promoters showing strong expression with the desired specificity is often limited. In order to ensure availability of sufficient promoters with desired expression specificity, the identification and characterization of additional promoters can help to close this gap. However, natural availability of promoters of the respective specificity and strength and the time consuming characterization of promoter candidates impedes the identification of suitable new promoters.

In order to overcome these challenges, diverse genetic elements and/or motifs have been shown to positively affect gene expression. Among these, some introns have been recognized as genetic elements with a strong potential for improving gene expression. Although the mechanism is largely unknown, it has been shown that some introns positively affect the steady state amount of mature mRNA, possibly by enhanced transcriptional activity, improved mRNA maturation, enhanced nuclear mRNA export and/or improved translation initiation (e.g. Huang and Gorman, 1990; Le Hir et al., 2003; Nott et al., 2004). Since only selected introns were shown to increase expression, splicing as such is likely not accountable for the observed effects.

The increase of gene expression observed upon functionally linking introns to promoters is called intron mediated enhancement (IME) of gene expression and has been shown in various monocotyledonous (e.g. Callis et al., 1987; Vasil et al., 1989; Bruce et al., 1990; Lu et al., 2008) and dicotyledonous plants (e.g. Chung et al., 2006; Kim et al., 2006; Rose et al., 2008). In this respect, the position of the intron in relation to the translational start site (ATG) was shown to be crucial for intron mediated enhancement of gene expression (Rose et al., 2004).

Next to their potential for enhancing gene expression, few introns were shown to also affect the tissue specificity in their native nucleotide environment in plants. Reporter gene expression was found to be dependent on the presence of genomic regions containing up to two introns (Sieburth et al., 1997; Wang et al., 2004). 5' UTR introns have also been reported to be of importance for proper functionality of promoter elements, likely due to tissue specific gene control elements residing in the introns (Fu et al., 1995a; Fu et al., 1995b; Vitale et al., 2003; Kim et al., 2006). However, these studies also show that combination of introns with heterologous promoters can have strong negative impacts on strength and/or specificity of gene expression (Vitale et al., 2003; Kim et al., 2006, WO2006/003186, WO2007/098042). For example the strong constitutive Cauliflower Mosaic Virus CaMV35S promoter is negatively affected through combination with the sesame SeFAD2 5'UTR intron (Kim et al., 2006). In contrast to these observations, some documents show enhanced expression of a nucleic acid by IME without affecting the tissue specificity of the respective promoter (Schünmann et al., 2004). Introns or NEENAs that enhance seed-specific and/or seed-preferential expression when functionally linked to a heterologous promoter have not been shown in the art.

In the present application further nucleic acid molecules are described that enhance the expression of said promoters without affecting their specificity upon functionally linkage to seed-specific and/or seed-preferential promoters. These nucleic acid molecules are in the present application described as "nucleic acid expression enhancing nucleic acids" (NEENA). Introns have the intrinsic feature to be spliced out of the respective pre-mRNA. In contrast to that the nucleic acids presented in the application at hand, do not necessarily have to be included in the mRNA or, if present in the mRNA, have not necessarily to be spliced out of the mRNA in order to enhance the expression derived from the promoter the NEENAs are functionally linked to.

DETAILED DESCRIPTION OF THE INVENTION

A first embodiment of the invention comprises a method for production of a high expression seed-specific and/or seed-preferential promoter comprising functionally linking to a promoter one or more nucleic acid expression enhancing nucleic acid (NEENA) molecule comprising
i) the nucleic acid molecule having a sequence as defined in any of SEQ ID NO: 1 to 15, or
ii) a nucleic acid molecule having a sequence with an identity of 80% or more to any of the sequences as defined by SEQ ID NO:1 to 15, preferably, the identity is 85% or more, more preferably the identity is 90% or more, even more preferably, the identity is 95% or more, 96% or more, 97% or more, 98% or more or 99% or more, in the most preferred embodiment, the identity is 100% to any of the sequences as defined by SEQ ID NO:1 to 15 or
iii) a fragment of 100 or more consecutive bases, preferably 150 or more consecutive bases, more preferably 200 consecutive bases or more even more preferably 250 or more consecutive bases of a nucleic acid molecule of i) or ii) which has an expressing enhancing activity, for example 65% or more, preferably 70% or more, more preferably 75% or more, even more preferably 80% or more, 85% or more or 90% or more, in a most preferred embodiment it has 95% or more of the expression enhancing activity as the corresponding nucleic acid molecule having the sequence of any of the sequences as defined by SEQ ID NO:1 to 15, or iv) a nucleic acid molecule which is the complement or reverse complement of any of the previously mentioned nucleic acid molecules under i) to iii), or v) a nucleic acid molecule which is obtainable by PCR using oligonucleotide primers described by SEQ ID NO: 20 to 29, 34 to 41, 44 to 51 and 54 to 57 as shown in Table 2 or vi) a nucleic acid molecule of 100 nucleotides or more, 150 nucleotides or more, 200 nucleotides or more or 250 nucleotides or more, hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO:1 to 15 or the complement thereof. Preferably, said nucleic acid molecule is hybridizing under conditions equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO:1 to 15 or the complement thereof, more preferably, said nucleic acid molecule is hybridizing under conditions equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by any of the sequences as defined by SEQ ID NO:1 to 15 or the complement thereof.

In one embodiment, the one or more NEENA is heterologous to the promoter to which it is functionally linked.

As described above under v) the nucleic acid molecule obtainable by PCR using oligonucleotides as defined by SEQ IDs 20 to 29, 34 to 41, 44 to 51 and 54 to 57 as shown in Table 2 is obtainable for example from genomic DNA from *Arabidopsis* plants such as *A. thaliana* using the conditions as described in Example 1 below.

The skilled person is aware of variations in the temperature profile, cycle number and/or buffer composition or concentration to obtain the respective NEENA molecule. The specific combination of oligonucleotides to be used in the respective PCR reaction for obtaining a respective NEENA molecule is described in Table 2.

A person skilled in the art is aware of methods for rendering a unidirectional to a bidirectional promoter and of methods to use the complement or reverse complement of a promoter sequence for creating a promoter having the same promoter specificity as the original sequence. Such methods are for example described for constitutive as well as inducible promoters by Xie et al. (2001) "Bidirectionalization of polar promoters in plants" nature biotechnology 19 pages 677-679.

The authors describe that it is sufficient to add a minimal promoter to the 5' prime end of any given promoter to receive a promoter controlling expression in both directions with same promoter specificity. Hence a high expression promoter functionally linked to a NEENA as described above is functional in complement or reverse complement and therefore the NEENA is functional in complement or reverse complement too.

In principal the NEENA may be functionally linked to any promoter such as tissue specific, inducible, developmental specific or constitutive promoters. The respective NEENA will lead to an enhanced seed-specific and/or seed-preferential expression of the heterologous nucleic acid under the control of the respective promoter to which the one or more NEENA is functionally linked to. The enhancement of expression of promoters other than seed-specific and/or seed-preferential promoters, for example constitutive promoters or promoters with differing tissue specificity, will render the specificity of these promoters. Expression of the nucleic acid under control of the respective promoter will be significantly increased in seeds, where the transcript of said nucleic acid may have not or only weakly been detected without the NEENA functionally linked to its promoter. Hence, tissue- or developmental specific or any other promoter may be rendered to seed-specific and/or seed-preferential promoters by functionally linking one or more of the NEENA molecules as described above to said promoter. It is therefore another embodiment of the invention to provide a method for rendering the specificity of any given promoter functional in plant to a seed-specific and/or seed preferential promoter by linking the respective promoter to a NEENA molecule comprising a sequence as described above under i) to vi). Preferably, the one or more NEENA is functionally linked to any seed-specific and/or seed-preferential promoter and will enhance expression of the nucleic acid molecule under control of said promoter. Seed-specific and/or seed-preferential promoters to be used in any method of the invention may be derived from plants, for example monocotyledonous or dicotyledonous plants, from bacteria and/or viruses or may be synthetic promoters. Seed specific and/or seed-preferential promoters to be used are for example the SBP-promoter from *Vicia faba*, the Unknown Seed Protein-promoter (USP) from *Vicia faba*, the napin promoter from *Brassica napus*, the conlinin-promoter from *Linum usitatissmum*, the promoter from the *A. thaliana* gene At5g01670 encoding the peroxiredoxin like protein, the promoter of the peroxiredoxin like protein from *Linum usitatissmum*, the globulin like protein promoter from *Brassica napus*, the arcelin5-1 promoter from *Phaseolus vulgaris*, the Zein promoter from Zea maize, the globulin promoter from Zea maize, the pKG86 promoter from Zea maize as described in Example 6 below and the like.

The high expression seed-specific and/or seed-preferential promoters of the invention functionally linked to a NEENA may be employed in any plant comprising for example moss, fern, gymnosperm or angiosperm, for example monocotyledonous or dicotyledonous plant. In a preferred embodiment said promoter of the invention functionally linked to a NEENA may be employed in monocotyledonous or dicotyledonous plants, preferably crop plant such as corn, soy, canola, cotton, potato, sugar beet, rice, wheat, *sorghum*, barley, *musa*, sugarcane, *miscanthus* and the like. In a preferred embodiment of the invention, said promoter which is functionally linked to a NEENA may be employed in monocotyledonous crop plants such as corn, rice, wheat, *sorghum*, barley, *musa, miscanthus* or sugarcane. In an especially preferred embodiment the promoter functionally linked to a NEENA may be employed in dicotyledonous crop plants such as soy, canola, cotton or potato.

A high expressing seed-specific and/or seed-preferential promoter as used in the application means for example a promoter which is functionally linked to a NEENA causing enhanced seed-specific and/or seed-preferential expression of the promoter in a plant seed or part thereof wherein the accumulation of RNA or rate of synthesis of RNA in seeds derived from the nucleic acid molecule under the control of the respective promoter functionally linked to a NEENA is higher, preferably significantly higher than the expression in seeds caused by the same promoter lacking a NEENA of the invention. Preferably the amount of RNA of the respective nucleic acid and/or the rate of RNA synthesis and/or the RNA stability in a plant is increased 50% or more, for example 100% or more, preferably 200% or more, more preferably 5 fold or more, even more preferably 10 fold or more, most preferably 20 fold or more for example 50 fold compared to a control plant of same age grown under the same conditions comprising the same seed-specific and/or seed-preferential promoter the latter not being functionally linked to a NEENA of the invention.

When used herein, significantly higher refers to statistical significance the skilled person is aware how to determine, for example by applying statistical tests such as the t-test to the respective data sets.

Methods for detecting expression conferred by a promoter are known in the art. For example, the promoter may be functionally linked to a marker gene such as GUS, GFP or luciferase and the activity of the respective protein encoded by the respective marker gene may be determined in the plant or part thereof. As a representative example, the method for detecting luciferase is described in detail below. Other methods are for example measuring the steady state level or synthesis rate of RNA of the nucleic acid molecule controlled by the promoter by methods known in the art, for example Northern blot analysis, qPCR, run-on assays or other methods described in the art.

A skilled person is aware of various methods for functionally linking two or more nucleic acid molecules. Such methods may encompass restriction/ligation, ligase independent cloning, recombineering, recombination or synthesis. Other methods may be employed to functionally link two or more nucleic acid molecules.

A further embodiment of the present invention is a method for producing a plant or part thereof with, compared to a respective control plant or part thereof, enhanced seed-specific and/or seed-preferential expression of one or more nucleic acid molecule comprising the steps of introducing into the plant or part thereof one or more NEENA comprising a nucleic acid molecule as defined above under i) to vi) and functionally linking said one or more NEENA to a promoter, preferably a seed-specific and/or seed-preferential promoter and to a nucleic acid molecule being under the control of said promoter, preferably seed-specific and/or seed-preferential promoter, wherein the NEENA is heterologous to said nucleic acid molecule.

The NEENA may be heterologous to the nucleic acid molecule which is under the control of said promoter to which the NEENA is functionally linked or it may be heterologous to both the promoter and the nucleic acid molecule under the control of said promoter.

The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. For example, a NEENA of the invention is in its natural environment functionally linked to its native promoter, whereas in the present invention it is linked to another promoter which might be derived from the same organism, a different organism or might be a synthetic promoter. It may also mean that the NEENA of the present invention is linked to its native promoter but the nucleic acid molecule under control of said promoter is heterologous to the promoter comprising its native NEENA. It is in addition to be understood that the promoter and/or the nucleic acid molecule under the control of said promoter functionally linked to a NEENA of the invention are heterologous to said NEENA as their sequence has been manipulated by for example mutation such as insertions, deletions and the forth so that the natural sequence of the promoter and/or the nucleic acid molecule under control of said promoter is modified and therefore have become heterologous to a NEENA of the invention. It may also be understood that the NEENA is heterologous to the nucleic acid to which it is functionally linked when the NEENA is functionally linked to its native promoter wherein the position of the NEENA in relation to said promoter is changed so that the promoter shows higher expression after such manipulation.

A plant exhibiting enhanced seed-specific and/or seed-preferential expression of a nucleic acid molecule as meant herein means a plant having a higher, preferably statistically significant higher seed-specific and/or seed-preferential expression of a nucleic acid molecule compared to a control plant grown under the same conditions without the respective NEENA functionally linked to the respective nucleic acid molecule. Such control plant may be a wild-type plant or a transgenic plant comprising the same promoter controlling the same gene as in the plant of the invention wherein the promoter is not linked to a NEENA of the invention.

Producing a plant as used herein comprises methods for stable transformation such as introducing a recombinant DNA construct into a plant or part thereof by means of *Agrobacterium* mediated transformation, protoplast transformation, particle bombardment or the like and optionally subsequent regeneration of a transgenic plant. It also comprises methods for transient transformation of a plant or part thereof such as viral infection or *Agrobacterium* infiltration. A skilled person is aware of further methods for stable and/or transient transformation of a plant or part thereof. Approaches such as breeding methods or protoplast fusion might also be employed for production of a plant of the invention and are covered herewith.

The method of the invention may be applied to any plant, for example gymnosperm or angiosperm, preferably angiosperm, for example dicotyledonous or monocotyledonous plants, preferably dicotyledonous plants. Preferred monocotyledonous plants are for example corn, wheat, rice, barley, *sorghum, musa*, sugarcane, *miscanthus* and *brachypodium*, especially preferred monocotyledonous plants are corn, wheat and rice. Preferred dicotyledonous plants are for example soy, rape seed, canola, linseed, cotton, potato, sugar beet, *tagetes* and *Arabidopsis*, especially preferred dicotyledonous plants are soy, rape seed, canola and potato In one embodiment of the invention, the methods as defined above are comprising the steps of
a) introducing the one or more NEENA comprising a nucleic acid molecule as defined above in i) to vi) into a plant or part thereof and
b) integrating said one or more NEENA into the genome of said plant or part thereof whereby said one or more NEENA is functionally linked to an endogenous preferably seed-specific and/or seed-preferential expressed nucleic acid heterologous to said one or more NEENA and optionally c) regenerating a plant or part thereof comprising said one or more NEENA from said transformed cell.

The one or more NEENA molecule may be introduced into the plant or part thereof by means of particle bombardment, protoplast electroporation, virus infection, *Agrobacterium* mediated transformation or any other approach known in the art. The NEENA molecule may be introduced integrated for example into a plasmid or viral DNA or viral RNA. The NEENA molecule may also be comprised on a BAC, YAC or artificial chromosome prior to introduction into the plant or part of the plant. It may be also introduced as a linear nucleic acid molecule comprising the NEENA sequence wherein additional sequences may be present adjacent to the NEENA sequence on the nucleic acid molecule. These sequences neighboring the NEENA sequence may be from about 20 bp, for example 20 bp to several hundred base pairs, for example 100 bp or more and may facilitate integration into the genome for example by homologous recombination. Any other method for genome integration may be employed, be it targeted integration approaches, such as homologous recombination or random integration approaches, such as illegitimate recombination.

The endogenous preferably seed-specific and/or seed-preferential expressed nucleic acid to which the NEENA molecule may be functionally linked may be any nucleic acid, preferably any seed-specific and/or seed-preferential expressed nucleic acid molecule. The nucleic acid molecule may be a protein coding nucleic acid molecule or a non coding molecule such as anti-sense RNA, rRNA, tRNA, miRNA, ta-siRNA, siRNA, dsRNA, snRNA, snoRNA or any other non-coding RNA known in the art.

The skilled person is aware of methods for identifying seed-specific and/or seed-preferential expressed nucleic acid molecules to which the method of the invention may preferably be applied for example by microarray chip hybridization, qPCR, Northern blot analysis, next generation sequencing etc.

A further way to perform the methods of the invention may be to a) provide an expression construct comprising one or more NEENA comprising a nucleic acid molecule as defined above in i) to vi) functionally linked to a promoter, preferably a seed-specific and/or seed-preferential promoter as defined above and to one or more nucleic acid molecule the latter being heterologous to said one or more NEENA and which is under the control of said promoter, preferably seed-specific and/or seed-preferential promoter and b) integrate said expression construct comprising said one or more NEENA into the genome of said plant or part thereof and optionally c) regenerate a plant or part thereof comprising said one or more expression construct from said transformed plant or part thereof.

The NEENA may be heterologous to the nucleic acid molecule which is under the control of said promoter to which the NEENA is functionally linked or it may be heterologous to both the promoter and the nucleic acid molecule under the control of said promoter.

The expression construct may be integrated into the genome of the respective plant with any method known in the art. The integration may be random using methods such as particle bombardment or *Agrobacterium* mediated transformation. In a preferred embodiment, the integration is via targeted integration for example by homologous recombination. The latter method would allow integrating the expression construct comprising a high expression promoter functionally linked to a NEENA into a favorable genome region. Favorable genome regions are for example genome regions known to comprise genes that are highly expressed for example in seeds and hence may increase expression derived from said expression construct compared to a genome region which shows no transcriptional activity.

In another preferred embodiment said one or more NEENA is functionally linked to a promoter, preferably a seed-specific and/or seed-preferential promoter close to the transcription start site of said heterologous nucleic acid molecule.

Close to the transcription start site as meant herein comprises functionally linking the one or more NEENA to a promoter, preferably a seed-specific and/or seed-preferential promoter 2500 bp or less, preferentially 2000 bp or less, more preferred 1500 bp or less, even more preferred 1000 bp or less and most preferred 500 bp or less away from the transcription start site of said heterologous nucleic acid molecule. It is to be understood that the NEENA may be integrated upstream or downstream in the respective distance from the transcription start site of the respective promoter. Hence, the one or more NEENA must not necessarily be included in the transcript of the respective heterologous nucleic acid under control of the preferably seed-specific and/or seed-preferential promoter the one or more NEENA is functionally linked to. Preferentially the one or more NEENA is integrated downstream of the transcription start site of the respective promoter, preferably seed-specific and/or seed-preferential promoter. The integration site downstream of the transcription start site may be in the 5' UTR, the 3' UTR, an exon or intron or it may replace an intron or partially or completely the 5' UTR or 3' UTR of the heterologous nucleic acid under the control of the preferably seed-specific and/or seed-preferential promoter. Preferentially the one or more NEENA is integrated in the 5' UTR or an intron or the NEENA is replacing an intron or a part or the complete 5'UTR, most preferentially it is integrated in the 5'UTR of the respective heterologous nucleic acid.

A further embodiment of the invention comprises a recombinant expression construct comprising one or more NEENA comprising a nucleic acid molecule as defined above in i) to vi).

The recombinant expression construct may further comprise one or more promoter, preferably seed-specific and/or seed-preferential promoter to which the one or more NEENA is functionally linked and optionally one or more expressed nucleic acid molecule the latter being heterologous to said one or more NEENA.

The NEENA may be heterologous to the nucleic acid molecule which is under the control of said promoter to which the NEENA is functionally linked or it may be heterologous to both the promoter and the nucleic acid molecule under the control of said promoter.

The expression construct may comprise one or more, for example two or more, for example 5 or more, such as 10 or more combinations of promoters, preferably seed-specific and/or seed-preferential promoters functionally linked to a NEENA and a nucleic acid molecule to be expressed which is heterologous to the respective NEENA. The expression construct may also comprise further promoters not comprising a NEENA functionally linked to nucleic acid molecules to be expressed homologous or heterologous to the respective promoter.

A recombinant expression vector comprising one or more recombinant expression construct as defined above is another embodiment of the invention. A multitude of expression vectors that may be used in the present invention are known to a skilled person. Methods for introducing such a vector comprising such an expression construct comprising for example a promoter functionally linked to a NEENA and optionally other elements such as a terminator into the genome of a plant and for recovering transgenic plants from a transformed cell are also well known in the art. Depending on the method used for the transformation of a plant or part thereof the entire vector might be integrated into the genome of said plant or part thereof or certain components of the vector might be integrated into the genome, such as, for example a T-DNA.

A transgenic plant or part thereof comprising one or more heterologous NEENA as defined above in i) to vi) is also enclosed in this invention. A NEENA is to be understood as being heterologous to the plant if it is synthetic, derived from another organism or the same organism but its natural genomic localization is rendered compared to a control plant, for example a wild type plant. It is to be understood, that a rendered genomic localization means the NEENA is located on another chromosome or on the same chromosome but 10 kb or more, for example 10 kb, preferably 5 kb or more, for example 5 kb, more preferably 1000 bp or more, for example 1000 bp, even more preferably 500 bp or more, for example 500 bp, especially preferably 100 bp or more, for example 100 bp, most preferably 10 bp or more, for example 10 bp dislocated from its natural genomic localization, for example in a wild type plant.

A transgenic cell or transgenic plant or part thereof comprising a recombinant expression vector as defined above or a recombinant expression construct as defined above is a further embodiment of the invention. The transgenic cell, transgenic plant or part thereof may be selected from the group consisting of bacteria, fungi, yeasts, or plant, insect or mammalian cells or plants. Preferred transgenic cells are bacteria, fungi, yeasts, plant cells. Preferred bacteria are Enterobacteria such as *E. coli* and bacteria of the genus *Agrobacteria*, for example *Agrobacterium tumefaciens* and *Agrobacterium rhizogenes*. Preferred plants are monocotyledonous or dicotyledonous plants for example monocotyledonous or dicotyledonous crop plants such as corn, soy, canola, cotton, potato, sugar beet, rice, wheat, *sorghum*, barley, *musa*, sugarcane, *miscanthus* and the like. Preferred crop plants are corn, rice, wheat, soy, canola, cotton or potato. Especially preferred dicotyledonous crop plants are soy, canola, cotton or potato. Especially preferred monocotyledonous crop plants are corn, wheat and rice.

A transgenic cell culture, transgenic seed, parts or propagation material derived from a transgenic cell or plant or part thereof as defined above comprising said heterologous NEENA as defined above in i) to vi) or said recombinant expression construct or said recombinant vector as defined above are other embodiments of the invention.

Transgenic parts or propagation material as meant herein comprise all tissues and organs, for example leaf, stem and fruit as well as material that is useful for propagation and/or regeneration of plants such as cuttings, scions, layers, branches or shoots comprising the respective NEENA, recombinant expression construct or recombinant vector.

A further embodiment of the invention is the use of the NEENA as defined above in i) to vi) or the recombinant construct or recombinant vector as defined above for enhancing expression in plants or parts thereof.

Hence the application at hand provides seed-specific and/or seed-preferential gene expression enhancing nucleic acid molecules comprising one or more promoter, preferably seed-specific and/or seed preferential promoter functionally linked to one or more NEENA. Additionally use of such gene expression enhancing nucleic acid molecules and expression constructs, expression vectors, transgenic plants or parts thereof and transgenic cells comprising such gene expression enhancing nucleic acid molecules are provided.

A use of a transgenic cell culture, transgenic seed, parts or propagation material derived from a transgenic cell or plant or part thereof as defined above for the production of foodstuffs, animal feeds, seeds, pharmaceuticals or fine chemicals is also enclosed in this invention.

DEFINITIONS

Abbreviations: NEENA—nucleic acid expression enhancing nucleic acid, GFP—green fluorescence protein, GUS—beta-Glucuronidase, BAP—6-benzylaminopurine; 2,4-D—2,4-dichlorophenoxyacetic acid; MS—Murashige and Skoog medium; NAA—1-naphtaleneacetic acid; MES, 2-(N-morpholino-ethanesulfonic acid, IAA indole acetic acid; Kan: Kanamycin sulfate; GA3—Gibberellic acid; Timentin™: ticarcillin disodium/clavulanate potassium, microl: Microliter.

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Watson-Crick base pairing) or that is complementary to a target DNA molecule such as, for example genomic DNA present in the host cell.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed plant cell.

Enhanced expression: "enhance" or "increase" the expression of a nucleic acid molecule in a plant cell are used equivalently herein and mean that the level of expression of the nucleic acid molecule in a plant, part of a plant or plant cell after applying a method of the present invention is higher than its expression in the plant, part of the plant or plant cell before applying the method, or compared to a reference plant lacking a recombinant nucleic acid molecule of the invention. For example, the reference plant is comprising the same construct which is only lacking the respective NEENA. The term "enhanced" or "increased" as used herein are synonymous and means herein higher, preferably significantly higher expression of the nucleic acid molecule to be expressed. As used herein, an "enhancement" or "increase" of the level of an agent such as a protein, mRNA or RNA means that the level is increased relative to a substantially identical plant, part of a plant or plant cell grown under substantially identical conditions, lacking a recombinant nucleic acid molecule of the invention, for example lacking the NEENA molecule, the recombinant construct or recombinant vector of the invention. As used herein, "enhancement" or "increase" of the level of an agent, such as for example a preRNA, mRNA, rRNA, tRNA, snoRNA, snRNA expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a cell or organism lacking a recombinant nucleic acid molecule of the invention. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a plant or plant cell. Depending on the type of the induced protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193: 265-275) or measuring the absorption of CBB G-250 (Bradford M M (1976) Analyt Biochem 72:248-254). As one example for quantifying the activity of a protein, the detection of luciferase activity is described in the Examples below.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a seed-specific and/or seed-preferential promoter or of an inducible promoter, which initiates transcription only when the host cell is exposed to some particular external stimulus. In the case of a plant, the promoter can also be specific to a particular tissue or organ or stage of development.

Foreign: The term "foreign" refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or a NEENA) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

High expression seed-specific and/or seed-preferential promoter: A "high expression seed-specific and/or seed-preferential promoter" as used herein means a promoter causing seed-specific and/or seed-preferential expression in a plant or part thereof wherein the accumulation or rate of synthesis of RNA or stability of RNA derived from the nucleic acid molecule under the control of the respective promoter is higher, preferably significantly higher than the expression caused by the promoter lacking the NEENA of the invention. Preferably the amount of RNA and/or the rate of RNA synthesis and/or stability of RNA is increased 50% or more, for example 100% or more, preferably 200% or more, more preferably 5 fold or more, even more preferably 10 fold or more, most preferably 20 fold or more for example 50 fold relative to a seed-specific and/or seed-preferential promoter lacking a NEENA of the invention.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage homology between the two sequences is a function of the number of identical positions shared by the sequences (i.e. % homology=number of identical positions/total number of positions×100). The terms "homology" and "identity" are thus to be considered as synonyms.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444 (1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; —F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in defines [T/F]; default=F; q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast[nx] only) [Integer]; default=1; -a Number of processors to use [Integer]; default=1; -O SeqAlign file [File Out] Optional; -J Believe the query define [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; —I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of The European Molecular Biology Open Software Suite (EMBOSS) (Trends in Genetics 16 (6), 276 (2000)). Therefore preferably the calculations to determine the percentages of sequence homology are done with the programs "Gap" or "Needle" over the whole range of the sequences. The following standard adjustments for the comparison of nucleic acid sequences were used for "Needle": matrix: EDNA-FULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the homology is calculated on the complete length of the query sequence, for example SEQ ID NO:1.

Intron: refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: the fourteenth intron of the RecA-like protein gene and the seventh intron of the G5 gene from *Arabidopsis thaliana* are AT-AC introns. Pre-mRNAs containing introns have three short sequences that are—beside other sequences—essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron is comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branch point. The branchpoint sequence is important in splicing and splice-site selection in plants. The branchpoint sequence is usually located 10-60 nucleotides upstream of the 3' splice site.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

NEENA: see "Nucleic acid expression enhancing nucleic acid".

Non-coding: The term "non-coding" refers to sequences of nucleic acid molecules that do not encode part or all of an expressed protein. Non-coding sequences include but are not limited to introns, enhancers, promoter regions, 3' untranslated regions, and 5' untranslated regions.

Nucleic acid expression enhancing nucleic acid (NEENA): The term "nucleic acid expression enhancing nucleic acid" refers to a sequence and/or a nucleic acid molecule of a specific sequence having the intrinsic property to enhance expression of a nucleic acid under the control of a promoter to which the NEENA is functionally linked. Unlike promoter sequences, the NEENA as such is not able to drive expression. In order to fulfill the function of enhancing expression of a nucleic acid molecule functionally linked to the NEENA, the NEENA itself has to be functionally linked to a promoter. In distinction to enhancer sequences known in the art, the NEENA is acting in cis but not in trans and has to be located close to the transcription start site of the nucleic acid to be expressed.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophpyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, *sorghum*, millet, rye, triticale, or oats; the family of the Umbelliferae, especially the genus *Daucus*, very especially the species *carota* (carrot) and *Apium*, very especially the species *Graveolens dulce* (celery) and many others; the family of the Solanaceae, especially the genus *Lycopersicon*, very especially the species *esculentum* (tomato) and the genus *Solanum*, very especially the species *tuberosum* (potato) and *melongena* (egg plant), and many others (such as tobacco); and the genus *Capsicum*, very especially the species *annuum* (peppers) and many others; the family of the Leguminosae, especially the genus *Glycine*, very especially the species max (soybean), alfalfa, pea, lucerne, beans or peanut and many others; and the family of the Cruciferae (Brassicacae), especially the genus *Brassica*, very especially the species *napus* (oil seed rape), *campestris* (beet), *oleracea* cv Tastie (cabbage), *oleracea* cv Snowball Y (cauliflower) and *oleracea* cv Emperor (broccoli); and of the genus *Arabidopsis*, very especially the species *thaliana* and many others; the family of the Compositae, especially the genus *Lactuca*, very especially the species *sativa* (lettuce) and many others; the family of the Asteraceae such as sunflower, *Tagetes*, lettuce or *Calendula* and many other; the family of the Cucurbitaceae such as melon, pumpkin/squash or zucchini, and linseed. Further preferred are cotton, sugar cane, hemp, flax, chillies, and the various tree, nut and wine species.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter: The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases grassius.org/grasspromdb.html, mendel.cs.rhul.ac.uk/mendel.php?topic=plantprom, ppdb.gene.nagoya-u.ac.jp/cgi-bin/index.cgi. Promoters listed there may be addressed with the methods of the invention and are herewith included by reference. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a transgene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules may also comprise molecules, which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

"Seed-specific promoter" in the context of this invention means a promoter which is regulating transcription of a nucleic acid molecule under control of the respective promoter in seeds wherein the transcription in any tissue or cell of the seeds contribute to more than 90%, preferably more than 95%, more preferably more than 99% of the entire quantity of the RNA transcribed from said nucleic acid sequence in the entire plant during any of its developmental stage. The term "seed-specific expression" and "seed-specific NEENA" are to be understood accordingly. Hence a "seed-specific NEENA" enhances the transcription of a seed-specific or seed-preferential promoter in a way, that the transcription in seeds derived from said promoter functionally linked to a respective NEENA contribute to more than 90%, preferably more than 95%, more preferably more than 99% of the entire quantity of the RNA transcribed from the respective promoter functionally linked to a NEENA in the entire plant during any of its developmental stage.

"Seed-preferential promoter" in the context of this invention means a promoter which is regulating transcription of a nucleic acid molecule under control of the respective promoter in seeds wherein the transcription in any tissue or cell of the seeds contribute to more than 50%, preferably more than 70%, more preferably more than 80% of the entire quantity of the RNA transcribed from said nucleic acid sequence in the entire plant during any of its developmental stage. The term "seed-preferential expression" and "seed-preferential NEENA" are to be understood accordingly. Hence a "seed-preferential NEENA" enhances the transcription of a seed-specific or seed-preferential promoter in a way, that the transcription in seeds derived from said promoter functionally linked to a respective NEENA contribute to more than 50%, preferably more than 70%, more preferably more than 80% of the entire quantity of the RNA transcribed from the respective promoter functionally linked to a NEENA in the entire plant during any of its developmental stage.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Significant increase or decrease: An increase or decrease, for example in enzymatic activity or in gene expression, that is larger than the margin of error inherent in the measurement technique, preferably an increase or decrease by about 2-fold or greater of the activity of the control enzyme or expression in the control cell, more preferably an increase or decrease by about 5-fold or greater, and most preferably an increase or decrease by about 10-fold or greater.

Small nucleic acid molecules: "small nucleic acid molecules" are understood as molecules consisting of nucleic acids or derivatives thereof such as RNA or DNA. They may be double-stranded or single-stranded and are between about 15 and about 30 bp, for example between 15 and 30 bp, more preferred between about 19 and about 26 bp, for example between 19 and 26 bp, even more preferred between about 20 and about 25 bp for example between 20 and 25 bp. In a especially preferred embodiment the oligonucleotides are between about 21 and about 24 bp, for example between 21 and 24 bp. In a most preferred embodiment, the small nucleic acid molecules are about 21 bp and about 24 bp, for example 21 bp and 24 bp.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J. Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol III. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

EXAMPLES

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells were performed as described (Sambrook et al., 1989). Sequence analyses of recombinant DNA were performed with a laser fluorescence DNA sequencer (Applied Biosystems, Foster City, Calif., USA) using the Sanger technology (Sanger et al., 1977). Unless described otherwise, chemicals and reagents were obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases were from New England Biolabs (Ipswich, Mass., USA) or Roche Diagnostics GmbH (Penzberg, Germany). Oligonucleotides were synthesized by Eurofins MWG Operon (Ebersberg, Germany).

Example 1

Identification of Nucleic Acid Expression Enhancing Nucleic Acids (NEENA) Candidates from Genes with Seed-Specific or Seed-Preferential Expression 1.1 Identification of NEENA Molecules from *A. Thaliana* Genes Using publicly available genomic DNA sequences (e.g. ncbi.nlm.nih.gov/genomes/PLANTS/PlantList.html) and transcript expression data (e.g. weigelworld.org/resources/microarray/AtGenExpress/), a set of 19 NEENA candidates deriving from *Arabidopsis thaliana* transcripts with seed-specific or seed-preferential expression was selected for detailed analyses. The candidates were named as follows:

TABLE 1 seed specific NEENA candidates (NEENAss).

| NEENA name | Locus | Annotation | SEQ ID NO |
|---|---|---|---|
| NEENAss1 | At1g62290 | aspartyl protease family protein | 1 |
| NEENAss2 | At1g65090 | expressed protein | 2 |
| NEENAss15 | At2g27040 | PAZ domain-containing protein | 3 |
| NEENAss18 | At1g01170 | ozone-responsive stress-related protein, putative | 4 |

TABLE 1-continued seed specific NEENA candidates (NEENAss).

| NEENA name | Locus | Annotation | SEQ ID NO |
|---|---|---|---|
| NEENAss14 | At5g63190 | MA3 domain-containing protein | 5 |
| NEENAss4 | At5g07830 | glycosyl hydrolase family 79 N-terminal domain-containing protein similar to beta-glucuronidase AtGUS2 | 6 |
| NEENAss13 | At2g04520 | eukaryotic translation initiation factor 1A, putative/eIF-1A | 7 |
| NEENAss3 | At5g60760 | 2-phosphoglycerate kinase-related | 8 |
| NEENAss5 | At1g11170 | expressed protein contains Pfam profile PF05212 | 9 |
| NEENAss11 | At4g37050 | PLA V/PLP4 (Patatin-like protein 4) | 10 |
| NEENAss8 | At1g56170 | HAP5B (Heme activator protein (yeast) homolog 5B) | 11 |
| NEENAss16 | At1g54100 | aldehyde dehydrogenase, putative/antiquitin | 12 |
| NEENAss9 | At3g12670 | CTP synthase, putative/UTP-ammonia ligase, putative | 13 |
| NEENAss20 | At4g04460 | aspartyl protease family protein | 14 |
| NEENAss10 | At1g04120 | ATMRP5 (Arabidopsis thaliana multidrug resistance-associated protein 5) | 15 |
| NEENAss6 | At2g41070 | basic leucine zipper transcription factor (BZIP12) | 16 |
| NEENAss12 | At1g05450 | protease inhibitor/seed storage/lipid transfer protein (LTP)-related | 17 |
| NEENAss7 | At4g03050 | 2-oxoglutarate-dependent dioxygenase, putative (AOP3) | 18 |
| NEENAss17 | At3g12490 | cysteine protease inhibitor, putative/cystatin | 19 |

1.2 Isolation of the NEENA Candidates

Genomic DNA was extracted from *A. thaliana* green tissue using the Qiagen DNeasy Plant Mini Kit (Qiagen, Hilden, Germany). Genomic DNA fragments containing putative NEENA molecules were isolated by conventional polymerase chain reaction (PCR). Primers were designed on the basis of the *A. thaliana* genome sequence with a multitude of NEENA candidates (Table 2) and followed the protocol outlined by Phusion High Fidelity DNA Polymerase (Cat No F-540L, New England Biolabs, Ipswich, Mass., USA). The isolated DNA was used as template DNA in a PCR amplification using the following primers:

TABLE 2

Primer sequences

| Primer name | Sequence | SEQ ID NO | PCR yielding SEQ ID NO |
|---|---|---|---|
| NEENAss1_for | aataatggtacctggtgcttaaacactctggtgagt | 20 | 1 |
| NEENAss1_rev | aataatccatggtttgacctacaaaatcaaagcagtca | 21 | |
| NEENAss2_for | tttttggtaccagttctttgctttcgaagttgc | 22 | 2 |
| NEENAss2_rev | tttttccatggtactacgtactgttttcaattct | 23 | |
| NEENAss3_for | aaaaaggtaccatttccacacgctttctatcatttc | 24 | 8 |
| NEENAss3_rev | aaaaaaccatggttatctctctctaaaaaataaaaacgaatc | 25 | |
| NEENAss4_for | aataaggtaccgtccagaatttctccattga | 26 | 6 |
| NEENAss4_rev | aataaaccatggtcttcactatccaaagctctca | 27 | |
| NEENAss5_for | tttttggtaccgtctactttcattacagtgactctg | 28 | 9 |
| NEENAss5_rev | tttttccatggttatattttacctgcaacacaattcaa | 29 | |
| NEENAss6_for | ttttatggtacccactcgaatactgcatgcaa | 30 | 16 |
| NEENAss6_rev | ttttatccatggttatgtagcctttacacagaaaacaa | 31 | |
| NEENAss7_for | tatataggtaccaacaactatggcctgagggt | 32 | 18 |
| NEENAss7_rev | tatataccatggttatcttactgttttaaccaaaaaataaaat | 33 | |

TABLE 2-continued

Primer sequences

| Primer name | Sequence | SEQ ID NO | PCR yielding SEQ ID NO |
|---|---|---|---|
| NEENAss8_for | tttttaggtaccatcttagggtttcgcgagatctca | 34 | 11 |
| NEENAss8_rev | tttttccatggtgctaagctatctctgttaatataaaattg | 35 | |
| NEENAss9_for | tttttggtaccattttttgttggtgaaaggtaga | 36 | 13 |
| NEENAss9_rev | tttttaccatggttacgtttttgtctctgcttcttct | 37 | |
| NEENAss10_for | tatattggtacctctgggaaatatcgattttgatct | 38 | 15 |
| NEENAss10_rev | tatataccatggtctcaccacatcccaaagctc | 39 | |
| NEENAss11_for | ttttatggtaccgcacaatcttagcttaccttgaa | 40 | 10 |
| NEENAss11_rev | ttttatccatggttatttaatccacaagccttgcctc | 41 | |
| NEENAss12_for | tttttaggtacctgtcggagaagtgggcg | 42 | 17 |
| NEENAsskor-rev | tttttaccatggagaagtgggcggacg | 43 | |
| NEENAss13_for | ttttatggtacctagcttaatctcagattcgaatcgt | 44 | 7 |
| NEENAss13_rev | ttttatccatggtagtatctacataccaatcatacaaatg | 45 | |
| NEENAss14_for | tttttggtaccttttcacgatttggaatttga | 46 | 5 |
| NEENAss14_rev | tttttccatggtctacaacattaaaacgaccatta | 47 | |
| NEENAss15_for | tatataggtaccagggtttcgttttgtttca | 48 | 3 |
| NEENAss15_rev | tatataccatggttatctcctgctcaaagaaacca | 49 | |
| NEENAss16_for | tttataggtaccagaagctcatttcttcgatac | 50 | 12 |
| NEENAss16_rev | tttataccatggtctctgcgcaaaaattcacc | 51 | |
| NEENAss17_for | tatattggtacctctaaaaatacagggcacc | 52 | 19 |
| NEENAss17_rev | tatattccatggttactcttcgttgcagaagccta | 53 | |
| NEENAss18_for | tatataggtaccactgtttaagcttcactgtct | 54 | 4 |
| NEENAss18_rev | tatataccatggtttcttctaaagctgaaagt | 55 | |
| NEENAss20_for | tatataggtaccttaagcttttaagaatctctactcaca | 56 | 14 |
| NEENAss20(2)_rev | atatatccatggttaaattttacctgtcatcaaaaacaaca | 57 | |

Amplification during the PCR was carried out with the following composition (50 micro)):

3.00 microl A. thaliana genomic DNA (50 ng/microl)
10.00 microl 5× Phusion HF Buffer
4.00 microl dNTP (2.5 mM)
2.50 microl for Primer (10 microM)
2.50 microl rev Primer (10 microM)
0.50 microl Phusion HF DNA Polymerase (2 U/microl)

A touch-down approach was employed for the PCR with the following parameters: 98.0° C. for 30 sec (1 cycle), 98.0° C. for 30 sec, 56.0° C. for 30 sec and 72.0° C. for 60 sec (4 cycles), 4 additional cycles each for 54.0° C., 51.0° C. and 49.0° C. annealing temperature, followed by 20 cycles with 98.0° C. for 30 sec, 46.0° C. for 30 sec and 72.0° C. for 60 sec (4 cycles) and 72.0° C. for 5 min. The amplification products were loaded on a 2% (w/v) agarose gel and separated at 80V. The PCR products were excised from the gel and purified with the Qiagen Gel Extraction Kit (Qiagen, Hilden, Germany). Following a DNA restriction digest with NcoI (10 U/microl) and KpnI (10 U/microl) restriction endonuclease, the digested products were again purified with the Qiagen Gel Extraction Kit (Qiagen, Hilden, Germany).

1.3 Vector Construction

Using the Multisite Gateway System (Invitrogen, Carlsbad, Calif., USA), the promoter::NEENA::reporter-gene cassettes were assembled into binary constructs for plant transformation. The A. thaliana p-AtPXR (At1g48130, GenBank AC023673.3; WO2006089950; with the prefix p-denoting promoter) seed specific promoter was used in the reporter gene construct, and firefly luciferase (Promega, Madison, Wis., USA) was utilized as reporter protein for quantitatively determining the expression enhancing effects of the NEENA molecules to be analyzed. The pENTR/A vector holding the p-AtPXR promoter was cloned via site specific recombination (BP-reaction) between the pDONR/A vector and p-AtPXR amplification products with primers p-AtPXR-for and p-AtPXR-rev (Table 3) on genomic DNA (see above) with site specific recombination sites at either end according to the manufacturers manual (Invitrogen, Carlsbad, Calif., USA). Positive pENTR/A clones underwent sequence analysis to ensure correctness of p-AtPXR promoter.

TABLE 3

Primer sequences (p-AtPXR)

| Primer name Sequence | SEQ ID NO. |
|---|---|
| p-AtPXR-for ggggacaactttgtatagaaaagttggccacatcatgtttagacttatc | 58 |
| p-AtPXR-rev ggggactgcttttttgtacaaacttgtttaccttttatatttatatatag | 59 |

An ENTR/B vector containing the firefly luciferase coding sequence (Promega, Madison, Wis., USA) followed by the t-nos nopalin synthase transcriptional terminator (Genbank V00087) was generated. NEENA candidate PCR fragments (see above) were cloned separately upstream of the firefly luciferase coding sequence using KpnI and NcoI restriction enzymes. The resulting pENTR/B vectors are summarized in table 4, with promoter molecules having the prefix p-, coding sequences having the prefix c-, and terminator molecules having the prefix t-.

TABLE 4 all pENTR/B vectors plus and minus NEENA candidates

| pENTR/B vector | Composition of the partial expression cassette SEQ ID NO::reporter gene::terminator |
|---|---|
| LJK01 | MCS::c-LUC::t-nos |
| LJK19 | SEQ ID NO1::c-LUC::t-nos |
| LJK20 | SEQ ID NO2::c-LUC::t-nos |
| LJK21 | SEQ ID NO8::c-LUC::t-nos |
| LJK22 | SEQ ID NO6::c-LUC::t-nos |
| LJK23 | SEQ ID NO9::c-LUC::t-nos |
| LJK24 | SEQ ID NO16::c-LUC::t-nos |
| LJK25 | SEQ ID NO18::c-LUC::t-nos |
| LJK26 | SEQ ID NO11::c-LUC::t-nos |
| LJK27 | SEQ ID NO13::c-LUC::t-nos |
| LJK28 | SEQ ID NO15::c-LUC::t-nos |
| LJK29 | SEQ ID NO10::c-LUC::t-nos |
| LJK30 | SEQ ID NO17::c-LUC::t-nos |
| LJK31 | SEQ ID NO7::c-LUC::t-nos |
| LJK32 | SEQ ID NO5::c-LUC::t-nos |
| LJK33 | SEQ ID NO3::c-LUC::t-nos |
| LJK34 | SEQ ID NO12::c-LUC::t-nos |
| LJK35 | SEQ ID NO19::c-LUC::t-nos |
| LJK36 | SEQ ID NO4::c-LUC::t-nos |
| LJK38 | SEQ ID NO14::c-LUC::t-nos |

The pENTR/C vector was constructed by introduction of a multiple cloning site (SEQ ID NO60) via KpnI and HindIII restriction sites. By performing a site specific recombination (LR-reaction), the created pENTR/A, pENTR/B and pENTR/C were combined with the pSUN destination vector (pSUN derivative) according to the manufacturers (Invitrogen, Carlsbad, Calif., USA) Multisite Gateway manual. The reactions yielded 1 binary vector with p-AtPXR promoter, the firefly luciferase coding sequence c-LUC and the t-nos terminator and 19 vectors harboring SEQ ID NO1, NO2, NO3, NO4, NO5, NO6, NO7, NO8, NO9, NO10, NO11, NO12, NO13, NO14, NO15, NO16, NO17, NO18 and NO19 immediately upstream of the firefly luciferase coding sequence (Table 5), for which the combination with SEQ ID NO1 is given exemplary (SEQ ID NO61). Except for varying SEQ ID NO2 to NO19, the nucleotide sequence is identical in all vectors (Table 5). The resulting plant transformation vectors are summarized in table 5:

TABLE 5

Plant expression vectors for A. thaliana transformation

| plant expression vector | Composition of the expression cassette Promoter::SEQ ID NO::reporter gene::terminator | SEQ ID NO |
|---|---|---|
| LJK134 | p-AtPXR::-::c-LUC::t-nos | |
| LJK71 | p-AtPXR::SEQ ID NO1::c-LUC::t-nos | 61 |
| LJK72 | p-AtPXR::SEQ ID NO2::c-LUC::t-nos | |
| LJK73 | p-AtPXR::SEQ ID NO8::c-LUC::t-nos | |
| LJK74 | p-AtPXR::SEQ ID NO6::c-LUC::t-nos | |
| LJK75 | p-AtPXR::SEQ ID NO9::c-LUC::t-nos | |
| LJK76 | p-AtPXR::SEQ ID NO16::c-LUC::t-nos | |
| LJK77 | p-AtPXR::SEQ ID NO18::c-LUC::t-nos | |
| LJK78 | p-AtPXR::SEQ ID NO11::c-LUC::t-nos | |
| LJK79 | p-AtPXR::SEQ ID NO13::c-LUC::t-nos | |
| LJK80 | p-AtPXR::SEQ ID NO15::c-LUC::t-nos | |
| LJK81 | p-AtPXR::SEQ ID NO10::c-LUC::t-nos | |
| LJK82 | p-AtPXR::SEQ ID NO17::c-LUC::t-nos | |
| LJK83 | p-AtPXR::SEQ ID NO7::c-LUC::t-nos | |
| LJK84 | p-AtPXR::SEQ ID NO5::c-LUC::t-nos | |
| LJK85 | p-AtPXR::SEQ ID NO3::c-LUC::t-nos | |
| LJK86 | p-AtPXR::SEQ ID NO12::c-LUC::t-nos | |
| LJK87 | p-AtPXR::SEQ ID NO19::c-LUC::t-nos | |
| LJK88 | p-AtPXR::SEQ ID NO4::c-LUC::t-nos | |
| LJK90 | p-AtPXR::SEQ ID NO14::c-LUC::t-nos | |

The resulting vectors were subsequently used to generate transgenic *A. thaliana* plants.

Example 2

Screening for NEENA Molecules Enhancing Gene Expression in Transgenic *A. thaliana* Plants This example illustrates that only selected NEENA candidate molecules are capable of enhancing gene expression.

All binary constructs containing the selected NEENA candidate molecules described in example 1 were stably transformed into *Arabidopsis thaliana* plants along with a NEENA-less control construct. In order to generate transgenic *A. thaliana* plants, *Agrobacterium tumefaciens* (strain C58C1 pGV2260) was transformed with the various vector constructs described above. For *A. thaliana* transformation, the Floral Dip method was employed (Clough and Bent, 1998, Plant Journal 16: 735-743). T1 transgenic plants were selected by germinating and growing seedlings on Kanamycin. After 12 days, cotyledons of transformants and wild-type control plants were sampled and distributed in 96 well plates preloaded with 50 microl 0.5× Murashige-Skoog Medium and subjected to Luciferase reporter gene assays (amended protocol after Weigel and Glazebrook, 2002, *Arabidopsis*, a laboratory manual, Cold Spring Harbor Laboratory Press, Chapter 7, ISBN 0-87969-572-2). Luminescence of cotyledons was determined in a solution containing 0.1 mM D-Luciferin (Cat No: L-8220, BioSynth, Staad, Switzerland) and 0.01% Tween20 (Sigma Aldrich, St. Louis, USA) in a MicroLumat Plus LB96V (Berthold Technologies, Bad Wildbad, Germany) recorded at 60 min after D-Luciferin addition. Instrument readings were averaged for each construct and based on these average expression values, fold change values were calculated to assess the impact of presence of a putative NEENA over reporter gene constructs lacking the respective putative NEENA. In comparison to seed specific p-AtPXR promoter-only NEENA-less reporter gene constructs, the 19 tested NEENA candidates containing constructs showed negative as well as positive effects, ranging from 0.8-fold to 22.2-fold induction in Luciferase activity (FIG. 1). In total, 15 putative NEENA molecules comprising sequences with SEQ ID NO1, NO2, NO3, NO4, NO5, NO6, NO7, NO8, NO9, NO10, NO11, NO12, NO13, NO14 and NO15 conferred a greater than 2.5-fold increase in gene expression based on luciferase reporter gene activity compared to the NEENA-less promoter-only reporter gene construct (FIG. 1) and hence are functional NEENA molecules. Since a number of the tested NEENA candidate molecules have marginal or even negative effects on the enhancement of gene expression, not all putative NEENA molecules are mediating a common stimulatory effect, but rather that the selected NEENA sequences convey significant enhancement of gene expression (SEQ ID NO 1 to 15).

Example 3

Test of NEENA Molecules for Seed Specific Enhancement of Gene Expression in Oilseed Rape Plants This example illustrates that NEENA molecules can be used across species to enhance gene expression of a tissue specific promoter compared to a NEENA-less promoter-only approach. NEENA molecules mediating the strongest enhancement in gene expression in the pre-screening (cp. Example 2, SEQ ID NO1, NO2, NO3, NO4, NO5, NO6 and NO7) were selected for determining the enhancement on gene expression levels in transgenic oilseed rape plants.

3.1 Vector Construction for *B. napus* Plant Transformation

For transformation of oilseed rape plants, reporter gene expression cassettes without and with gene expression control molecules (SEQ IDs NO1-NO7) were combined with a gene expression cassette carrying a selectable marker gene for detecting transgenic plant lines within a pENTR/C vector. By performing a site specific recombination (LR-reaction), as previously described (see above, 1.3), the pENTR/A, pENTR/B and the pENTR/C carrying the selectable marker cassette were combined with the pSUN destination vector according to the manufacturers (Invitrogen, Carlsbad, Calif., USA) Multisite Gateway manual. The reactions yielded one binary vector with p-AtPXR promoter, the firefly luciferase coding sequence c-LUC, the t-nos terminator and the selectable marker cassette as well as 7 vectors harboring SEQ ID NO1, NO2, NO3, NO4, NO5, NO6 and NO7 immediately upstream of the firefly luciferase coding sequence (Table 6), for which the combination with SEQ ID NO1 is given exemplary (SEQ ID NO62). Except for varying SEQ ID NO2 to NO7, the nucleotide sequence is identical in all vectors (Table 6). The resulting plant transformation vectors are summarized in table 6:

TABLE 6

Plant expression vectors for B. napus transformation

| plant expression vector | Composition of the expression cassette Promoter::SEQ ID NO::reporter gene::terminator | SEQ ID NO |
|---|---|---|
| LJK148 | p-AtPXR::-::c-LUC::t-nos | |
| LJK156 | p-AtPXR::SEQ ID NO1::c-LUC::t-nos | 62 |
| LJK157 | p-AtPXR::SEQ ID NO2::c-LUC::t-nos | |

TABLE 6-continued

Plant expression vectors for B. napus transformation

| plant expression vector | Composition of the expression cassette Promoter::SEQ ID NO::reporter gene::terminator | SEQ ID NO |
|---|---|---|
| LJK158 | p-AtPXR::SEQ ID NO7::c-LUC::t-nos | |
| LJK159 | p-AtPXR::SEQ ID NO5::c-LUC::t-nos | |
| LJK160 | p-AtPXR::SEQ ID NO4::c-LUC::t-nos | |
| LJK161 | p-AtPXR::SEQ ID NO6::c-LUC::t-nos | |
| LJK162 | p-AtPXR::SEQ ID NO3::c-LUC::t-nos | |

3.2 Generation of Transgenic Rapeseed Plants (Amended Protocol According to Moloney et al., 1992, Plant Cell Reports, 8: 238-242).

In preparation for the generation of transgenic rapeseed plants, the binary vectors were transformed into *Agrobacterium tumefaciens* C58C1:pGV2260 (Deblaere et al., 1985, Nucl. Acids. Res. 13: 4777-4788). A 1:50 dilution of an overnight culture of *Agrobacteria* harboring the respective binary construct was grown in Murashige-Skoog Medium (Murashige and Skoog, 1962, Physiol. Plant 15, 473) supplemented with 3% saccharose (3MS-Medium). For the transformation of rapeseed plants, petioles or hypocotyledons of sterile plants were incubated with a 1:50 *Agrobacterium* solution for 5-10 minutes followed by a three-day co-incubation in darkness at 25° C. on 3 MS. Medium supplemented with 0.8% bacto-agar. After three days, the explants were transferred to MS-medium containing 500 mg/l Claforan (Cefotaxime-Sodium), 100 nM Imazetapyr, 20 microM Benzylaminopurin (BAP) and 1.6 g/l Glucose in a 16 h light/8 h darkness light regime, which was repeated in weekly periods. Growing shoots were transferred to MS-Medium containing 2% saccharose, 250 mg/l Claforan and 0.8% Bacto-agar. After 3 weeks, the growth hormone 2-Indolbutyl acid was added to the medium to promote root formation. Shoots were transferred to soil following root development, grown for two weeks in a growth chamber and grown to maturity in greenhouse conditions.

3.3 Plant Analysis

Tissue samples were collected from the generated transgenic plants from leaves, flowers and seeds of varying developmental stages, stored in a freezer at −80° C. subjected to a Luciferase reporter gene assay (amended protocol after Ow et al., 1986). After grinding, the frozen tissue samples were resuspended in 800 microl of buffer I (0.1 M Phosphate buffer pH7.8, 1 mM DTT (Sigma Aldrich, St. Louis, Mo., USA), 0.05% Tween 20 (Sigma Aldrich, St. Louis, Mo., USA) followed by centrifugation at 10 000 g for 10 min. 75 microl of the aqueous supernatant were transferred to 96-well plates. After addition of 25 microl of buffer II (80 mM gycine-glycyl (Carl Roth, Karlsruhe, Germany), 40 mM MgSO4 (Duchefa, Haarlem, The Netherlands), 60 mM ATP (Sigma Aldrich, St. Louis, Mo., USA), pH 7.8) and D-Luciferin to a final concentration of 0.5 mM (Cat No: L-8220, BioSynth, Staad, Switzerland), luminescence was recorded in a MicroLumat Plus LB96V (Berthold Technologies, Bad Wildbad, Germany) yielding the unit relative light unit RLU per minute (RLU/min).

In order to normalize the luciferase activity between samples, the protein concentration was determined in the aqueous supernatant in parallel to the luciferase activity (adapted from Bradford, 1976, Anal. Biochem. 72, 248). 5 microl of the aqueous cell extract in buffer I were mixed with 250 microl of Bradford reagent (Sigma Aldrich, St. Louis, Mo., USA), incubated for 10 min at room temperature. Absorption was determined at 595 nm in a plate reader (Thermo Electron Corporation, Multiskan Ascent 354). The total protein amounts in the samples were calculated with a previously generated standard concentration curve. Values resulting from a ratio of RLU/min and mg protein/ml sample were averaged for transgenic plants harboring identical constructs and fold change values were calculated to assess the impact of NEENA molecule presence over NEENA-less reporter gene constructs.

3.4 NEENA Sequences Mediate Strong Enhancement of Gene Expression in Oilseed Rape Seeds For assessing the potential of enhancing gene expression of selected NEENA molecules (SEQ ID NO1, NO2, NO3, NO4, NO5, NO6, NO7) in oilseed rape seeds, seeds of identical developmental stages were collected from individual transgenic oilseed rape plant lines harboring either a promoter-only reporter gene construct or Luciferase reporter gene constructs containing a NEENA (SEQ ID NO1, NO2, NO3, NO4, NO5, NO6 or NO7). 10 seeds were collected from each transgenic event, processed and analyzed for Luciferase activity as described above (Example 3.3).

In comparison to seed specific p-AtPXR promoter-only NEENA-less reporter gene constructs, the 7 tested NEENA molecules all mediated strong enhancements in gene expression, ranging from 54-fold to 380-fold induction in Luciferase activity in canola seeds (FIG. 2a). Comparable enhancement of expression was detected in oilseed rape seeds in later maturation stages (data not shown).

3.5 NEENA Molecules Boost Gene Expression Tissue Specifically in Oilseed Rape Seeds To assess the tissue specific enhancement of gene expression mediated by the NEENA molecules (SEQ ID NO1, NO2, NO3, NO4, NO5, NO6 or NO7), Luciferase activity was determined in fully developed leaves and open flowers of the transgenic oilseed rape plants harboring the reporter gene constructs outlined above. Three leaf samples of identical size as well as a whole flower were collected from each plant separately and subjected to Luciferase reporter gene assays as described above (Example 3.3). 5 (Seq. ID NO1, NO2, NO3, NO4, NO5) of the 7 tested NEENA molecules showed Luciferase expression levels comparable to that of the NEENA-less p-AtPXR promoter construct in leaves and flowers and thus do not alter the tissue specificity of the seed-specific p-AtPXR promoter (FIGS. 2, b and c). 2 NEENA molecules (SEQ ID NO6, NO7) slightly enhanced Luciferase activity in leaves and flowers of the analyzed oilseed rape plants (FIGS. 2, b and c) compared to plants comprising the NEENA-less construct. Hence, these NEENAs SEQ ID NO 6 and 7 are seed preferential NEENAs whereas the other NEENAs SEQ ID NO 1 to 5 are seed-specific NEENAs.

Example 4

Analysis of NEENA for Seed Specific Enhancement of Strong Seed Specific Promoters This example illuminates that the expression enhancing capabilities of NEENA molecules can be used in combination with a variety of promoter molecules in order to enhance tissue specific expression levels compared to that of promoters alone.

4.1 Vector Construction for *B. napus* Plant Transformation

Selected NEENA molecules of the group tested in example 3 (SEQ IDs NO1, NO2, NO3, NO5 and NO6) were tested for their effect on enhancing tissue specific gene expression of strong seed specific promoters p-LuPXR (WO2006089950, Sequence 9) and p-VfUSP (X56240, Baeumlein et al., 1991). Vector construction was performed as described above (cp. Example 1.3 and 3.1), with the primer sequences outlined in table 7 and vector LJB765 (WO2009016202) as DNA template. Positive pENTR/A clones underwent sequence analysis to ensure correctness of p-LuPXR and p-VfUSP promoters.

TABLE 7

Primer sequences for p-LuPXR and p-VfUSP

| Primer name | Sequence | SEQ ID NO. |
|---|---|---|
| p-LuPXR-for | ggggacaactttgtatagaaaagttcacgggcaggacatagggactactac | 63 |
| p-LuPXR-rev | ggggactgctttttgtacaaacttggatttatgataaaaatgtcggtttc | 64 |
| p-VfUSP-for | ggggacaactttgtatagaaaagttctgcagcaaatttacacattgccac | 65 |
| p-VfUSP-rev | ggggactgctttttgtacaaacttgactggctatgaagaaattataatc | 66 |

By performing a site specific recombination (LR-reaction) as previously described (see above, 1.3), the pENTR/A, pENTR/B vectors and the pENTR/C vector carrying the selectable marker cassette were combined with the pSUN destination vector according to the manufacturers (Invitrogen, Carlsbad, Calif., USA) Multisite Gateway manual. The reactions yielded 1 binary vector with p-LuPXR promoter, the firefly luciferase coding sequence and the t-nos terminator as well as the selectable marker cassette and 4 vectors harboring SEQ ID NO1, NO2, NO3 and NO6 immediately upstream of the firefly luciferase coding sequence (Table 8), for which the combination with SEQ ID NO1 is given exemplary (SEQ ID NO67). Except for varying SEQ ID NO2, NO3 and NO6, the nucleotide sequence is identical in all vectors (Table 8). Similarly, the p-VfUSP promoter was used to generate the promoter-only construct LJK219 as well as constructs LJK220, LJK221, LJK224 and LJK225 containing SEQ IDs NO1, NO2, NO3 and NO5 (Table 8). The resulting plant transformation vectors are summarized in table 8:

TABLE 8

Plant expression vectors for B. napus transformation

| plant expression vector | Composition of the expression cassette Promoter::SEQ ID NO::reporter gene::terminator | SEQ ID NO |
|---|---|---|
| LJK212 | p-LuPXR::-::c-LUC::t-nos | |
| LJK213 | p-LuPXR::SEQ ID NO1::c-LUC::t-nos | 67 |
| LJK214 | p-LuPXR::SEQ ID NO2::c-LUC::t-nos | |
| LJK215 | p-LuPXR::SEQ ID NO6::c-LUC::t-nos | |
| LJK218 | p-LuPXR::SEQ ID NO3::c-LUC::t-nos | |
| LJK219 | p-VfUSP::-::c-LUC::t-nos | |
| LJK220 | p-VfUSP::SEQ ID NO1::c-LUC::t-nos | |

TABLE 8-continued

Plant expression vectors for B. napus transformation

| plant expression vector | Composition of the expression cassette Promoter::SEQ ID NO::reporter gene::terminator | SEQ ID NO |
|---|---|---|
| LJK221 | p-VfUSP::SEQ ID NO2::c-LUC::t-nos | |
| LJK224 | p-VfUSP::SEQ ID NO5::c-LUC::t-nos | |
| LJK225 | p-VfUSP::SEQ ID NO3::c-LUC::t-nos | |

4.2 NEENA Sequences Mediate Tissue Specific Enhancement of Gene Expression of Strong Seed Specific Promoters in Oilseed Rape Seeds Generation of transgenic rapeseed plants and plant analyses were conducted as described above (example 3.2 and 3.3).

In order to test the effect of selected NEENA molecules in combination with seed specific promoters (SEQ ID NO1, NO2, NO3, NO5 and NO6) in oilseed rape seeds, seeds of identical developmental stages were collected from individual transgenic oilseed rape plant lines harboring either a promoter-only reporter gene construct (LJK212 and LJK219) or Luciferase reporter gene constructs containing a NEENA (SEQ ID NO1, NO2, NO3, NO5 and NO6) (Table 9). From each transgenic event, 10 seeds were collected, processed and analyzed for Luciferase activity as described above (Example 3.3).

In comparison to seed specific p-LuPXR and p-VfUSP promoter-only NEENA-less reporter gene constructs, all tested NEENA molecules mediated strong enhancements in gene expression in oilseed rape seeds of medium maturity in combination with both, the p-LuPXR and p-VfUSP promoter (Table 9). Similar enhancement of expression was detected in oilseed rape seeds in later maturation stages.

TABLE 9

LUC expression in seeds of stably transformed oilseed rape plants.

| plant expression vector | Composition of the expression cassette Promoter::SEQ ID NO::reporter gene::terminator | | LUC expression in oilseed rape seeds* |
|---|---|---|---|
| LJK212 | p-LuPXR::-::c-LUC::t-nos | + | 20%** |
| LJK213 | p-LuPXR::SEQ ID NO1::c-LUC::t-nos | ++++ | 80% |
| LJK214 | p-LuPXR::SEQ ID NO2::c-LUC::t-nos | ++++ | 80% |
| LJK215 | p-LuPXR::SEQ ID NO6::c-LUC::t-nos | ++++ | 80% |
| LJK218 | p-LuPXR::SEQ ID NO3::c-LUC::t-nos | ++++ | 80% |
| LJK219 | p-VfUSP::-::c-LUC::t-nos | ++ | 40% |
| LJK220 | p-VfUSP::SEQ ID NO1::c-LUC::t-nos | +++++ | 100% |
| LJK221 | p-VfUSP::SEQ ID NO2::c-LUC::t-nos | +++++ | 100% |
| LJK224 | p-VfUSP::SEQ ID NO5::c-LUC::t-nos | ++++ | 80% |
| LJK225 | p-VfUSP::SEQ ID NO3::c-LUC::t-nos | +++++ | 100% |

*LUC expression given as a range of firefly luciferase activities (− no expression to +++++ very high expression), relative LUC expression compared to the expression of the linseed p-LuPXR promoter within the respective tissue.
**Relative luciferase expression compared to the expression controlled by the linseed peroxiredoxin promoter p-LuPXR.

To assess the tissue specific enhancement of gene expression mediated by the NEENA molecules (SEQ ID NO1, NO2, NO3, NO5 and NO6), Luciferase activity was determined in fully developed leaves of the transgenic oilseed rape plants harboring the reporter gene constructs outlined above. 3 leaf samples of identical size were collected from each plant separately and subjected to Luciferase reporter gene assays as described above (Example 3.2). The tissue specificities of the tested NEENA molecules (SEQ ID NO1, NO2, NO3, NO5, NO6) in combination with the p-LuPXR promoter and the p-VfUSP promoter resemble those tested with the p-AtPXR promoter analyzed above (example 3.5). As with the p-AtPXR promoter (example 3.5), the NEENA molecules (SEQ ID NO1, NO2, NO3 and NO5) showed no alteration of the tissue specificity of the p-LuPXR or p-VfUSP promoter (Table 10). Similar to the activity with the p-AtPXR promoter (example 3.5), the NEENA (SEQ ID NO6) conveyed enhancement of Luciferase activity in seeds, but also mediated Luciferase expression in the leaves of the analyzed oilseed rape plants (Table 10).

TABLE 10

LUC expression in leaves of stably transformed oilseed rape plants.

| plant expression vector | Composition of the expression cassette Promoter::SEQ ID NO::reporter gene::terminator | | LUC expression in oilseed rape leaves* |
|---|---|---|---|
| LJK212 | p-LuPXR::-::c-LUC::t-nos | − | 0%** |
| LJK213 | p-LuPXR::SEQ ID NO1::c-LUC::t-nos | − | 0% |
| LJK214 | p-LuPXR::SEQ ID NO2::c-LUC::t-nos | − | 0% |
| LJK215 | p-LuPXR::SEQ ID NO6::c-LUC::t-nos | + | 100% |
| LJK218 | p-LuPXR::SEQ ID NO3::c-LUC::t-nos | − | 0% |
| LJK219 | p-VfUSP::-::c-LUC::t-nos | − | 0% |
| LJK220 | p-VfUSP::SEQ ID NO1::c-LUC::t-nos | − | 0% |
| LJK221 | p-VfUSP::SEQ ID NO2::c-LUC::t-nos | − | 0% |
| LJK224 | p-VfUSP::SEQ ID NO5::c-LUC::t-nos | − | 0% |
| LJK225 | p-VfUSP::SEQ ID NO3::c-LUC::t-nos | − | 0% |

*LUC expression given as a range of firefly luciferase activities (− no expression to +++++ very high expression), relative LUC expression compared to the expression of the linseed p-LuPXR promoter within the respective tissue.
**Relative luciferase expression compared to the expression controlled by the linseed peroxiredoxin promoter p-LuPXR.

Example 5

Analysis of Tissue Specific Enhancement of Gene Expression in Soybean Plants

This example illustrates that the claimed NEENA molecules can be used in a wide array of plant species and across species borders from different plant families to enhance gene expression tissue specifically compared to a NEENA-less promoter-only approach.

NEENA sequence molecules mediating the strongest enhancement in gene expression in the pre-screening (cp. Example 2, SEQ ID NO1, NO2, NO4, NO5, NO6 and NO7) were selected for determining the enhancement on gene expression levels in transgenic soybean plants. Plant expression vectors LJK148, LJK156, LJK157, LJK158, LJK159, LJK160 and LJK161 (cp. example 3.1) were used for stable soybean transformation.

5.1 Generation of Transgenic Soybean Plants (Amended Protocol According to WO2005/121345; Olhoft et al., 2007).

Soybean seed germination, propagation, *A. rhizogenes* and axillary meristem explant preparation, and inoculations were done as previously described (WO2005/121345; Olhoft et al., 2007) with the exception that the constructs LJK148, LJK156, LJK157, LJK158, LJK159, LJK160 and LJK161 (cp. example 3.1) each contained a mutated AHAS gene driven by the parsley ubiquitin promoter PcUbi4-2, mediating tolerance to imidazolinone herbicides for selection.

Figure 3:
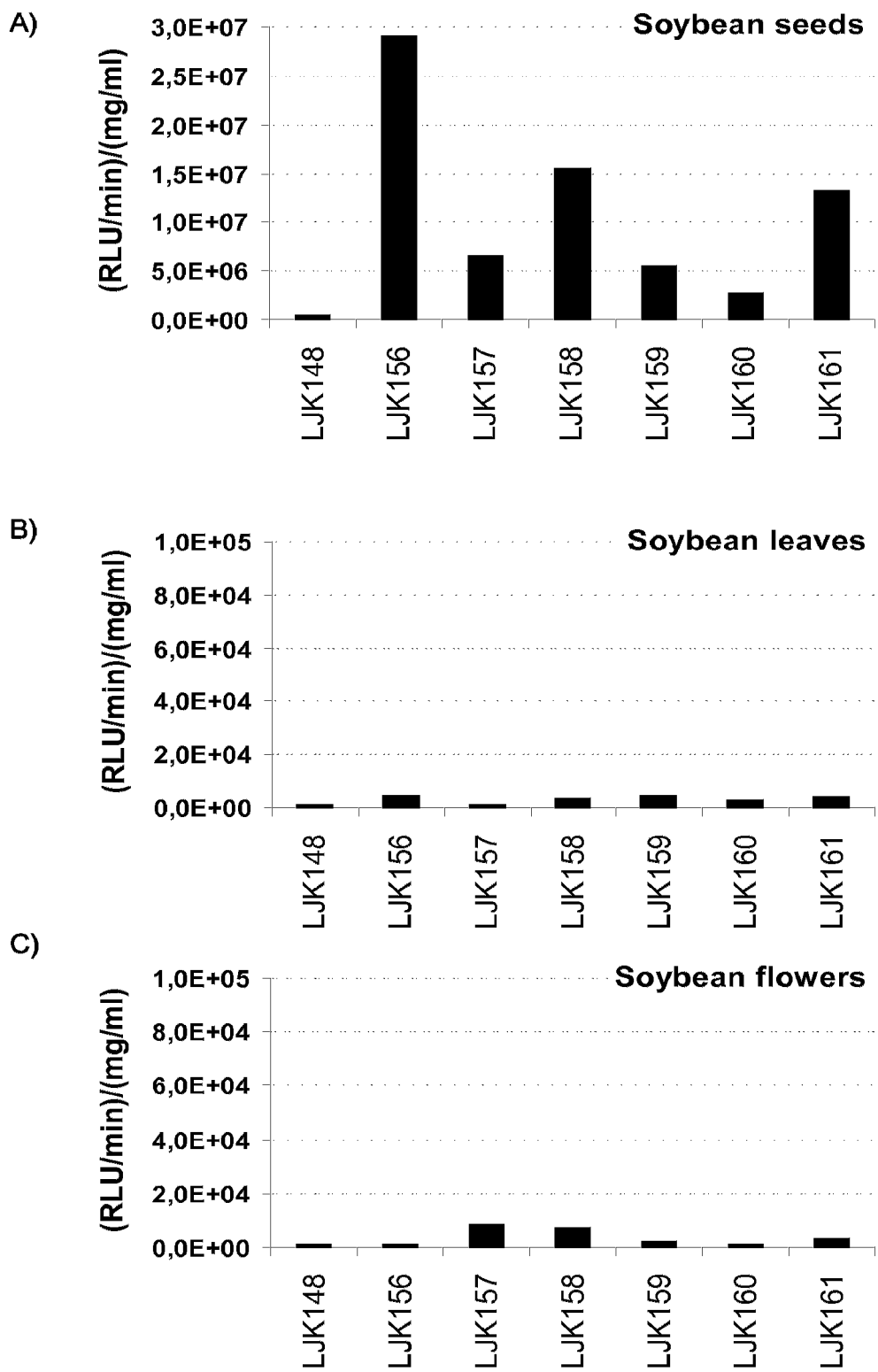

5.2 NEENA Sequences Mediate Strong Enhancement of Gene Expression in Soybean Plants Under Maintenance of Promoter Tissue Specificity Tissue samples were collected from the generated transgenic plants from leaves, flowers and seeds. The tissue samples were processed and analyzed as described above (cp. example 3.3) In comparison to the seed-specific p-AtPXR promoter-only NEENA-less reporter gene construct LJK148, the seven tested NEENA molecules all mediated strong enhancements in gene expression in soybean seeds based on Luciferase activity (FIG. 3a). In contrast, no significant alterations in Luciferase activity mediated by NEENA molecules (SEQ ID NO1, NO2, NO4, NO5, NO6 and NO7) could be detected in soybean leaves and flowers (FIGS. 3, b and c).

Example 6

Analysis of NEENA Activity in Monocotyledonous Plants

This example describes the analysis of NEENA sequences with SEQ ID NO 1, 2, 3, 4, 5, 6 and 7 in monocotyledonous plants.

6.1 Vector Construction

For analyzing NEENA sequences with SEQ ID NO 1, 2, 3, 4, 5, 6 and 7 in monocotyledonous plants, a pUC-based expression vector harboring an expression cassette composed of the NEENA-less, seed specific monocotyledonous promoter p-KG86 from *Z. mais* is combined with a coding sequence of the beta-Glucuronidase (GUS) gene followed by the nopaline synthase (NOS) transcriptional terminator is used. Genomic DNA is extracted from *A. thaliana* green tissue using the Qiagen DNeasy Plant Mini Kit (Qiagen, Hilden, Germany). Genomic DNA fragments containing NEENA molecules are isolated by conventional polymerase chain reaction (PCR). Primers are designed on the basis of the *A. thaliana* genome sequence with a multitude of NEENA candidates. The reaction comprises 7 sets of primers (Table 11) and follows the protocol outlined by Phusion High Fidelity DNA Polymerase (Cat No F-540L, New England Biolabs, Ipswich, Mass., USA) using the following primers:

Amplification during the PCR and purification of the amplification products is carried out as detailed above (example 1.2). Following a DNA restriction digest with AscI (10 U/microl) restriction endonuclease, the digested products are purified with the Qiagen Gel Extraction Kit (Qiagen, Hilden, Germany).

NEENA PCR fragments (see above) are cloned separately upstream of the beta-Glucuronidase coding sequence using AscI restriction sites. The reaction yields one binary vector with the p-KG86 promoter, the beta-Glucuronidase coding sequence c-GUS and the t-nos terminator and seven vectors harboring SEQ ID NO1, NO2, NO3, NO4, NO5, NO6 and NO7, immediately upstream of the beta-Glucuronidase coding sequence (Table 12), for which the combination with SEQ ID NO1 is given exemplary (SEQ ID NO82). Except for varying SEQ ID NO2 to NO7, the nucleotide sequence is identical in all vectors (Table 12). The resulting vectors are summarized in table 12, with promoter molecules having the prefix p-, coding sequences having the prefix c-, and terminator molecules having the prefix t-.

TABLE 12

Plant expression vectors

| plant expression vector | Composition of the expression cassette Promoter::SEQ ID NO::reporter gene::terminator | SEQ ID NO |
|---|---|---|
| RTP2933 | p-KG86::-::c-GUS::t-nos | |
| LJK351 | p-KG86::SEQ ID NO1::c-GUS::t-nos | 82 |
| LJK352 | p-KG86::SEQ ID NO2::c-GUS::t-nos | |
| LJK353 | p-KG86::SEQ ID NO3::c-GUS::t-nos | |
| LJK354 | p-KG86::SEQ ID NO4::c-GUS::t-nos | |

TABLE 11

Primer sequences

| Primer name | Sequence | SEQ ID NO | PCR yielding SEQ ID NO |
|---|---|---|---|
| NEENAss1_forII | aataatggcgcgcctggtgcttaaacactctggtgagt | 68 | 1 |
| NEENAss1_revII | aataatggcgcgcctttgacctacaaaatcaaagcagtca | 69 | |
| NEENAss2_forII | tttttggcgcgccagttctttgctttcgaagttgc | 70 | 2 |
| NEENAss2_revII | tttttggcgcgcctactacgtactgttttcaattct | 71 | |
| NEENAss4_forII | aataaaggcgcgccgtccagaattttctccattga | 72 | 6 |
| NEENAss4_revII | aataaaggcgcgcctcttcactatccaaagctctca | 73 | |
| NEENAss13_forII | ttttatggcgcgcctagcttaatctcagattcgaatcgt | 74 | 7 |
| NEENAss13_revII | ttttatggcgcgcctagtatctacataccaatcatacaaatg | 75 | |
| NEENAss14_forII | tttttggcgcgcctttcacgatttggaatttga | 76 | 5 |
| NEENAss14_revII | tttttggcgcgcctctacaacattaaaacgaccatta | 77 | |
| NEENAss15_forII | tatataggcgcgccagggtttcgttttttgtttca | 78 | 3 |
| NEENAss15_revII | tatataggcgcgccttatctcctgctcaaagaaacca | 79 | |
| NEENAss18_forII | tatataggcgcgccactgtttaagcttcactgtct | 80 | 4 |
| NEENAss18_revII | tatataggcgcgcctttcttctaaagctgaaagt | 81 | |

TABLE 12-continued

Plant expression vectors

| plant expression vector | Composition of the expression cassette Promoter::SEQ ID NO::reporter gene::terminator | SEQ ID NO |
|---|---|---|
| LJK355 | p-KG86::SEQ ID NO5::c-GUS::t-nos | |
| LJK356 | p-KG86::SEQ ID NO6::c-GUS::t-nos | |
| LJK357 | p-KG86::SEQ ID NO7::c-GUS::t-nos | |

The resulting vectors are used to analyze NEENA molecules in experiments outlined below (example 6.2).

6.2 Analysis of NEENA Molecules Enhancing Gene Expression in Monocotyledonous Plant Tissues These experiments are performed by bombardment of monocotyledonous plant tissues or culture cells (Example 6.2.1) or by *Agrobacterium*-mediated transformation (Example 6.2.2). The target tissue for these experiments can be plant tissues (e.g. leaf tissue), cultured plant cells (e.g. maize Black Mexican Sweetcorn (BMS), or plant embryos for *Agrobacterium* protocols.

6.2.1 Transient Assay Using Microprojectile Bombardment

The plasmid constructs are isolated using Qiagen plasmid kit (cat#12143). DNA is precipitated onto 0.6 microM gold particles (Bio-Rad cat#165-2262) according to the protocol described by Sanford et al. (1993) (Optimizing the biolistic process for different biological applications. Methods in Enzymology, 217: 483-509) and accelerated onto target tissues (e.g. two week old maize leaves, BMS cultured cells, etc.) using a PDS-1000/He system device (Bio-Rad). All DNA precipitation and bombardment steps are performed under sterile conditions at room temperature. Black Mexican Sweet corn (BMS) suspension cultured cells are propagated in BMS cell culture liquid medium [Murashige and Skoog (MS) salts (4.3 g/L), 3% (w/v) sucrose, myo-inositol (100 mg/L), 3 mg/L 2,4-dichlorophenoxyacetic acid (2,4-D), casein hydrolysate (1 g/L), thiamine (10 mg/L) and L-proline (1.15 g/L), pH 5.8]. Every week 10 mL of a culture of stationary cells are transferred to 40 mL of fresh medium and cultured on a rotary shaker operated at 110 rpm at 27° C. in a 250 mL flask.

60 mg of gold particles in a siliconized Eppendorf tube are resuspended in 100% ethanol followed by centrifugation for 30 seconds. The pellet is rinsed once in 100% ethanol and twice in sterile water with centrifugation after each wash. The pellet is finally resuspended in 1 mL sterile 50% glycerol. The gold suspension is then divided into 50 microL aliquots and stored at 4° C. The following reagents are added to one aliquot: 5 microL of 1 microg/microL total DNA, 50 mlcroL 2.5 M CaCl$_2$, 20 microL 0.1 M spermidine, free base. The DNA solution is vortexed for 1 minute and placed at −80° C. for 3 min followed by centrifugation for 10 seconds. The supernatant is removed. The pellet is carefully resuspended in 1 mL 100% ethanol by flicking the tube followed by centrifugation for 10 seconds. The supernatant is removed and the pellet is carefully resuspended in 50 microL of 100% ethanol and placed at −80° C. until used (30 min to 4 hr prior to bombardment). If gold aggregates are visible in the solution the tubes are sonicated for one second in a waterbath sonicator just prior to use.

For bombardment, two-week-old maize leaves are cut into pieces approximately 1 cm in length and placed ad-axial side up on osmotic induction medium M-N-6-702 [N6 salts (3.96 g/L), 3% (w/v) sucrose, 1.5 mg/L 2,4-dichlorophenoxyacetic acid (2,4-D), casein hydrolysate (100 mg/L), and L-proline (2.9 g/L), MS vitamin stock solution (1 mL/L), 0.2 M mannitol, 0.2 M sorbitol, pH 5.8]. The pieces are incubated for 1-2 hours.

In the case of BMS cultured cells, one-week-old suspension cells are pelleted at 1000 g in a Beckman/Coulter Avanti J25 centrifuge and the supernatant is discarded. Cells are placed onto round ash-free No 42 Whatman filters as a 1/16 inch thick layer using a spatula. The filter papers holding the plant materials are placed on osmotic induction media at 27° C. in darkness for 1-2 hours prior to bombardment. Just before bombardment the filters are removed from the medium and placed onto on a stack of sterile filter paper to allow the calli surface to partially dry.

Each plate is shot with 6 microL of gold-DNA solution twice, at 1,800 psi for the leaf materials and at 1,100 psi for the BMS cultured cells. To keep the position of plant materials, a sterilized wire mesh screen is laid on top of the sample. Following bombardment, the filters holding the samples are transferred onto M-N-6-702 medium lacking mannitol and sorbitol and incubated for 2 days in darkness at 27° C. prior to transient assays.

The transient transformation via microprojectile bombardment of other monocotyledonous plants are carried out using, for example, a technique described in Wang et al., 1988 (Transient expression of foreign genes in rice, wheat and soybean cells following particle bombardment. Plant Molecular Biology, 11 (4), 433-439), .Christou, 1997 (Rice transformation: bombardment. Plant Mol. Biol. 35 (1-2)).

Expression levels of the expressed genes in the constructs described above (example 6.1) are determined by GUS staining, quantification of luminescence/fluorescence, RT-PCR, protein abundance (detection by specific antibodies) or metabolic products generated via the expression cassettes described above using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Plant tissues are vacuum-infiltrated 2 times for 15 minutes to aid even staining. Analyses of luciferase activities are performed as described above (see example 2 and 3.3).

In comparison to seed specific p-ZmKG86 promoter-only NEENA-less reporter gene constructs, the NEENA molecules all mediate strong enhancement in gene expression in these assays.

6.2.2 Transformation and Regeneration of Monocotyledonous Crop Plants

The *Agrobacterium*-mediated plant transformation using standard transformation and regeneration techniques may also be carried out for the purposes of transforming crop plants (Gelvin and Schilperoort, 1995, Plant Molecular Biology Manual, 2nd Edition, Dordrecht: Kluwer Academic Publ. ISBN 0-7923-2731-4; Glick and Thompson (1993) Methods in Plant Molecular Biology and Biotechnology, Boca Raton: CRC Press, ISBN 0-8493-5164-2). The transformation of maize or other monocotyledonous plants can be carried out using, for example, a technique described in U.S. Pat. No. 5,591,616. The transformation of plants using particle bombardment, polyethylene glycolmediated DNA uptake or via the silicon carbonate fiber technique is described, for example, by Freeling & Walbot (1993) "The maize handbook" ISBN 3-540-97826-7, Springer Verlag New York).

Expression levels of the expressed genes are determined by GUS staining, quantification of luminescence or fluorescence, RT-PCR or protein abundance (detection by specific antibodies) using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Plant tissues are vacuum-infiltrated 2 times for 15 minutes to aid even staining. Analyses of luciferase activities are performed as described above (examples 2 and 3.3).

In comparison to seed specific p-ZmKG86 promoter-only NEENA-less reporter gene constructs, the NEENA molecules mediate strong and tissue specific enhancement in gene expression in plants.

Example 7

Quantitative Analysis of NEENA Activity in Monocotyledonous Plants

This example describes the analysis of NEENA sequences with SEQ ID NO 1 and 2 in corn plants.
7.1 Vector Construction For analyzing NEENA sequences with SEQ ID NO 1 and 2 in monocotyledonous plants quantitatively, a pUC-based expression vector harboring an expression cassette composed of the NEENA-less, seed specific monocotyledonous promoter p-KG86 from *Z. mais* was combined with a coding sequence of the firefly luciferase (LUC) gene (Promega, Madison, Wis., USA) followed by the nopaline synthase (NOS) transcriptional terminator. Genomic DNA was extracted from *A. thaliana* green tissue using the Qiagen DNeasy Plant Mini Kit (Qiagen, Hilden, Germany). Genomic DNA fragments containing NEENA molecules were isolated by conventional polymerase chain reaction (PCR). Primers were designed on the basis of the *A. thaliana* genome sequence with a multitude of NEENA candidates. The reaction comprised 2 sets of primers (Table 11) and followed the protocol outlined by Phusion High Fidelity DNA Polymerase (Cat No F-540L, New England Biolabs, Ipswich, Mass., USA) using the following primers:

the combination with SEQ ID NO1 is given exemplary (SEQ ID NO87). Except for varying SEQ ID NO2, the nucleotide sequence is identical in the vectors (Table 12). The resulting vectors are summarized in table 12, with promoter molecules having the prefix p-, coding sequences having the prefix c-, and terminator molecules having the prefix t-.

TABLE 12

| plant expression vector | Composition of the expression cassette Promoter::SEQ ID NO::reporter gene::terminator | SEQ ID NO |
|---|---|---|
| RTP5679 | p-KG86::-::c-LUC::t-nos | |
| RTP5683 | p-KG86::SEQ ID NO1::c-LUC::t-nos | 87 |
| RTP5684 | p-KG86::SEQ ID NO2::c-LUC::t-nos | |

The resulting vectors were used to analyze NEENA molecules in experiments outlined below (Example 7.2).
7.2 Generation of Transgenic Maize Plants Maize germination, propagation, *A. tumefaciens* preparation and inoculations were done as previously described (WO2006136596, US20090249514) with the exception that the constructs RTP5679, RTP5683 and RTP5684 (cp. example 7.1) each contained a mutated AHAS gene driven by the corn ubiquitin promoter p-Ubi, mediating tolerance to imidazolinone herbicides for selection.
7.3 NEENA Sequences Mediate Strong and Tissue Specific Enhancement of Gene Expression in Corn Plants Tissue samples were collected from the generated transgenic plants from leaves and kernels. The tissue samples were processed and analyzed as described above (cp. example 3.3)

Figure 4:
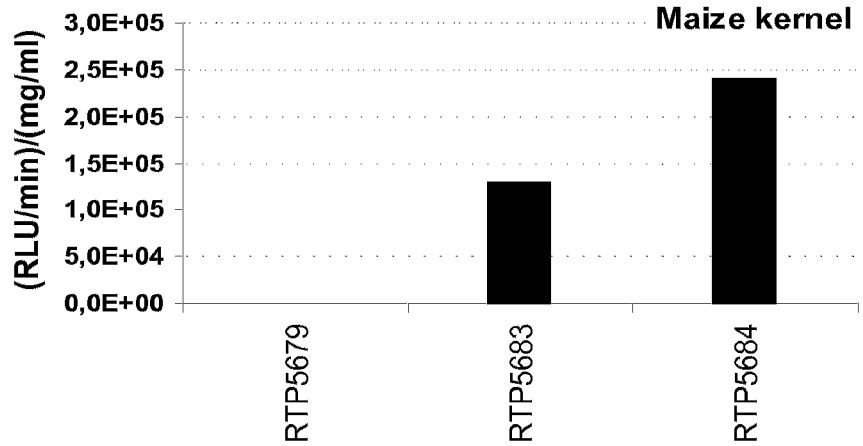
Figure 4:
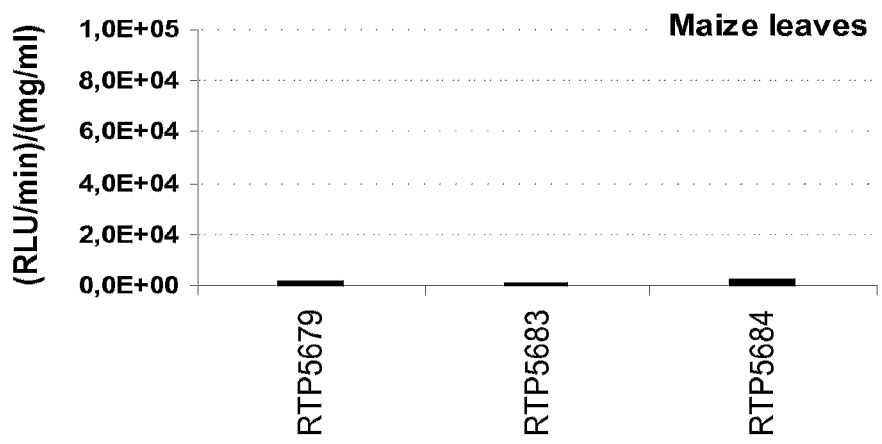

In comparison to the seed-specific p-KG86 promoter-only NEENA-less reporter gene construct, the two tested NEENA molecules (SEQ ID NO1 and NO2) mediated strong enhancements in gene expression in kernel (FIG. 4a). In contrast, no significant alterations in Luciferase activity mediated by NEENA molecules (SEQ ID NO1 and NO2) could be detected in maize leaves (FIG. 4b).

TABLE 11

Primer sequences

| Primer name | Sequence | SEQ ID No | PCR yielding SEQ ID NO |
|---|---|---|---|
| NEENAss1_forIII | atatacgcgtggtgcttaaacactctggtgagt | 83 | 1 |
| NEENAss1_revIII | atatggcgcgcctttgacctacaaaatcaaagcagtca | 84 | |
| NEENAss2_forIII | atatacgcgtagttctttgctttcgaagttgc | 85 | 2 |
| NEENAss2_revIII | atatggcgcgcctactacgtactgttttcaattct | 86 | |

Amplification during the PCR and purification of the amplification products was carried out as detailed above (example 1.2). Following a DNA restriction digest with MluI (10 U/microl) and AscI (10 U/microl) restriction endonucleases, the digested products were purified with the Qiagen Gel Extraction Kit (Qiagen, Hilden, Germany).

NEENA PCR fragments (see above) were cloned separately upstream of the firefly luciferase coding sequence using AscI restriction sites. The reaction yielded one binary vector with the p-KG86 promoter, the firefly luciferase coding sequence c-LUC and the t-nos terminator and two vectors harboring SEQ ID NO1 and NO2, immediately upstream of the firefly luciferase coding sequence (Table 12), for which Example 8

Quantitative Analysis of NEENA Activity in Rice Plants

This example describes the analysis of NEENA sequences with SEQ ID NO 1 and 2 in rice plants.
8.1 Vector Construction For analyzing NEENA sequences with SEQ ID NO 1 and 2 in rice plants quantitatively, pENTR/B vectors LJK1, LJK19 and LJK20 (compare example 1.3) were combined with a destination vector harboring the seed preferred rice PRO0090 promoter upstream of the recombination site using site specific recombination (LR-reaction) according to the manufacturers (Invitrogen, Carlsbad, Calif., USA) Gateway manual. The reactions yielded one binary vector with PRO0090 promoter, the firefly luciferase coding sequence c-LUC and the t-nos terminator as well as 2 vector harboring SEQ ID NO1 and NO2 immediately upstream of the firefly luciferase coding sequence (Table 13). Except for varying SEQ ID NO2, the nucleotide sequence is identical in the vectors (Table 13). The resulting vectors are summarized in table 13, with promoter molecules having the prefix p-, coding sequences having the prefix c-, and terminator molecules having the prefix t-.

TABLE 13

Plant expression vectors

| plant expression vector | Composition of the expression cassette Promoter::SEQ ID NO::reporter gene::terminator | SEQ ID NO |
|---|---|---|
| CD30977 | p- PRO0090::-::c-LUC::t-nos | |
| CD30971 | p- PRO0090::SEQ ID NO1::c-LUC::t-nos | — |
| CD30972 | p- PRO0090::SEQ ID NO2::c-LUC::t-nos | — |

The resulting vectors were used to analyze NEENA molecules in experiments outlined below (Example 8.2).

8.2 Generation of Transgenic Rice Plants

The *Agrobacterium* containing the respective expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were subcultured on fresh medium 3 days before co-cultivation (to boost cell division activity).

*Agrobacterium* strain LBA4404 containing the respective expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Figure 5:
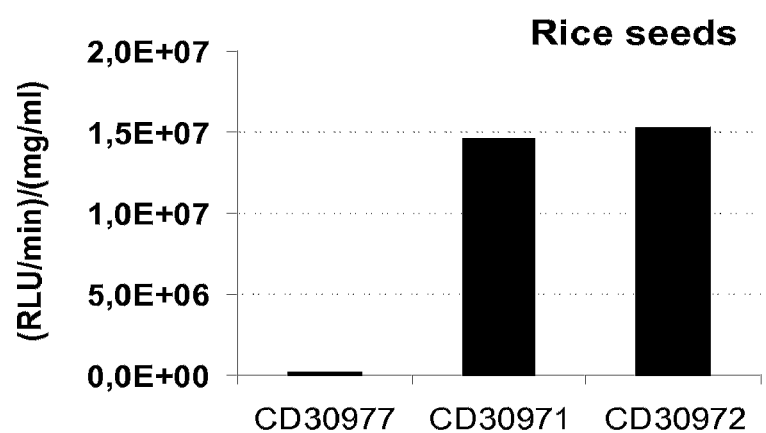
Figure 5:
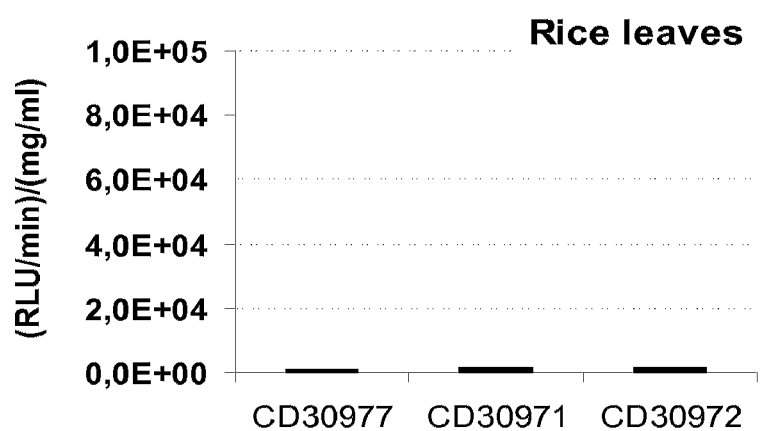

8.3 NEENA Sequences Mediate Strong and Tissue Specific Enhancement of Gene Expression in Rice Plants Tissue samples were collected from the generated transgenic plants from leaves and seeds. The tissue samples were processed and analyzed as described above (cp. example 3.3) In comparison to the seed-specific PRO0090 promoter-only NEENA-less reporter gene construct, the tested NEENA molecules (SEQ ID NO 1 and NO2) mediated strong enhancements in gene expression in seeds (FIG. 5a). In contrast, no significant alterations in Luciferase activity mediated by NEENA molecules (SEQ ID NO1 and NO2) could be detected in rice leaves (FIG. 5b).

FIGURE LEGENDS

FIG. 1: Luciferase reporter gene expression analysis in cotyledons of stably transformed *A. thaliana* plants of NEENA-less (LJK134) and NEENA-containing constructs (LJK71-LJK90) representing putative NEENA molecules deriving from seed-preferred expressed genes under the control of the p-AtPXR promoter. Expression values are shown in relation to the NEENA-less control construct (LJK134=1).

Figure 2:
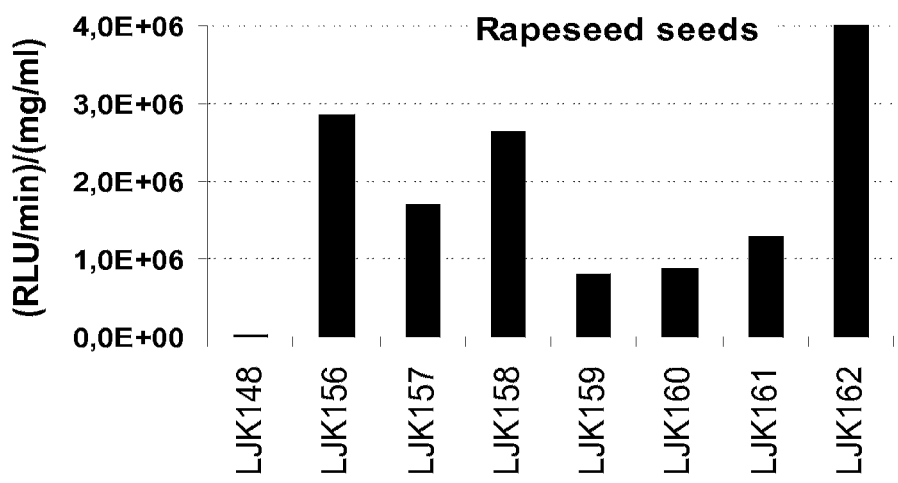
Figure 2:
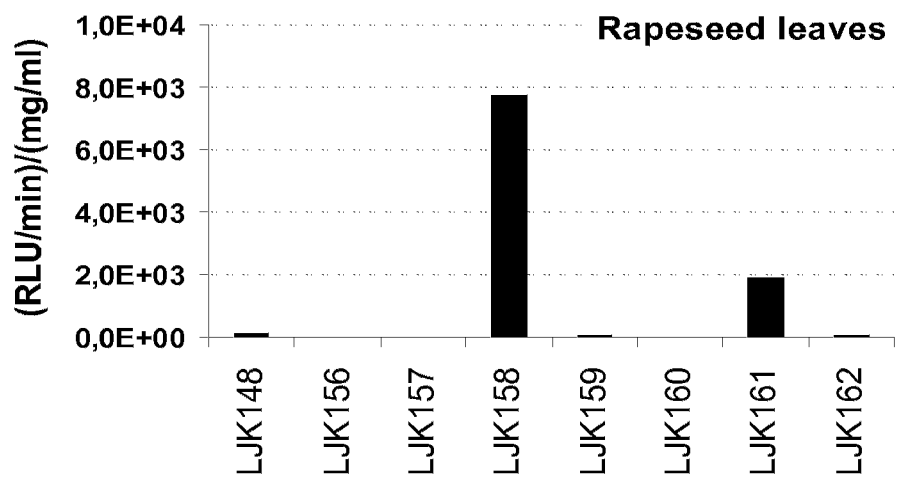
Figure 2:
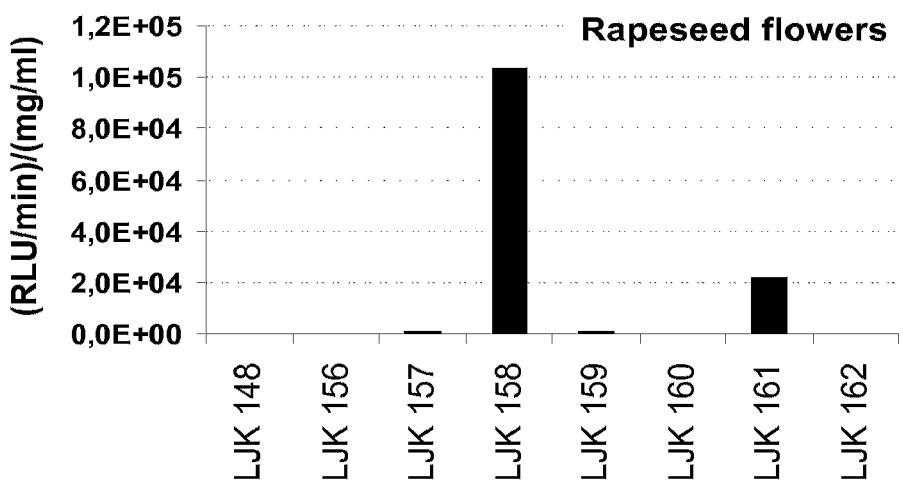

FIG. 2: Bar graphs of the luciferase reporter gene activity shown as relative light units (RLU) of independent transgenic oilseed rape plant lines harboring NEENA-less (LJK148) or NEENA-containing reporter gene constructs representing NEENA molecules from seed-preferred expressed genes (LJK156-LJK162) under the control of the p-AtPXR promoter and after normalization against the protein content of each sample. Expression values of plants harboring NEENA-containing constructs are shown in relation to plants expressing the NEENA-less control construct (LJK148) (averaged values, tissues of 20 independent transgenic plants analyzed). A) seed, B) leaf tissue, C) flowers FIG. 3: Bar graphs of the luciferase reporter gene activity shown as relative light units (RLU) of independent transgenic soybean plant lines harboring NEENA-less (LJK148) or NEENA-containing reporter gene constructs representing NEENA molecules from seed-preferred expressed genes (LJK156-LJK161) under the control of the p-AtPXR promoter and after normalization against the protein content of each sample. Expression values of plants harboring NEENA-containing constructs are shown in relation to plants expressing the NEENA-less control construct (LJK148) (averaged values, tissues of 10 independent transgenic plants analyzed). A) seed B) leaf tissue, C) flowers FIG. 4: Bar graph of the luciferase reporter gene activity shown as relative light units (RLU) of independent transgenic maize plant lines harboring NEENA-less (RTP5679) or NEENA-containing reporter gene constructs representing NEENA molecules from seed-preferred expressed genes (RTP5683-RTP5684) under the control of the p-KG86 promoter and after normalization against the protein content of each sample (averaged values, tissues of 15 independent transgenic plants analyzed). A) kernel, B) leaf tissue FIG. 5: Bar graph of the luciferase reporter gene activity shown as relative light units (RLU) of independent transgenic rice plant lines harboring NEENA-less (CD30977) or the NEENA-containing reporter gene construct representing a NEENA molecule from seed-preferred expressed genes (CD30971-CD30972) under the control of the rice PRO0090 promoter and after normalization against the protein content of each sample (averaged values, tissues of 15 independent transgenic plants analyzed). A) seeds, B) leaf tissue.

What is claimed is:

1. A method for production of a high expression seed-specific and/or seed-preferential expression construct, comprising functionally linking one or more nucleic acid expression enhancing nucleic acid (NEENA) molecule to a seed-specific and/or seed-preferential promoter and to a nucleic acid molecule to be expressed under the control of said seed-specific and/or seed-preferential promoter, wherein said NEENA is heterologous to said seed-specific and/or seed-preferential promoter and said nucleic acid molecule, and wherein said NEENA comprises:
  i) a nucleic acid molecule comprising the nucleic acid sequence of SEQ ID NO: 2;
  or
  ii) a nucleic acid molecule having at least 98% sequence identity to the nucleic acid sequence of SEQ ID NO: 2.

2. A method for producing a plant or part thereof with enhanced seed-specific and/or seed-preferential expression of one or more nucleic acid molecule compared to a respective control plant or part thereof, comprising:

a) introducing one or more NEENA comprising the nucleic acid molecule of or ii) of claim 1 into a plant cell, plant, or part thereof;
  b) integrating said one or more NEENA into the genome of said plant cell, plant, or part thereof to produce a transformed plant cell, whereby said one or more NEENA is functionally linked to an endogenous seed-specific and/or seed-preferential expressed nucleic acid heterologous to said one or more NEENA; and
  c) regenerating a plant or part thereof comprising said one or more NEENA from said transformed plant cell.

3. The method of claim 2, wherein the plant is a monocot or dicot plant.

4. The method of claim 2, wherein said one or more NEENA is functionally linked to the endogenous seed-specific and/or seed-preferential expressed nucleic acid close to the transcription start site of said nucleic acid.

5. The method of claim 2, wherein said one or more NEENA is functionally linked to the endogenous seed-specific and/or seed-preferential expressed nucleic acid 2500 bp or fewer away from the transcription start site of said nucleic acid.

6. The method of claim 2, wherein said one or more NEENA is functionally linked to the endogenous seed-specific and/or seed-preferential expressed nucleic acid upstream of the translational start site of the nucleic acid.

7. The method of claim 2, wherein said one or more NEENA is functionally linked to the endogenous seed-specific and/or seed-preferential expressed nucleic acid within the 5'UTR of the nucleic acid.

8. A method for producing a plant or part thereof with enhanced seed-specific and/or seed-preferential expression of one or more nucleic acid molecule compared to a respective control plant or part thereof, comprising:
   a) providing an expression construct comprising one or more NEENA comprising the nucleic acid molecule of i) or ii) of claim 1 functionally linked to a seed-specific and/or seed-preferential promoter and to a nucleic acid molecule under the control of said seed-specific and/or seed-preferential promoter, wherein said seed-specific and/or seed-preferential promoter and said nucleic acid molecule are heterologous to said one or more NEENA;
   b) integrating said expression construct into the genome of a plant or part thereof to produce a transformed plant or part thereof; and
   c) regenerating a plant or part thereof comprising said expression construct from said transformed plant or part thereof.

9. The method of claim 8, wherein the plant is a monocot or dicot plant.

10. The method of claim 8, wherein said one or more NEENA is functionally linked to the seed-specific and/or seed-preferential promoter close to the transcription start site of said nucleic acid molecule.

11. The method of claim 8, wherein said one or more NEENA is functionally linked to the seed-specific and/or seed-preferential promoter 2500 bp or fewer away from the transcription start site of said nucleic acid molecule.

12. The method of claim 8, wherein said one or more NEENA is functionally linked to the seed-specific and/or seed-preferential promoter upstream of the translational start site of the nucleic acid molecule, and wherein the expression of said nucleic acid molecule is under the control of said seed-specific and/or seed-preferential promoter.

13. The method of claim 8, wherein said one or more NEENA is functionally linked to the seed-specific and/or seed-preferential promoter within the 5'UTR of the nucleic acid molecule, and wherein the expression of said nucleic acid molecule is under the control of said seed-specific and/or seed-preferential promoter.

14. A recombinant expression construct comprising one or more NEENA functionally linked to a seed-specific and/or seed-preferential promoter and to a nucleic acid molecule to be expressed under the control of said seed-specific and/or seed-preferential promoter, wherein said NEENA is heterologous to said seed-specific and/or seed-preferential promoter and said nucleic acid molecule, and wherein said NEENA comprises:
   i) a nucleic acid molecule comprising the nucleic acid sequence of SEQ ID NO: 2;
   or
   ii) a nucleic acid molecule having at least 98% sequence identity to the nucleic acid sequence of SEQ ID NO: 2.

15. A recombinant expression vector comprising one or more recombinant expression construct of claim 14.

16. A transgenic plant cell, plant, or part thereof comprising one or more NEENA functionally linked to a seed-specific and/or seed-preferential promoter and to a nucleic acid molecule to be expressed under the control of said seed-specific and/or seed-preferential promoter, wherein said NEENA is heterologous to said seed-specific and/or seed-preferential promoter and said nucleic acid molecule, and wherein said NEENA comprises:
   i) a nucleic acid molecule comprising the nucleic acid sequence of SEQ ID NO: 2;
   or
   ii) a nucleic acid molecule having at least 98% sequence identity to the nucleic acid sequence of SEQ ID NO: 2.

17. A transgenic cell, plant, or part thereof comprising:
   a) the recombinant expression construct of claim 14; or
   b) a recombinant expression vector comprising one or more of said recombinant expression construct.

18. The transgenic cell of claim 17, selected or derived from the group consisting of bacteria, fungi, yeasts, or plants.

19. The transgenic plant or part thereof of claim 17, wherein said plant is a dicotyledonous plant.

20. The transgenic plant or part thereof of claim 17, wherein said plant is a monocotyledonous plant.

21. A transgenic cell, cell culture, seed, plant, plant part, or propagation material derived from the transgenic cell, plant, or part thereof of claim 17, wherein the transgenic cell, cell culture, seed, plant, plant part, or propagation material comprises said NEENA.

22. A method for the production of foodstuffs, animal feed, seeds, a pharmaceutical or a fine chemical comprising:
   a) providing a transgenic cell culture, seed, plant, plant part, or propagation material derived from the transgenic cell or plant of claim 21; and
   b) preparing foodstuffs, animal feed, seeds, a pharmaceutical or a fine chemical from the transgenic cell culture, seed, plant, plant part, or propagation material of a).

23. A method for enhancing seed-specific and/or seed-preferential expression of one or more nucleic acid molecule in a plant compared to a respective control plant, comprising transiently introducing into a plant the recombinant expression construct of claim 14.

* * * * *